US008034790B2

(12) United States Patent
Chada

(10) Patent No.: US 8,034,790 B2
(45) Date of Patent: Oct. 11, 2011

(54) USE OF MDA-7 TO INHIBIT PATHOGENIC INFECTIOUS ORGANISMS

(75) Inventor: Sunil Chada, Missouri City, TX (US)

(73) Assignee: Introgen Therapeutics, Austin, TX (US)

( * ) Notice: Subject to any disclaimer, the term of this patent is extended or adjusted under 35 U.S.C. 154(b) by 481 days.

(21) Appl. No.: 11/001,702

(22) Filed: Dec. 1, 2004

(65) Prior Publication Data

US 2005/0233959 A1 Oct. 20, 2005

Related U.S. Application Data

(63) Continuation of application No. 60/526,031, filed on Dec. 1, 2003.

(51) Int. Cl.
*A61K 38/20* (2006.01)
*A61K 48/00* (2006.01)
(52) U.S. Cl. .............. 514/44 R; 514/3.7; 424/85.2
(58) Field of Classification Search ............... 514/44 R, 514/3.7; 424/85.2
See application file for complete search history.

(56) References Cited

U.S. PATENT DOCUMENTS

| | | | |
|---|---|---|---|
| 4,682,195 A | 7/1987 | Yilmaz | 357/23.4 |
| 4,683,202 A | 7/1987 | Mullis | 435/91 |
| 4,797,368 A | 1/1989 | Carter et al. | 435/320 |
| 5,139,941 A | 8/1992 | Muzyczka et al. | 435/172.3 |
| 5,179,122 A | 1/1993 | Greene et al. | 514/458 |
| 5,399,363 A | 3/1995 | Liversidge et al. | 424/490 |
| 5,466,468 A | 11/1995 | Schneider et al. | 424/450 |
| 5,543,158 A | 8/1996 | Gref et al. | 424/501 |
| 5,633,016 A | 5/1997 | Johnson | 424/649 |
| 5,641,515 A | 6/1997 | Ramtoola | 424/189 |
| 5,643,761 A | 7/1997 | Fisher et al. | 435/91.1 |
| 5,645,897 A | 7/1997 | Andra | 427/526 |
| 5,705,629 A | 1/1998 | Bhongle | 536/25.34 |
| 5,710,137 A | 1/1998 | Fisher | 514/44 |
| 5,739,169 A | 4/1998 | Ocain et al. | 514/658 |
| 5,747,469 A | 5/1998 | Roth et al. | 514/44 |
| 5,798,339 A | 8/1998 | Brandes | 514/34 |
| 5,801,005 A | 9/1998 | Cheever et al. | 435/7.24 |
| 5,824,311 A | 10/1998 | Greene et al. | 424/138.1 |
| 5,824,348 A | 10/1998 | Fujiu et al. | 425/120 |
| 5,830,880 A | 11/1998 | Sedlacek et al. | 514/44 |
| 5,846,225 A | 12/1998 | Rosengart et al. | 604/115 |
| 5,846,233 A | 12/1998 | Lilley et al. | 604/414 |
| 5,846,945 A | 12/1998 | McCormick | 514/44 |
| 6,069,134 A | 5/2000 | Roth et al. | 514/44 |
| 6,132,980 A | 10/2000 | Wang et al. | 435/7.23 |
| 6,168,791 B1 | 1/2001 | Larsen et al. | 424/158.1 |
| 6,177,074 B1 | 1/2001 | Glue et al. | 424/85.7 |
| 6,204,022 B1 | 3/2001 | Johnson et al. | 435/69.51 |
| 6,207,145 B1 | 3/2001 | Tovey | 424/85.4 |
| 6,207,648 B1 | 3/2001 | Waxman et al. | 514/44 |
| 6,250,469 B1 | 6/2001 | Kline | 206/571 |
| 6,326,466 B1 * | 12/2001 | Bottaro et al. | 530/324 |
| 6,331,525 B1 | 12/2001 | Chiou et al. | 514/44 |
| 6,342,379 B1 | 1/2002 | Tsien et al. | 435/173.4 |
| 6,348,352 B1 | 2/2002 | Shepard et al. | 435/455 |
| 6,350,589 B1 | 2/2002 | Morris et al. | 435/41 |
| 6,355,622 B1 | 3/2002 | Fisher | 514/44 |
| 6,372,218 B1 | 4/2002 | Cummins | 424/184.1 |
| 6,379,701 B1 | 4/2002 | Tracy et al. | 424/486 |
| 6,407,218 B1 | 6/2002 | Tamarkin et al. | 530/389.1 |
| 6,855,686 B2 | 2/2005 | Fischer | 514/2 |
| 2002/0091098 A1 | 7/2002 | Fisher | 514/44 |
| 2002/0183271 A1 | 12/2002 | Chada et al. | 514/44 |
| 2003/0066095 A1 | 4/2003 | Baubet et al. | 800/3 |
| 2003/0082140 A1 | 5/2003 | Fisher | 424/93.2 |
| 2003/0147966 A1 | 8/2003 | Franzen et al. | 424/491 |
| 2003/0223938 A1 | 12/2003 | Nagy et al. | 424/46 |
| 2004/0009939 A1 | 1/2004 | Chada et al. | 514/44 |
| 2004/0191223 A1 | 9/2004 | Fisher | 424/93.2 |
| 2005/0101770 A1 | 5/2005 | Presta | 530/388.15 |
| 2005/0143336 A1 | 6/2005 | Ramesh et al. | 514/44 |
| 2005/0191277 A1 | 9/2005 | Fisher | 424/93.2 |
| 2005/0250127 A1 | 11/2005 | Fisher et al. | 435/6 |
| 2006/0110376 A1 | 5/2006 | Fisher et al. | 424/93.21 |
| 2006/0134801 A1 | 6/2006 | Chada et al. | 436/177 |
| 2006/0292157 A1 | 12/2006 | Fisher et al. | 424/155.1 |

FOREIGN PATENT DOCUMENTS

| | | |
|---|---|---|
| EP | 0 266 032 | 5/1988 |
| WO | WO 95/11986 | 5/1995 |
| WO | WO 95/28948 | 11/1995 |
| WO | WO 98/07408 | 2/1998 |
| WO | WO 98/16655 | 4/1998 |
| WO | WO 98/28425 | 7/1998 |
| WO | WO 98/35554 | 8/1998 |
| WO | WO 00/05356 | 2/2000 |
| WO | WO 00/26368 | 5/2000 |
| WO | WO 00/61626 | 10/2000 |
| WO | WO 00/71096 | 11/2000 |
| WO | WO 01/05437 | 2/2001 |
| WO | WO 01/60365 | 8/2001 |
| WO | WO 02/04511 | 1/2002 |
| WO | WO 02/45737 | 6/2002 |
| WO | WO 03/075952 | 9/2003 |
| WO | WO 03/087308 | 10/2003 |

OTHER PUBLICATIONS

Wilson et al. Adv. Drug Deliv. Rev. 46:205-209; 2001.*

(Continued)

*Primary Examiner* — Anne Marie S Wehbe
(74) *Attorney, Agent, or Firm* — Fulbright & Jaworski L.L.P.

(57) ABSTRACT

Methods of suppressing or preventing an infection of a subject by a pathogen that involve administering to the subject a composition that includes a therapeutically effective amount of an MDA-7 polypeptide or a nucleic acid encoding the MDA-7 polypeptide, and a pharmaceutically acceptable preparation suitable for delivery to the subject, wherein the MDA-7 suppresses or prevents the infection, are disclosed. Also disclosed are methods of suppressing or preventing a viral infection of a cell, including obtaining an MDA-7 polypeptide or a nucleic acid encoding the MDA-7 polypeptide, and contacting the cell with the MDA-7 polypeptide or the nucleic acid encoding the MDA-7 polypeptide, wherein the MDA-7 suppresses or prevents infection of the cell.

32 Claims, 14 Drawing Sheets

OTHER PUBLICATIONS

Thomas et al. Nature Rev./Genet. 4: 346-358; 2003.*
Caudell et al. (2002) J. Immunol., vol. 168, 6041-6046.*
Uchikawa et al. (2000) Infection and Immunity, vol. 68(11), pp. 6233-6299.*
Taylor et al. (2000) Infection and Immunity, vol. 68(4), 1815-1819.*
La Flamme et al. (2001) Infection and Immunity, vol. 69(12), pp. 7445-7452.*
Nishimura et al. (2004) J. Parasitol., vol. 90(4)740-745.*
Albert et al., "Dendritic cell matuation is required for the cross-tolerization of CD8+ T cells," *Nat Immunol*, 2(11):1010-1017, 1998.
Anderson, "Human gene therapy," *Nature*, 392:25-30, 1998.
Angiolillo et al., "A role for the interferon-inducible protein 10 in inhibition of angiogenesis by interleukin-12," *Ann. NY Acad Sci.*, 795:158-167, 1996.
Austin-Ward and Villaseca, "Gene therapy and its applications," abstract only, *Rev. Med. Chil.*, 126:838-845, 1998.
Balachandran et al., "Activation of the dsRNA-dependent protein kinase, PKR, induces apoptosis through FADD-mediated death signaling," *EMBO J.*,17(23):6888-6902, 1998.
Beretta et al., "Rapamycin blocks the phosphorylation of 4E-BP1 and inhibits cap-dependent initiation of translation," *EMBO J*, 15:658-664, 1996.
Beretta et al., "Rapamycin stimulates viral protein synthesis and augments the shutoff of host protein synthesis upon picornavirus infection," *J. Virol*, 70:8993-8996, 1996.
Blumberg et al., "Inyrtlrukin 20: discovery, receptor identification, and role in epidermal function," *Cell* 104:9-19, 2001.
Bonavida et al., "Selectivity of TRAIL-mediated apoptosis of cancer cells and synergy with drugs: The trail to non-toxic cancer therapeutics," *Int J Oncol*, 15:793-802, 1999.
Boucher et al., "Status of gene therapy for cystic fibrosis lung disease ," *J. Clin. Invest.*, 103:441-445, 1999.
Bowie et al., "Deciphering the message in protein sequences: tolerance to amino acid substitutions," *Science*, 247(4948):1306-10, 1990.
Bukowski et al., "Signal transducton abnormalities in T lymphyocytes from patients with advanced renal carcinoma: Clinical relevance and effects of cytokine therapy," *Clin. Cancer Res.*, 4(10):2337-2347, 1998.
Cao et al., "Adenoviral transfer of mda-7 leads to BAX up-regulation and in mesothelioma cells, and is abrogated by over-expression of BCL-XL," *Molecular Medicine*, 8(12):869-876, 2002.
Caudell et al., "The protein product of the tumor suppressor gene, melanoma differentiation-associated gene 7, exhibits immunostimulatory activity and is designated IL-24,"*J. Immunol*, 168(12):6041-6046, 2002.
Chattergoon et al., "Targeted antigen delivery to antigen-presenting cells including dendritic cells by engineered Fas-medicated apoptosis," *Nat Biotechnol*, 18(9):974-979, 2000.
Chen and Tan, "Inhibition of the c-Jun N-terminal kinase (JNK) signaling pathway by curcumin," *Ocongene*, 17:173-178, 1998.
Chinnaiyan et al., "Combined effect of tumor necrosis factor-related apoptosis-inducing ligand and ionizing radiation in breast cancer therapy," *Proc Nat'l Acad Sci USA*. 97:1754-1759, 2000.
Christodoulides et al., "Immunization with recombinant class 1 outer-membrane protein from *Neisseria meningitidis*: influence of liposomes and adjuvants on antibody avidity, recognition of native protein and the induction of a bactericidal immune response against *meningococci*," *Microbiology*, 144:3027-3037, 1998.
Cross et al., "A p53-dependent mouse spindle checkpoint," *Science*, 267:1353-1356, 1995.
Crystal, "Transfer of genes to humans: early lessons and obstacles to success," *Science*, 270:404-409, 1995.
Cuddihy et al., "Double-stranded-RNA-activated protein kinase PKR enhances transcriptional activation by tumor suppressor p53," *Mol. Cell. Biol.*, 19(4):2475-2484, 1999.
Cunningham et al., "Clinical and local biological effects of an intratumoral injection of *mda-7* (IL24; INGN 241) in patients with advanced carcinoma: a phase I study," *Molecular Therapy*, 11(1):149-159, 2005. (Written in 2003 with Applicant).

Dagon et al., "Double-stranded RNA-dependent protein kinase, PKR, down-regulates CDC2/cyclin B1 and induces apoptosis in non-transformed but not in v-mos transformed cells," *Oncogene*, 20(56):8045-8056, 2001.
Davidson et al., "Intralesional cytokine therapy in cancer: A pilot study of GM-CSF infusion in mesothelioma," *J. Immunother.*, 21:389-398, 1998.
De Waal Malefyt et al., "Interleukin 10(IL-10) inhibits cytokine synthesis by human monocytes: an autoregulatory role of IL-10 produced by monocytes," *J. Exp. Med.* 174:1209-1220, 1991.
Deb et al., "RNA-dependent protein kinase PKR is required or activation of NF-κB by IFN-γ in a STAT1-independent pathway," *J. Immunol*, 166:6170-6180, 2001.
Deonarain, "Ligand-targeted receptor-mediated vectors for gene delivery," *Exp. Opin. Ther. Patents*, 8(1):53-69, 1998.
Dragovich et al., "Signal transduction pathways that regulate cell survival and cell death," *Oncogene*, 17:3207-3213, 1998.
Dumoutier and Renauld, "Viral and cellular interleukin-10 (IL-10)-related cytokines: from structures to functions," *Eur Cytokine Netw*, 13(2):5-15, 2002.
Dumoutier et al., "Cutting edge: STAT activation by IL-19, IL-20 and mda-7 through IL-20 receptor complexes of two types," *J Immunol*, 167:3545-3549, 2001.
Dumoutier et al., "Human interleukin-10-related T cell-derived inducible factor: molecular cloning and functional characterization as an hepatocyte-stimulating factor," *Proc. Natl. Acad. Sci. USA*, 97:10144-10149, 2000.
Eck and Wilson, "Gene-based therapy," *Goodman & Gilman's The Pharmacological Basis of Therapeutics*, McGraw-Hill, 77-101, 1996.
Ekmekcioglu et al., "Differential increase of Fas ligand expression on metastatic and thin or thick primary melanoma cells compared with interleukin-10," *Melanoma Research* 9:261-272, 1999.
Ekmekcioglu et al., "Down-regulated melanoma differentiation associated gene (MDA-7) expression in human melanomas," *Intl. J. Cancer.*, 94:54-59, 2001.
Ekmekcioglu et al., "Negative association of melanoma differentiation-associated gene (mda-7) and inducible nitric oxide synthase (iNOS) in human melanoma: MDA-7 regulated iNOS expression in melanoma cells," *Mol. Cancer Therapeutics*, 2:9-17, 2003.
El-Kareh and Secornb, "Theoretical models for drug delivery to solid tumors," *Crit. Rev. Biomed. Eng.*, 25:503-571, 1997.
Ellerhorst et al., "Loss of MDA-7 expression with progression of melanoma" *J Clin Oncol*, 20:1069-1074, 2002.
Erlandsson, "Molecular genetics of renal cell carcinoma," *Cancer Genet. Cytogenet*, 104:1-18, 1998.
Fathallah-Shaykh et al., "Gene transfer of IFN-γ established brain tumors represses growth by antiangiogenesis," *J. Immunol.*, 164:217-222, 2000.
Feng et al., "Identification of double-stranded RNA-binding domains in the interferon-induced double-stranded RNA-activated p68 kinase," *Proc. Natl. Acad. Sci., USA*, 89:5447-5451, 1992.
Fickenscher et al., "The interleukin-10 family of cytokines.," *Trends Immunol*, 23: 89-96, 2002.
Fisher et al, "*mda-7*/L1-24, a novel cancer selective apoptosis inducing cytokine gene," *Cancer Biol Therapy*, 2(4 suppl. 1):S24-S37, 2003.
Frigerio et al., "Analysis of 2166 clones from a human colorectal cancer cDNA by partial sequencing," *Human Molecular Genetics*, 4(1):37-43, 1995.
Fulci et al., "p53 and brain tumors: from gene mutations to gene therapy," *Brain Pathol.*, 8(4):599-613, 1998.
Gale et al., "Antiapoptotic and oncogenic potentials of hepatitis C virus are linked to interferon resistance by viral repression of the PKR protein kinase," *J. Virol*, 7(8):6505-6516, 1999.
Gale et al., "Repression of the PKR protein kinase by the hepatitis C virus NS5A protein: a potential mechanism of interferon resistance," *Clinical and Diagnostic Virology*, 10:157-162, 1998.
Gale et al., "Translational control of viral gene expression in Eukaryotes," *Microbiol Mol Biol Rev*, 64(2):239-280, 2000.
Hartmann et al., "High frequency of p53 gene mutations in primary breast cancers in Japanese women, a low-incidence population," *Br. J. Cancer*, 73(8):896-901, 1996.

Hartmann et al., "Overexpression and mutations of p53 in metastatic malignant melanomas," *Int. J. Cancer*, 67(3):313-317, 1996.

Hellstrand et al., "Histamine and cytokine therapy," *Acta. Oncol.*, 37:347-353, 1998.

Ho et al., "Internal radiation therapy for patients with primary or metastatic hepatic cancer," *Cancer*, 83:1894-1907, 1998.

Howard et al., "Biological properties of interleukin 10," *J. Clin. Immunol.* 12:239-247, 1992.

Huang et al., "Genomic structure, chromosomal localization and expression profile of a novel melanoma differentiation associated (mda-7) gene with cancer specific growth suppressing and apoptosis inducing properties," *Oncogene*, 20:7051-7063, 2001.

Hui and Hashimoto, "Pathways for potentiation of immunogenicity during adjuvant-assisted immunizations with *Plasmodium falciparum* major merozoite surface protein 1," *Infect. Immun.*, 66:5329-3536, 1998.

Jagus et al., "PKR, apoptosis and cancer," *Int. J. Biochem.*, 31:123-138, 1999.

Jiang and Fisher, "Use of a sensitive and efficient subtraction hybridization protocol for the identification of genes differentially regulated during the induction of differentiation in human melanoma cells," *Mol. Cel. Differ.*, 1(3): 285-299, 1993.

Jiang et al., "A molecular definition of terminal cell differentiation in human melanoma cells," *Molecular and Cellular Differentiation*, 2(3):221-239, 1994.

Jiang et al, "Subtraction hybridization identifies a novel melanoma differentiation associated gene, mda-7, modulated during human melanoma differentiation, growth and progression," *Oncogene*, 11:2477-2486, 1995.

Jiang et al., "The melanoma differentiation associated gene *mda*-7 suppresses cancer cell growth," *Proc. Natl Acad. Sci. USA*, 93:9160-9165, 1996.

Jiménez et al., "Signals leading to apoptosis-dependent inhibition of neovascularization by thrombospondin-1," *Nat Med*, 6(1):41-48, 2000.

Johnson and Hamdy, "Apoptosis regulating genes in prostate cancer," *Oncol. Rep.*, 5:553-557, 1998.

Joki et al., "Continuous release of endostatin from microencapsulated engineered cells for tumor therapy," *Nat Biotech*, 19(1):35-39, 2001.

Judware et al., "Partial characterization of a cellular factor that regulates the double-straded RNA-dependent eIF-2α kinase in 3T3-F442A fibroblasts," *Mol. Cell Biol.*, 11(6):3259-3267, 1991.

Kaufman, "Orchestrating the unfolded protein response in health and disease," *J. Clin Invest*, 110(10):1389-1398, 2002.

Kawabe et al., "Adenovirus-mediated mda-7 gene expression radiosensitizes non-small cell lung cancer cells via TP53-independent mechanisms," *Molecular Therapy*, 6(5):637-644, 2002.

Kaye et al., "A single amino acid substitution results in a retinoblastoma protein defective in phosphorylation and oncoprotein building," *Proc. Natl. Acad. Sci., USA*, 87:6922-6926, 1990.

Keane et al., "Chemotherapy augments TRAIL-induced apoptosis in breast cell lines," *Cancer Res.* 59:734-741, 1999.

Kim et al., "Bid-induced cytochrome c release is mediated by a pathway independent of mitochondrial permeability transition pore and Bax.," *J Biol Chem*, 275(50):39474-39481, 2000.

Knappe et al., "Induction of a novel cellular homolog of interleukin-10, AK155, by transformation of T lymphocytes with herpesvirus saimiri," *J. Virol.*, 74: 3881-3887, 2000.

Kölmel, "Cytology of neoplastic meningosis," *J. Neurooncol.*, 38:121-125, 1998.

Koromilas et al., "Malignant transformation by a mutant of the IFN-inducible dsRNA-dependent protein kinase," *Science*, 257(5077):1685-1689, 1992.

Kotenko et al., "Human cytomegalovirus harbors its own unique IL-10 homolog (cmvIL-10)," *Proc. Natl. Acad. Sci. USA*, 97:1695-1700, 2000.

Kumar et al., "Deficient cytokine signaling in mouse embryo fibroblasts with a targeted deletion in the PKR gene: role of IRF-1 and NF-κB," *EMBO J*, 16:406-416, 1997.

Kumar et al., "Double-stranded RNA-dependent protein kinase activates transcription fact NF-κB by phosphorylating IκB," *Proc. Natl. Acad. Sci., USA*, 91:6288-6292, 1994.

Lebedeva et al., "The cancer growth suppressing gene mda-7 induces apoptosis selectively in human melanoma cells," *Oncogene*, 21:708-718, 2002.

Lebedeva et al., "Restoring apoptosis as a strategy for cancer gene therapy: focus on *p53* and *mda*-7," *Semin Cancer Biol*, 13(2):169-178, 2003.

Leonardo et al., "The involvment of NF-κB in β-interferon gene regulation reveals its role as widely inducible mediator of signal transduction," *Cell*, 57:287-294, 1989.

Levine et al., "The p53 tumor suppressor gene," *Nature*, 351:453-456, 1991.

Liebermann et al., "AP-1 (Fos/Jun) transcription factors in hematopoietic differentiation and apoptosis," *Int. J. Oncol.*, 12:685-700, 1998.

Madireddi et al., "A novel melanoma differentiation associated gene with promise for cancer gene therapy," *Cancer Gene Therapy*, 465:239-261, 2000.

Madireddi et al., "AP-1 and C/EBP transcription factors contribute to mda-7 gene promoter activity during human melanoma differentiation," *J Cell Physiol*, 185:36-46, 2000.

Magi-Galluzzi et al., "Proliferation, apoptosis and cell cycle regulation in prostatic carcinogenesis," *Anal. Quant. Cytol. Histol.*, 20:343-350, 1998.

Maheshwari et al., "Differential effects of interferon gamma and alpha on in vitro model of angiogenesis," *J Cell Physiol*, 146:164-169, 1991.

Majumder et al., "Regulation of human IP-10 gene expression in astrocytoma cells by inflammatory cytokines," *J. Neurosci. Res.*, 54:169-180, 1998.

Makrides et al., "Components of vectors for gene transfer and expression in mammalian cells," *Protein Exp. Pur.*, 17:183-202, 1999.

Mangray and King, "Molecular pathobiology of pancreatic adenocarcinoma," *Front Biosci.*, 3:D1148-1160, 1998.

Maran et al., "Blockage of NF-κB signaling by selective ablation of an mRNA target by 2-5A antisense chimeras," *Science*, 265:789-792, 1994.

Marsters et al., "Control of apoptosis signaling by Apo2 ligand," *Recent Prog Horm Res* 54:225-234, 1999.

Mayer, "Future developments in the selectivity of anticancer agents: drug delivery and molecular target strategies," *Cancer Metastasis Rev.*, 17:211-8, 1998.

Merrick and Hershey, "The pathway and mechanism of eukaryotic protein synthesis," In: *Translational Control*, Hershey et al., (Eds.), Cold Spring Harbor Laboratory Press, NY, 31-69, 1996.

Meurs et al., "Molecular cloning and characterization of the human double-stranded RNA-activated protein kinas induced by interferon," *Cell*, 62:379-390, 1990.

Meurs et al., "Tumor suppressor function of the interferon-induced double-stranded RNA-activated protein kinase," *Proc. Natl. Acad. Sci., USA*, 90:232-236, 1993.

Mhashilkar et al., "Melanoma differentiation associated gene-7 (mda-7): a novel anti-tumor gene for cancer gene therapy," *Mol. Medicine*. 7:271-282, 2001.

Mhashilkar et al., "MDA-7 negatively regulates the β-catenin and PI3K signaling pathway s in breat and lung tumor cells," *Mol Ther*, 8(2):207-219, 2003.

Miller et al., "Targeted vectors for gene therapy," *FASEB J.*, 9:190-199, 1995.

Miyashita and Reed, "Tumor suppressor p53 is a direct transcriptional activator of the human *bax* gene," *Cell*, 80:293-299, 1995.

Moore et al., "Homology of cytokine synthesis inhibitory factor (IL-10) to the epstein-barr virus gene BCRF1," *Science*, 248:1230-1234, 1990.

Mountain, "Gene therapy: the first decade," *TIB Tech*, 18:119-127, 2000.

Mumby and Walter, "Protein phosphatases and DNA tumor viruses: transformation through the backdoor?," *Cell Regul.*, 2:589-598, 1991.

Natoli et al., "Apoptotic, non-apoptotic, anti-apoptotic pathways of tumor necrosis, factor signalling," *Biochem. Pharmacol.*, 56(8):915-920, 1998.

Nemunaitis et al., "Selective replication and oncolysis in p53 mutant tumors with ONYX-015, an E1B-55kD gene-deleted adenovirus, in patients with advanced head and neck cancer: a phase II trial," *Cancer Res.*, 60:6359-6366, 2000.

Nemunaitis, "Use of macrophage colony-stimulating factor in the treatment of fungal infections," *Clin Infect Dis*, 26(6):1279-1281, 1998.

Ochi et al., "A case of small pancreatic cancer diagnosed by serial follow-up studies promptly by a positive K-ras point mutation in pure pancreatic juice," *Am. J. Gastroenterol.*, 93:1366-1368, 1998.

Oh et al., "Conservation between animals and plants of the *cis*-acting element involved in the unfolded protein response," *Biochem Biophys Res Commun*, 301:225-230, 2003.

Pataer et al., "Adenoviral Bak overexpression mediates caspase-dependent tumor killing," 60: 788-792, 2000.

Pataer et al., "Adenoviral transfer of the melanoma differentiation-associated Gene 7 (mda7) induces apoptosis of lung cancer cells via up-regulation of the double-stranded RNA-dependent protein kinase (PKR)," *Cancer Res.*, 62(8):2239-2243, 2002.

Pavio et al., "Protein synthesis and endoplasmic reticulum stress can be modulated by the hepatitis C virus envelope protein E2 through the Eukaryotic initiation factor $2\alpha$ kinase PERK," *J. Virol*, 77(6):3578-3585, 2003.

Peng et al., "Mitotic and G2 checkpoint control: regulation of 14-3-3 protein binding by phosphorylation of Cdc25C on serine-216," *Science*, 277:1501-1505, 1997.

Petryshyn et al., "Growth-related expression of a double-stranded RNA-dependent protein kinase in 3T3 cells," *J. Biol. Chem.*, 259(23):14736-14742, 1984.

Petryshyn et al., "Detection of activated double-stranded RNA-dependent protein kinase in 3T3-F442A cells," *Proc. Natl. Acad. Sci., USA*, 85(5):1427-1431, 1988.

Pietras et al., "Remission of human breast cancer xenografts on therapy with humanized monoclonal antibody to HER-2 receptor and DNA reactive drugs," *Oncogene*, 17:2235-49, 1998.

Qin et al., "Interferon-$\beta$ gene therapy inhibits tumor formation and causes regression of established tumors in immune-deficient mice," *Proc. Nat'l Acad. Sci. USA*, 95(24):1411-1416, 1998.

Ramesh et al., "Inhibition of lung tumor growth following adenovirus-mediated mda-7 gene expression in vivo," *Proc. Amer. Assoc. Canc. Res. Annual Meeting*, 42:657, 2001.

Ramesh et al., "Melanoma differentiation-associated gene 7/interleukin (IL)-24 is a novel ligand that regulates angiogenesis via the IL-22 receptor," *Cancer Res.*, 63(16):5105-5113, 2003.

Ramesh et al., "Successful treatment of primary and disseminated human lung cancers by systemic delivery of tumor suppressor genes using an improved liposome vector," *Molecular Therapy*, 3(3):337-350, 2001.

Reed et al., "Structure-function analysis of Bcl-2 family proteins," *Adv. Exp. Med. Biol.*, 406:99-112, 1996.

Reed, "Bcl-2 family proteins: regulators of apoptosis and chemoresistance in hematologic malignancies," *Semin Hematol.*, 34(4 Suppl. 5):9-19, 1997.

Restifo et al., "Hierarchy, tolerance, and dominance in the antitumor T-cell response," *J. Immunother.*, 24(3):193-194, 2001.

Restifo et al., "Building better vaccines: how apoptotic cell death can induce inflammation and activate innate and adaptive immunity," *Curr Opin Immunol*, 12(5):597-603, 2000.

Rich and Kupper, "Cytokines: IL-20—a new effector in skin inflammation," *Curr Biol*, 11:R531-R534, 2001.

Robbins and Ghivizzani, "Viral vectors for gene therapy," *Pharmacol. Ther*, 80(1):35-47, 1998.

Ron, "Translational control in the endoplasmic reticulum stress response," *J. Clin Invest*, 110(10):1383-1388, 2002.

Rosse et al., "Bcl-2 prolongs cell survival after bax-induced release of cytochrome c," *Nature* 391:496-499, 1998.

Rudinger, "Characteristics of the amino acids as components of a peptide hormone sequence," *Peptide Hormones*, University Park Press, Jun. 1-7, 1976.

Russell et al., "Radiosensitization of human tumor cell lines induced by the adenovirus-mediated expression of an anti-Ras single-chain antibody fragment," *Cancer Res.*, 59:5239-5244, 1999.

Saeki et al., "Inhibition of human lung cancer growth following adenovirus-mediated mda-7 gene expression in vivo," *Oncogene*, 21:4558-4566, 2002.

Saeki et al., "Tumor-suppressive effects by adenovirus-mediated mda-7 gene transfer in non-small cell lung cancer cell in vitro," *Gene Therapy*, 7:2051-2057, 2000.

Saelens et al., "Translation inhibition in apoptosis: caspase-dependent PKR activation and eIF2—$\alpha$ phosphorylation," *J. Biol. Chem.*, 276: 41620-41628, 2001.

Sarkar et al., "mda-7 (IL-24) mediates selective apoptosis in human melanoma cells by inducing the coordinated overexpression of the GADD family of genes by means of p38 MAPK," *Proc. Natl. Acad. Sci., USA*, 99(15):10054-10059, 2002.

Sarkar, et al., "mda-7 (IL-24): signaling and functional roles," *Bio Techniques*, 33:S30-S39, 2002.

Schaefer et al., "Cutting Edge: FISP (IL-4-induced secreted protein), a novel cytokine-like molecule secreted by Th2 cells," *J. Immunol.*, 166:5859-5863, 2001.

Sedlak et al, "Multiple Bcl-2 family members demonstrate selective dimerizations with *bax*," *Proc. Nat'l. Acad. Sci. USA*, 92:7834-7838, 1995.

Shimizu et al., "Bcl-2 family proteins regulate the release of apoptogenic cytochrome c by the mitochondrial channel vdac," *Nature*, 399:483-487, 1999.

Shtrichman et al, "Tissue selectivity of interferon-stimulated gene expression in mice infected with dam$^+$versus dam$^-$*salmonella enterica* serovar typhimurium strains," *Infect Immun*, 70:5579-5588, 2002.

Skolnick and Fetrow, "From genes to protein structure and function: novel applications of computational approaches in the genomic era," *TIB Tech*, 18:34-39, 2000.

Solyanik et al., "Different growth patterns of a cancer cell population as a function of its starting growth characteristics: analysis by mathematical modeling," *Cell Prolif.*, 28:263-278, 1995.

Soo et al., "Cutaneous rat wounds express C49a, a novel gene with homology to the human melanoma differentiation associated gene, Mda-7," *J. Cell. Biochem*, 74:1-10, 1999.

Spitz et al., "Adenoviral-mediated wild-type p53 gene expression sensitizes colorectal cancer cells to ionizing radiation," *Clinical Cancer Research*, 2:1665-1671, 1996.

Stokke et al., "Uncoupling of the order of the S and M phases: effects of staurosporine on human cell cycle kinases," *Cell Prolif.*, 30(5):197-218, 1997.

Su et al., "A combinatorial approach for selectively inducing programmed cell death in human pancreatic cancer cells," *Proc. Natl. Acad. Sci., USA*, 98(18):10332-10337, 2001.

Su et al., "The cancer growth suppressor gene *mda-7* selectively induces apoptosis in human breast cancer cells and inhibits tumor growth in nude mice," *Proc. Nat'l Acad. Sci, USA*, 95: 14400-14405, 1998.

Sudhakar et al., "Phosphorylation of serine 51 in initiation factor $2\alpha$ (eIF2$\alpha$) promotes complex formation between eIF2$\alpha$(P) and eIF2B and causes inhibition in the guanine nucleotide exchange activity of eIF2B," *Biochemistry*, 39(42):12929-12938, 2000.

Tait, "HLA class I expression on human cancer cells," *Human Immunology*, 61:158-165, 2000.

Templeton et al., "Improved DNA: liposome complexes for increases systemic delivery and gene expression," *Nat. Biotechnol.*, 15:647-652, 1997.

Toyoshima and Hunter, "p27, a novel inhibitor of G1 cyclin-Cdk protein kinase activity, is related to p21," *Cell*, 78:67-74, 1994.

Tsuiki et al., "Mechanism of hyperploid cell formation induced by microtubule inhibiting drug in glioma cell lines," *Oncogene*, 20: 420-429, 2001.

Vattem et al., "Inhibitory sequences in the N-terminus of the double-stranded-RNA-dependent protein kinase, PKR, are important for regulating phosphorylation of eukaryotic initiation factor $2\alpha$ (eIF2$\alpha$)," *Eur J Biochem*, 268(4):1143-1153, 2001.

Verma and Somia, "Gene therapy promises, problems and prospects," *Nature*, 389:239-242, 1997.

Vieira et al., "Isolation and expression of human cytokine synthesis nhibitory factor complementary DNA clones homology to Epstein-Barr virus open reading frame BCRFI," *Proc. Natl. Acad. Sci., USA*, 88(4):1172-1176, 1991.

Vogelstein and Kinzler, "p53 function and dysfunction," *Cell*, 70:523-526, 1992.

Walther and Stein., "Viral vectors for gene transfer," *Drugs*, 60(2):249-271, 2000.

Wang et al., "Interleukin 24 (MDA-7/MOB-5) signals through two heterodimeric receptors, IL-22R1/IL-20R2 and IL-20R1/IL-20R2," *J Biol Chem*, 277: 7341-7347, 2002.

White, "Life, death, and the pursuit of apoptosis," *Genes Dev.*, 10:1-15, 1996.

Yeo et al., "Accumulation of unglycosylated liver secretory glycoproteins in the rough endoplasmic reticulum," *Biochem Biophys Res Commun*, 160(3):1421-1428, 1989.

Zamanian-Daryoush et al., "Cell cycle regulation of the double stranded RNA activated protein kinase, PKR," *Oncogene*, 18(2): 315-326, 1999.

Zhang et al., "Identification of a novel ligand-receptor pair constitutively activated by ras oncogenes," *J. Biol. Chem.*, 275:24436-24443, 2000.

U.S. Appl. No. 09/615,154, filed Jul. 13, 2000, Mhashilkar et al.

U.S. Appl. No. 60/661,680, filed Mar. 14, 2005, Lin et al.

Database UniProt, "Interleukin-24 precursor (suppression of tumorigenicity 16 protein) (melanoma differentiation-associated gene 7 protein) (MDA-7)," Accession No. Uniprot: Q13007, 2004.

Davis, "The many faces of epidermal growth factor repeats," *The New Biologist*, 2(5):410-419, 1990.

Denkert et al., "Prognostic impact of cyclooxygenase-2 in breast cancer," *Clin. Breast Cancer*, 4(6):428-433, 2004.

Dillman, "Perceptions of Herceptin: a monoclonal antibody for the treatment of breast cancer," *Cancer Biotherapy & Radiopharmaceuticals*, 14(1):5-10, 1999.

Donze et al., "The Hsp90 chaperone complex is both a facilitator and a repressor of the dsRNA-dependent kinase PKR," *EMBO J.*, 20:3771-3780, 2001.

Earnest et al., "Piroxicam and other cyclooxygenase inhibitors: potential for cancer chemoprevention," *J. Cell Biochem. Suppl.*, 161:156-166, 1992.

El-Rayes et al., "Cyclooxygenase-2-dependent and-independent effects of celecoxib in pancreatic cancer cell lines," *Mol. Cancer Ther.*, 3:1421-1426, 2004.

Fariss et al., "The selective antiproliferative effects of alpha-tocopheryl hemisuccinate and cholesteryl hemisuccinate on murine leukemia cells result from the action of the intact compounds," *Cancer Res.*, 54:3346-3351, 1994.

Fraley et al., "Entrapment of a bacterial plasmid in phospholipid vesicles: potential for gene transfer," *Proc. Natl. Acad. Sci USA*, 76:3348-3352, 1979.

Gann et al., "Low-dose aspirin and incidence of colorectal tumors in a randomized trial," *J. Natl. Cancer Inst.*, 85:1220-1224, 1993.

Garner et al, "Celecoxib for rheumatoid arthritis," *Cochrane Database Syst Rev.*, (4):CD003831, 2002. (abstract only).

Giovannucci et al., "Aspirin use and the risk for colorectal cancer and adenoma in male health professionals," *Ann. Intern. Med.*, 121:241-246, 1994.

Giovannucci et al., "Physical activity, obesity, and risk of colorectal adenoma in women (United States)," *Cancer Causes Control*, 7(2):253-63, 1996. (abstract only).

Greenberg et al., "Reduced risk of large-bowel adenomas among aspirin users. The Polyp Prevention Study Group," *J. Natl. Cancer Inst.*, 85:912-916, 1993.

Hanif et al., "Effects of nonsteroidal anti-inflammatory drugs on proliferation and on induction of apoptosis in colon cancer cells by a prostaglandin-independent pat," *Biochemical Pharmacology*, (52):237 245, 1996.

Howe et al., "Celecoxib, a selective cyclooxygenase 2 inhibitor, protects against human epidermal growth factor receptor 2 (HER-2)/neu-induced breast cancer," *Cancer Res.*, 62:5405-5407, 2002.

Howe et al., "Cyclooxygenase-2: a target for the prevention and treatment of breast cancer," *Endocr. Relat. Cancer*, 8:97-114, 2001.

Ji et al., "Expression of several genes in the human chromosome 3p21.3 homozygous deletion region by an adenovirus vector results in tumor suppressor activities in vitro and in vivo," *Cancer Research*, 62:2715-2720, 2002.

Kamal et al., "A high-affinity conformation of Hsp90 confers tumour selectivity on Hsp90 inhibitors, " *Nature.*,425:407-410, 2003.

Killary et al, "Definition of a tumor suppressor locus within human chromosome 3p21-p22," *Proc Nat Acad Sci USA*, 89:10877-10881, 1992.

Kismet et al., "Celecoxib: a potent cyclooxygenase-2 inhibitor in cancer prevention," *Cancer Detect Prev.*, 28(2):127-42, 2004.

Kline et al., "Vitamin E: mechanisms of action as tumor cell growth inhibitors, " In: *Proceeding of the International Conference on Nutrition and Cancer*, Prasad and Cole (Eds.), Amsterdam: IOS Press, 37-53, 1998.

Kline et al., "Vitamin E: mechanisms of action as tumor cell growth inhibitors, " *J. Nutr.*, 131: 161S-163S, 2001.

Koehne and Dubois, "COX-2 inhibition and colorectal cancer," *Semin. Oncol.*, 31(2 Suppl 7):12-21, 2004.

Kulp et al., "3-phosphoinositide-dependent protein kinase-1/Akt signaling represents a major cyclooxygenase-2-independent target for celecoxib in prostate cancer cells," *Cancer Res.*, 64:1444-1451, 2004.

Le et al., "Genes affecting the cell cycle, growth, maintenance, and drug sensitivity are preferentially regulated by anti-HER2 antibody through phosphatidylinositol 3-kinase-AKT signaling," *J. Biol. Chem.*, 280(3):2092-2104, 2005.

Leng et al., "Cyclooxygenase-2 promotes hepatocellular carcinoma cell growth through Akt activation: evidence for Akt inhibition in celecoxib-induced apoptosis," *Hepatology*, 38:756-768, 2003.

Lerman et al., "The 630-kb lung cancer homozygous deletion region on human chromosome 3p21.3: identification and evaluation of the resident candidate tumor suppressor genes. The International Lung Cancer Chromosome 3p21.3 Tumor Suppressor Gene Consortium," *Cancer Research*, 60:6116-6133, 2000.

Liu et al., "Combination of radiation and celebrex (celecoxib) reduce mammary and lung tumor growth," *Am. J. Clin. Oncol.*, 26:S103-109, 2003.

Lupulescu, "Control of precancer cell transformation into cancer cells: its relevance to cancer prevention," *Cancer Detect. Prev.*, 20(6):634-637, 1996.

Malafa and Neitzel, "Vitamin E succinate promotes breast cancer tumor dormancy," *J. Surg. Res.*, 93:163-170, 2000.

Malafa et al., "Vitamin E inhibits melanoma growth in mice," *Surgery*, 131:85-91, 2002.

Maloney and Workman, "HSP90 as a new therapeutic target for cancer therapy: the story unfolds," *Expert Opin. Biol. Ther.*, 2:3-24, 2002. (abstract only).

Mandler et al., "Modifications in synthesis strategy improve the yield and efficacy of geldanamycin-herceptin immunoconjugates," *Bioconjug. Chem.*, 13(4):786-791, 2002.

McKenzie et al., "Combination therapy of Ad-mda7 and trastuzumab increases cell death in Her-2/neu-overexpressing breast cancer cells," *Surgery*, 136:437-442, 2004.

Mizuguchi and Kay, "Efficient construction of a recombinant adenovirus vector by an improved in vitro ligation method," *Human Gene Therapy*, 9:2577-2583, 1998.

Narisawa et al., "Inhibition of development of methylnitrosourea-induced rat colon tumors by indomethacin treatment," *Cancer Res.*, 41(5):1954-1957, 1981.

Neckers et al., "Geldanamycin as a potential anti-cancer agent: its molecular target and biochemical activity," *Invest New Drugs*, 17:361-373, 1999.

Neuzil et al., "Selective cancer cell killing by α-tocopheryl succinate," *Br. J. Cancer*, 84:87-89, 2000.

Nicolau and Sene, "Liposome-mediated DNA transfer in eukaryotic cells. Dependence of the transfer efficiency upon the type of liposomes used and the host cell cycle stage," *Biochim. Biophys. Acta*, 721:185-190, 1982.

Nicolau et al., "Liposomes as carriers for in vivo gene transfer and expression," *Methods Enzymol.*, 149:157-176, 1987.

Nishisaka et al., "Immunotherapy and gene therapy for renal cell carcinoma," *Urol Oncol*, 3:148-153, 1997.

Piazza et al., "Antineoplastic drugs sulindac sulfide and sulfone inhibit cell growth by inducing apoptosis," *Cancer Res.*, 55(14):3110-6, 1995.

Piazza et al., "Apoptosis primarily accounts for the growth-inhibitory properties of sulindac metabolites and involves a mechanism that is independent of cyclooxygenase inhibition, cell cycle arrest, and p53 induction," *Cancer Res.*, (57):2452-59, 1997.

Piazza et al, "Sulindac sulfone inhibits azoxymethane-induced colon carcinogenesis in rats without reducing prostaglandin levels," *Cancer Res.*, (57):2909 2915, 1997.

Prasad and Edwards-Prasad, "Effects of tocopherol (vitamin E) acid succinate on morphological alterations and growth inhibition in melanoma cells in culture," *Cancer Res.*, 42:550-554, 1982.

Prasad and Edwards-Prasad, "Vitamin E and cancer prevention: recent advances and future potentials," *J. Am. Coll. Nutr.*, 11:487-500, 1992.

Ramesh et al, "Local and systemic inhibition of lung tumor growth after nanoparticle-mediated mda-7/IL-24 gene delivery," *DNA and Cell Blol*, 23:850-857, 2004.

Rao et al., "Chemoprevention of colon carcinogenesis by sulindac, a nonsteroidal anti-inflammatory agent," *Cancer Res.*, 55(7):1464-1472, 1995.

Reddy et al., "Chemoprevention of colon carcinogenesis by concurrent administration of piroxicam, a nonsteroidal antiinflammatory drug with D,L-alpha-difluoromethylornithine, an ornithine decarboxylase inhibitor, in diet," *Cancer Res.*, (50):2562-2568, 1990.

Ross et al., "The Her-2/neu gene and protein in breast cancer 2003: biomarker and target of therapy," *Oncologist*, 8(4):307-25, 2003.

Sausville et al., "Clinical development of 17-allylamino, 17-demethoxygeldanamycin," *Curr. Cancer Drug Targets*, 3:377-383, 2003.

Schaefer et al., "Observation of antigen-dependent CD8+ T-cell/dendritic cell interactions in vivo," *Cell Immunol.*, 214:110-122, 2001.

Schulte and Neckers, "The benzoquinone ansamycin 17-allylamino-17-demethoxygeldanamycin binds to HSP90 and shares important biologic activities with geldanamycin," *Cancer Chemother. Pharmacol.*, 42(4):273-279, 1998.

Schwartz and Shklar, "The selective cytotoxic effect of carotenoids and alpha-tocopherol on human cancer cell lines in vitro," *J. Oral Maxillofac. Surg.*, 50:367-373, 1992.

Singh and Lippman, "Cancer chemoprevention. Part 2: Hormones, nonclassic antioxidant natural agents, NSAIDs, and other agents," *Oncology (Williston Park)*, 12(12): 1787-800, 1998.

Singh and Reddy, Molecular markers in chemoprevention of colon cancer, *Annals. NY Acad Sci.*, (768):205-209, 1995.

Singh et al., "Modulation of azoxymethane-induced mutational activation of ras protooncogenes by chemopreventive agents in colon carcinogenesis," *Carcinogenesis*, (15):1317-1323, 1994.

Steinbach et al., "The effect of celecoxib, a cyclooxygenase-2 inhibitor, in familial adenomatous polyposis," *N. Engl. J. Med.*, 342:1946-1952, 2000.

Su et al., "Alterations in pancreatic, biliary, and breast carcinomas support MKK4 as a genetically targeted tumor suppressor gene," *Cancer Res.*, 58, 2339-2342, 1998.

Taylor and Kingston, "E1a transactivation of human HSP70 gene promoter substitution mutants is independent of the composition of upstream and TATA elements," *Mol. Cell. Biol.*, 10:176, 1990.

Taylor and Kingston, "Factor substitution in a human HSP70 gene promoter: TATA-dependent and TATA-independent interactions," *Mol. Cell. Biol.*, 10:165,1990.

Thompson et al., "Inhibition of mammary carcinogenesis in rats by sulfone metabolite of sulindac," *J. Natl. Cancer Inst.*, 87(16):1259-1260, 1995.

Thun et al., "Aspirin use and reduced risk of fatal colon cancer," *N. Engl. J. Med.*, 325(23):1593-1596, 1991.

Todd et al., "An 80 Kb P1 clone from chromosome 3p21.3 suppresses tumor growth in vivo," *Oncogene*, 13:2387-2396, 1996.

Tomizawa et al., "Inhibition of lung cancer cell growth and induction of apoptosis after reexpression of 3p21.3 candidate tumor suppressor gene SEMA3B," *P Nat Acad Sci USA*, 98:13954-13959, 2001.

Tong et al., "Immune activation by Ad-mda7 (INGN 241) gene transfer in advanced patients," *Cancer Gene Therapy*, 10:S37, 2002.

Whitesell et al., "Inhibition of heat shock protein HSP90-pp60v-src heteroprotein complex formation by benzoquinone ansamycins: essential role for stress proteins in oncogenic transformation," *Proc. Natl. Acad Sci. USA*, 91(18):8324-8328, 1994.

Williams, "Signal integration via PKR," *Sci STKE*, 89:RE2, 2001. (abstract only).

Wu et al., "Inhibitory effects of RRR-alpha-tocopheryl succinate on benzo(a)pyrene (B(a)P)-induced forestomach carcinogenesis in female mice," *World J. Gastroenterol.*, 7:60-65, 2001.

You et al., "Role of extracellular signal-regulated kinase pathway in RRR-alpha-tocopheryl succinate-induced differentiation of human MDA-MB-435 breast cancer cells," *Mol. Carcinogenesis*, 33(4):228-236, 2002.

You et al., "RRR-alpha-tocopheryl succinate induces MDA-MB-435 and MCF-7 human breast cancer cells to undergo differentiation," *Cell Growth Differ.*, 12:471-480, 2001.

Yu et al., "Activation of extracellular signal-regulated kinase and c-Jun-NH(2)-terminal kinase but not p38 mitogen-activated protein kinases is required for RRR-alpha-tocopheryl succinate-induced apoptosis of human breast cancer cells," *Cancer Res.*, 61(17):6569-6576, 2001.

Alshafie et al., "Chemotherapeutic evaluation of celecoxib, a cyclooxygenase-2 inhibitor, in a rat mammary tumor model," *Oncology Reports*, 7:1377-1381, 2000.

Harris et al., "Chemoprevention of breast cancer in rats by celecoxib, a cyclooxygenase 2 inhibitor," *Caplus*, Abstract No. 2000:282718, 2000.

Maniotis et al., "Vascular Channel Formation by Human Melanoma Cells in Vivo and in Vitro: Vasculogenic Mimicry," *Am. J. Pathology*, 155:739-752, 1999.

Pezzella et al., "Non-Small-Cell Lung Carcinoma Tumor Growth without Morphological Evidence of Neo-Angiogenesis," *Am. J. Pathology*, 151:1417-1423, 1997.

Sakariassen et al.,"Angiogenesis-independent tumor growth mediated by stem-like cancer cells," *Proc. Natl. Acad. Sci. USA*, 103:16466-16471, 2006.

Vermeulen et al., "Lack of angiogenesis in lymph node metastases of carcinomas is growth pattern-dependent," *Histopathology*, 40:105-107, 2002.

Bocangel et al., "Combinatorial synergy induced by adenoviral-mediated mda-7 and Herceptin in Her-2+ breast cancer cells," *Cancer Gene Therapy*, 1-11, 2006.

Chada et al., "mda-7 gene transfer sensitizes breast carcinoma cells to chemotherapy, biological therapies and radiotherapy: correlation with expression of bcl-2 family members," *Cancer Gene Therapy*, 1-13, 2005.

Emdad et al., "Ionizing Radiation Enhances Adenoviral Vector Expressing mda-7/IL-24-mediated Apoptosis in Human Ovarian Cancer," *J. Cell Physiol.*, 208:298-306, 2006.

Inoue et al., "MDA-7/IL-24-Based Cancer Gene Therapy: Translation from the Laboratory to the Clinic," *Current Gene Therapy*, 6:73-91, 2006.

Kawabe et al., "Adenovirus-Mediated mda-7 Gene Expression Radiosensitizes Non-Small Cell Lung Cancer Cells via TP53-Independent Mechanisms," *Molecular Therapy*, 6:637-644, 2002.

McKenzie et al., "Combination therapy of Ad-mda7 and trastuzumab increases cell death in Her-2/neu-overexpressing breast cancer cells," *Surgery*, 136:437-442, 2004.

Nishikawa et al., "Adenoviral-mediated mda-7 expression suppresses DNA repair capacity and radiosensitizes non-small-cell lung cancer cells," *Oncogene*, 23:7125-7131, 2004.

Nishikawa et al., "Adenovirus-Mediated mda-7 (IL24) Gene Therapy Suppresses Angiogenesis and Sensitizes NSCLC Xenograft Tumors to Radiation," *Mol. Therapy*, 9:818-828, 2004.

Su et al., "Ionizing radiation enhances therapeutic activity of mda-7/IL-24: overcoming radiation- and mda-7/IL-24-resistance in prostrate cancer cells overexpressing the antiapoptotic proteins bcl-xL or bcl-2," *Oncogene*, 25:2339-2348, 2006.

Chada et al., "mda-7/IL24 Kills Pancreatic Cancer Cells by Inhibition of the Wnt/PI3K Signaling Pathways: Identification of IL-20 Receptor-Mediated Bystander Activity against Pancreatic Cancer," *Mol. Ther.*, 11(5):724-733, 2005.

Inoue et al., "Inhibition of Src Kinase Activity by Ad-mda7 Suppresses Vascular Endothelial Growth Factor Expression in Prostate Carcinoma Cells," *Mol. Ther.*, 12:707-715, 2005.

Mellinghoff et al., "Molecular determinants of the response of glioblastomas to EGFR kinase inhibitors," *New Eng. J. Med.*, 353:2012-2024, 2006.

Normano et al., "The MEK/MAPK pathway is involved in the resistance of breast cancer cells to the EGFR tyrosine kinase inhibitor gefitinib," *J. Cell Physiol.*, 207:420-427, 2006.

Sutter et al., "Targeting the epidermal growth factor receptor by erlotinib (Tarceva) for the treatment of esophageal cancer," *Int. J. Cancer*, 118:1814-1822, 2006.

Xia et al., "A model of acquired autoresistance to a potent ErbB2 tyrosine kinase inhibitor and a therapeutic strategy to prevent its onset in breast cancer," *Proc. Natl. Acad. Sci. USA*, 103:7795-7800, 2006.

Ohara, "Radiotherapy: a significant treatment option in management of prostatic cancer," *Gan. To Kagakyu Ryoho.*, 25:823-828, 1998 (PubMed Abstract).

Ramesh et al., "MDA-7/IL-24 is a Novel Ligand that Regulates Angiogenesis via the IL-22 Receptor," *Cancer Gene Therapy*, 10:S03, 2002 (Abstract No. 008).

Alberts et al. "Do NSAIDs exert their colon cancer chemoprevention activities through the inhibition of mucosal prostaglandin synthetase," *J. Cell. Biochem. Supp.*, 22:18-23, 1995.

Barber, GN., "Host defense, viruses and apoptosis," *Cell Death Differ.*, 8(2):113-126, 2001.

Basu et al., "Cyclooxygenase-2 inhibitor induces apoptosis in breast cancer cells in an in vivo model of spontaneous metastatic breast cancer," *Mol. Cancer Res.*, 2:632-642, 2004.

Bedi et al., "Inhibition of apoptosis during development of colorectal cancer," *Cancer Res.*, 55(9):1811-1816, 1995.

Benoit et al., "Cardiac-specific transgenic overexpression of alpha1B-adrenergic receptors induce chronic activation of ERK MAPK signalling," *Biochem. Cell Biol.*, 82(6):719-727, 2004.

Benoit et al., "Regulation of HER-2 oncogene expression by cyclooxygenase-2 and prostaglandin E2," *Oncogene*, 23:1631-1635, 2004.

Bonvini et al., "Geldanamycin abrogates ErbB2 association with proteasome-resistant beta-catenin in melanoma cells, increases beta-catenin-E-cadherin association, and decreases beta-catenin-sensitive transcription," *Cancer Res.*, 61:1671-1677, 2001.

Chada et al. "The multifunctional mda-7 gene encodes both tumor suppressor and TH1 cytokine (IL-24) activities," *Cancer Gene Therapy*, 10:S3, 2003.

Chada et al., "Bystander activity of Ad-mda7: human MDA-7 protein kills melanoma cells via an IL-20 receptor-dependent but STAT3-independent mechanism," *Mol. Ther.*, 10(6):1085-1095, 2004.

Chada et al., "MDA-7/IL-24 is a unique cytokine—tumor suppressor in the IL-10 family," *Int. Immunopharmacol.*, 4:649-667, 2004.

Craven et al., "A decade of tyrosine kinases: from gene discovery to therapeutics," *Surg. Oncol.*, 12(1):39-49, 2003.

Daigo et al., "Molecular cloning of a candidate tumor suppressor gene, DLC1, from chromosome 3p21.3," *Cancer Research*, 59:1966-1972, 1999.

Database accession No. U70824, GenBank, (1998).

Database accession No. U70880, GenBank, (1998).

Gale et al., "Control of PKR protein kinase by hepatitis C virus nonstructural 5A protein: molecular mechanisms of kinas regulation," *Mol. Cell Biol.*, 18:5208-5218, 1998.

Gallagher et al., "Cloning, expression and initial characterisation of interleukin-19 (IL-19), a novel homologue of human interleukin-10 (IL-10)," *Genes Immun.* 1:442-450, 2000.

Garn et al., "IL-24 is expressed by rat and human macrophages," *Immunobiol*, 205:321-334, 2002.

Gazdar and Minna,"Targeted therapies for killing tumor cells," *Proc. Natl. Acad. Sci., USA*, 98(18):10028-10030, 2001.

GenBank Accession No. XM_001405, (2001).

Gertig and Hunter, "Genes and environment in the etiology of colorectal cancer," *Semin. Cancer Biol.*, 8(4):285-298, 1997.

Gething and Sambrook, "Protein folding in the cell," *Nature*, 355(6355):33-45, 1992.

Gil et al., "Induction of apoptosis by double-stranded-RNA-dependent protein kinase (PKR) involves the α subunit of eukaryotic translation initiation factor 2 and NF-κB," *Molecular and Cellular Biology*, 19(7):4653-4663, 1999.

Gliniak and Le, "Tumor necrosis factor-related apoptosis-inducing ligand's antitumor activity in vivo is enhanced by the chemotherapeutic agent CPT-11," *Cancer Res.* 59:6153-6158, 1999.

Goh et al, "The protein kinase PKR is required for p38 MAPK activation and the innate immune response to bacterial endotoxin," *EMBO J.*, 19(16):4292-4297, 2000.

Górecki, "Prospects and problems of gene therapy: an update," *Expert Opin. Emerging Drugs*, 6(2):187-198, 2001.

Haines et al., "Expression of the protein kinase p-68 recognized by the monoclonal antibody TJ4C4 in human lung neoplasms," *Virchows Arch. B. Cell Pathol.*, 62:151-158, 1992.

Han et al., "The E1B 19K protein blocks apoptosis by interacting with and inhibiting the p53-unducible and death-promoting Bax protein," *Genes Dev.*, 10(4):461-477, 1996.

Hanibuchi et al., "Therapeutic efficacy of mouse-human chimeric anti-ganglioside gm2 monoclonal antibody against multiple organ micrometastases of human lung cancer in NK cell-depleted scid mice," *Int. J. Cancer*, 78:480-485, 1998.

* cited by examiner

FIG. 1A
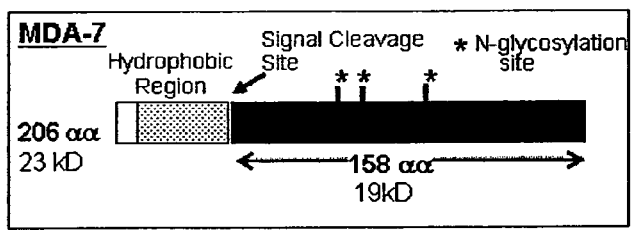
FIG. 1C
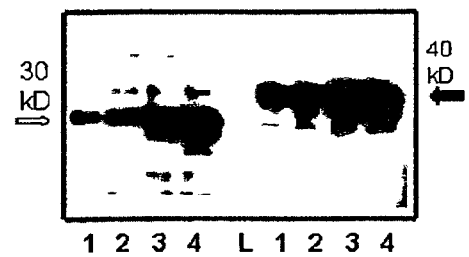
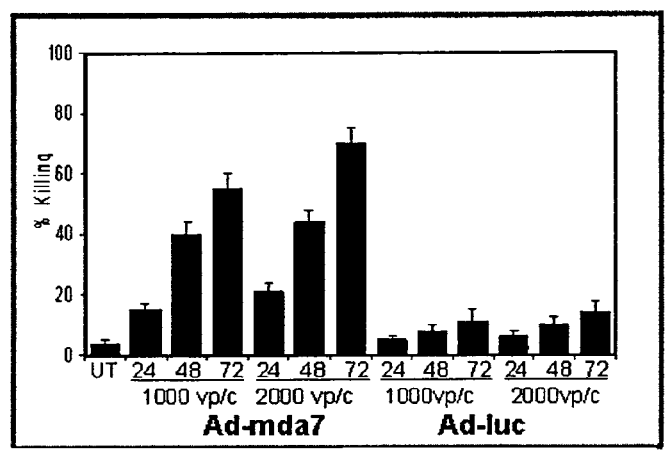
FIG. 1B

FIG. 2A
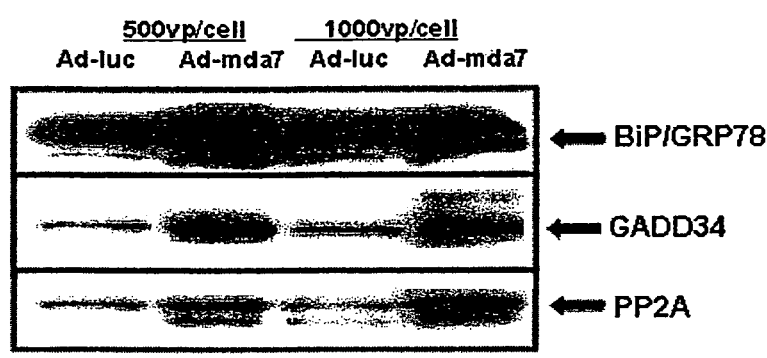
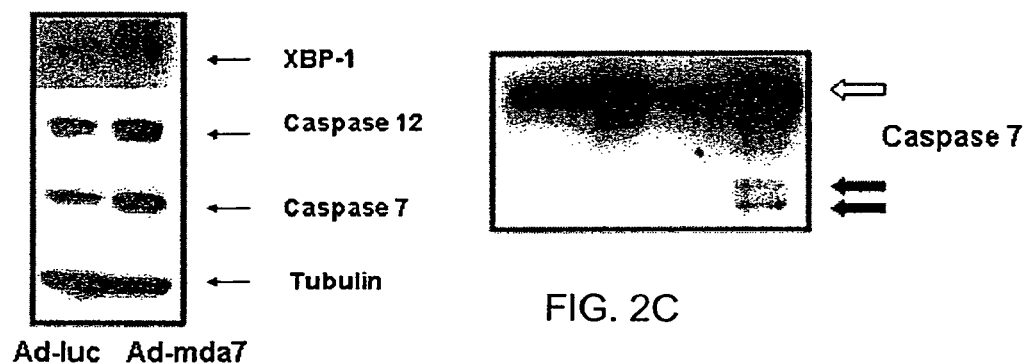
FIG. 2B
FIG. 2C

FIG. 7A
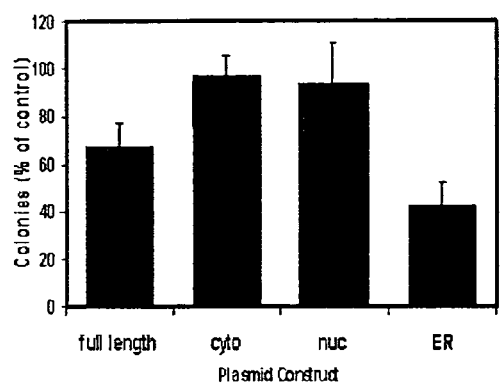
FIG. 7B
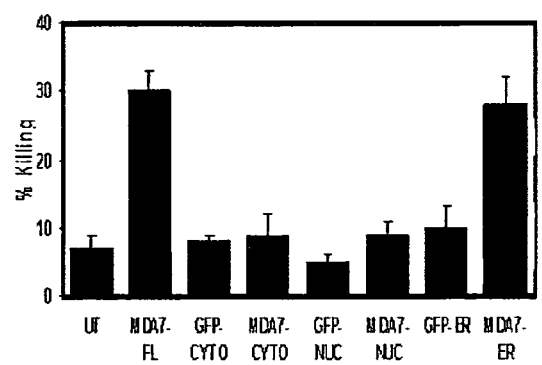
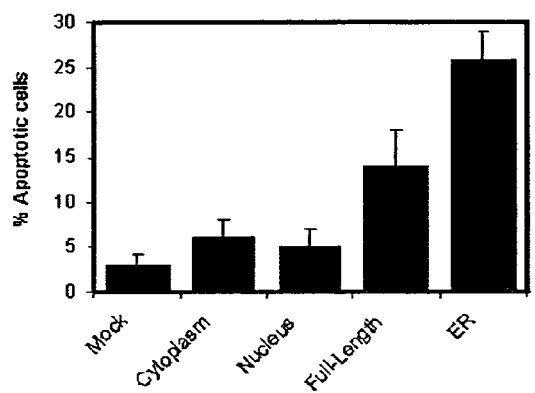
FIG. 7C

SEQUENCE LISTING

<160> NUMBER OF SEQ ID NOS: 7

<210> SEQ ID NO 1
<211> LENGTH: 718
<212> TYPE: DNA
<213> ORGANISM: Homo sapiens

<400> SEQUENCE: 1

```
acaagacatg actgtgatga ggagctgctt tcgccaattt aacaccaaga agaattgagg      60
ctgcttggga ggaaggccag gaggaacacg agactgagag atgaattttc aacagaggct     120
gcaaagcctg tggactttag ccagacccct ctgccctcct ttgctggcga cagcctctca     180
aatgcagatg gttgtgctcc cttgcctggg ttttaccctg cttctctgga gccaggtatc     240 agggcccag ggccaagaat tccactttgg gccctgccaa gtgaagggg ttgttcccca       300 gaaactgtgg gaagccttct gggctgtgaa agacactatg caagctcagg ataacatcac     360
gagtgcccgg ctgctgcagc aggaggttct gcagaacgtc tcggatgctg agagctgtta     420
ccttgtccac accctgctgg agttctactt gaaaactgtt ttcaaaaact accacaatag     480
aacagttgaa gtcaggactc tgaagtcatt ctctactctg ccaacaact tgttctcat      540 cgtgtcacaa ctgcaaccca gtcaagaaaa tgagatgttt tccatcagag acagtgcaca     600
caggcggttt ctgctattcc ggagagcatt caaacagttg gacgtagaag cagctctgac     660
caaagccctt ggggaagtgg acattcttct gacctggatg cagaaattct acaagctc      718
```

<210> SEQ ID NO 2
<211> LENGTH: 206
<212> TYPE: PRT
<213> ORGANISM: Homo sapiens

<400> SEQUENCE: 2

```
Met Asn Phe Gln Gln Arg Leu Gln Ser Leu Trp Thr Leu Ala Arg Pro
  1               5                  10                  15

Phe Cys Pro Pro Leu Leu Ala Thr Ala Ser Gln Met Gln Met Val Val
             20                  25                  30

Leu Pro Cys Leu Gly Phe Thr Leu Leu Leu Trp Ser Gln Val Ser Gly
         35                  40                  45

Ala Gln Gly Gln Glu Phe His Phe Gly Pro Cys Gln Val Lys Gly Val
     50                  55                  60

Val Pro Gln Lys Leu Trp Glu Ala Phe Trp Ala Val Lys Asp Thr Met
 65                  70                  75                  80

Gln Ala Gln Asp Asn Ile Thr Ser Ala Arg Leu Leu Gln Gln Glu Val
                 85                  90                  95

Leu Gln Asn Val Ser Asp Ala Glu Ser Cys Tyr Leu Val His Thr Leu
            100                 105                 110

Leu Glu Phe Tyr Leu Lys Thr Val Phe Lys Asn Tyr His Asn Arg Thr
        115                 120                 125
```

```
Val Glu Val Arg Thr Leu Lys Ser Phe Ser Thr Leu Ala Asn Asn Phe
    130                 135                 140

Val Leu Ile Val Ser Gln Leu Gln Pro Ser Gln Glu Asn Glu Met Phe
145                 150                 155                 160

Ser Ile Arg Asp Ser Ala His Arg Arg Phe Leu Leu Phe Arg Arg Ala
                165                 170                 175

Phe Lys Gln Leu Asp Val Glu Ala Ala Leu Thr Lys Ala Leu Gly Glu
            180                 185                 190

Val Asp Ile Leu Leu Thr Trp Met Gln Lys Phe Tyr Lys Leu
        195                 200                 205

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 3
ttttttgtcg acatggccca gggccaagaa ttcc                             34

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 4
ttttttgcgg ccgcgagctt gtagaatttc tgc                              33

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 5
cccgtaataa gcttggtacc g                                           21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 6
taaattggcg aaagcagctc                                             20

<210> SEQ ID NO 7
<211> LENGTH: 29
<212> TYPE: DNA
<213> ORGANISM: Artificial Sequence
<220> FEATURE:
```

```
<223> OTHER INFORMATION: Description of Artificial Sequence:
      Synthetic Primer

<400> SEQUENCE: 7
tggaattcgg cttacaagac atgactgtg                                              29
```

USE OF MDA-7 TO INHIBIT PATHOGENIC INFECTIOUS ORGANISMS

This application claims the benefit of the filing date of U.S. provisional patent application Ser. No. 60/526,031, filed Dec. 1, 2003, the entire contents of which are hereby incorporated by reference.

BACKGROUND OF THE INVENTION

1. Field of the Invention

The present invention relates generally to the fields of molecular biology, infectious diseases, and pharmacology. More particularly, it concerns methods of suppressing or preventing an infection of a subject or a cell by a pathogen using an MDA-7 polypeptide or a nucleic acid encoding an MDA-7 polypeptide.

2. Description of Related Art

Infections by pathogens are a major cause of morbidity and mortality in the U.S., and throughout the world. Successful vaccination programs against smallpox and polio, between 1950 and 1970, led to a general view by public health authorities, particularly in the West, that the war against infectious diseases was effectively over and some countries scaled-back health measures. However, the emergence of HIV and multi-resistant organisms has shown that constant vigilance is needed where pathogens are concerned.

In addition, in light of the events of Sep. 11, 2001, many anti-terrorist experts and government officials believe that the prospect of a bioterrorism attack against the United States using pathogens is highly likely. For example, terrorists may have the ability of gaining access to pathogens that are associated with substantial morbidity and mortality. Large scale release of a highly infectious pathogenic agent could infect the inhabitants of targeted cities and other areas. The attacks could result in long- and short-term health consequences and possibly death. Thus, in addition to the continuing need for the possibility of mass treatment of pathogens, there is an urgent need to develop strategies to prevent the morbidity and mortality associated with a bioterrorist attack wherein the public is exposed to deadly pathogens.

Viruses pose the threat of inflicting serious morbidity and mortality on the population. As obligate intracellular parasites, viruses rely exclusively on the translational machinery of the host cell for the synthesis of viral proteins. This relationship has imposed numerous challenges on both the infecting virus and the host cell. Importantly, viruses must compete with the endogenous transcripts of the host cell for the translation of viral mRNA. Eukaryotic viruses have evolved diverse mechanisms to ensure translational efficiency of viral mRNA above and beyond that of cellular RNA. These mechanisms serve to redirect the translational apparatus to favor viral transcripts, and they often come at the expense of the host cell.

One such mechanism whereby viruses ensure translational efficiency involves the cellular kinase known as interferon-induced, double-stranded (ds) RNA-activated serine/threonine protein kinase (PKR). PKR is involved in the regulated of apoptosis, cell-proliferation, signal transduction, and differentiation of cells. PKR is believed to localize in the cytoplasm and nucleolus of the cell, and associates with ribosomes. Overexpression or activation of PKR in HeLa, COS-1, U937, and NIH-3T3 cells has been shown to lead to apoptosis. In addition, mouse embryo fibroblasts from PKR knock-out mice are resistant to apoptotic cell death in response to dsRNA, tumor necrosis factor, and lipopolysaccharide. RNaseL and PKR mediate the IFN-induced antiviral response of the host, which is required to limit viral protein synthesis and pathogenesis. As part of the innate immune response to viral infection, RNaseL and PKR are activated by dsRNAs produced as intermediates in viral replication.

PKR also mediates the antiviral actions of interferon, in part by phosphorylating the alpha subunit of eukaryotic initiation factor 2 (eIF-2α), resulting in acute inhibition of mRNA translation and a concomitant block in viral replication (Merrick and Hershey, 1996; Meurs et al., 1990). In addition, PKR facilitates IFN-induced transcriptional programs by participating in the activation of nuclear factor kappa B and INF-regulatory factor 1 (Kumar et al., 1997).

Many viruses inhibit PKR activity. One such example is Hepatitis C virus (HCV), a member of the Flaviviridae, which mediates persistent infection within a majority of infected individuals. Many strains of HCV are resistant to alpha interferon (IFN) therapy. It has recently been shown that HCV represses PKR function through the actions of the viral NS5A protein, which binds and inhibits PKR in vivo (Gale et al., 1998, Gale et al., 1999). Other examples of viruses that inhibit PKR activity include adenovirus, EBV, poxvirus, influenza virus, reovirus, HIV, polio, HSV, and SV40 (Gale et al., 2000). Inhibition of PKR results in inhibition of apoptosis, with resulting continued translation of viral proteins.

Another cellular regulatory mechanism involved in protecting against viral infection involves the PRK-like endoplasmic-reticulum (ER)-resident kinase (PERK). PERK is a type I transmembrane protein that attenuates protein synthesis during endoplasmic reticulum (ER) stress by phosphorylating serine 51 on eIF2α. The HCV envelope protein, E2, can serve as a pseudosubstrate inhibitor of PERK and a potential viral regulator of the ER stress response (Pavio et al., 2003).

Another mediator of ER stress is the Unfolded Protein Response (UPR) (Gething and Sambrook, 1992). The UPR is an ER-to-nucleus signal transduction pathway that regulates a wide variety of target genes and is responsible for maintaining cellular homeostasis. Transient stresses such as glucose deprivation or perturbation of calcium or redox homeostasis can result in transient inhibition of protein translation and growth arrest. Prolonged UPR activation leads to activation of death-related signaling pathways and ultimately, to apoptotic death (Kaufman, 2002; Ron, 2002). The UPR is used by many endoplasmic reticulum-tropic viruses, such as HCV, flaviviruses, HHV6, rubella, LCMV, HIV, and Hepatitis B virus (HBV), to facilitate their life cycle and pathogenesis. Note that many viruses, especially positive strand viruses, modify host intracellular membranes to create a suitable compartment for viral replication—this requirement for virus-induced intracellular membrane production results in activation of UPR.

It is clear that pathogens other than viruses can activate the PKR and UPR defense systems. For example, PKR is activated in response to Salmonella infection (Shtrichman et al., 2002). Shtrichman et al. (2002) describes tissue-selectivity of interferon-stimulated gene expression in mice infected with Dam (+) versus Dam (−) Salmonella enterica serovar Typhimurium strains. In addition, the UPR serves as a defense system in plants (Oh et al., 2003). Oh et al. (2003) have shown conservation between animals and plants of the cis-activating element involved in the UPR.

The intracellular mediators, IRE1 and PERK are activated by ER stress, which can be induced by high-level glycoprotein expression. All enveloped viruses produce excess glycoproteins that could elicit PERK and IRE1 activation to meet the need for increased folding and secretory capacity. Thus, UPR activation is a common feature of viral replication.

Therefore, there is the need for novel agents that can be applied in the prevention and treatment of infections of subjects by viruses and other pathogens. Such novel methods may target not only immunostimulation, but may also be directed at interfering with viral replication through activation of PKR and the UPR response. These agents can be applied in ameliorating the effects of bioterrorism attacks wherein the public is exposed to pathogens.

SUMMARY OF THE INVENTION

Melanoma differentiation associated gene-7 (mda7) is a tumor suppressor gene. Numerous studies have documented the growth suppression effected by elevated expression of MDA-7 protein in various types of cancer cells (reviewed in Fisher et al., 2003).

The inventors have discovered that MDA-7 functions in a manner that involves certain pathways in cancer cells that are involved in pathogen infection and pathogen replication. The inventors propose to exploit these properties of MDA-7 by applying MDA-7 to the suppression and prevention of infections by viruses and other pathogens.

In addition, the inventors have discovered that Ad-mda7 transduction of lung cancer cells results in activation of the UPR. It has been discovered that MDA-7 expression in the ER elicited potent cell death in tumor cells and thus it appears necessary for MDA-7 to enter the secretory pathway to be effective in inducing apoptosis. In view of the fact that the UPR is exploited by viruses, these findings further support the inventors' discovery that MDA-7 can be applied in the prevention and treatment of infections of subjects by pathogens.

Certain embodiments of the present invention are generally concerned with methods of suppressing or preventing an infection of a subject by a pathogen, that involve administering to the subject a composition that includes: (a) a therapeutically effective amount of an MDA-7 polypeptide or a nucleic acid encoding the MDA-7 polypeptide; and (b) a pharmaceutically acceptable preparation suitable for delivery to said subject, wherein the MDA-7 suppresses or prevents the infection.

A pathogen is defined herein to include any living microorganism that can cause disease or dysfunction in a cell or subject. The methods of the present invention contemplate any type of pathogen. For example, the pathogen may be a bacterium, virus, fungus, protozoan, or helminth. One of ordinary skill in the art would be familiar with the variety of pathogens that are known to exist.

Any bacterium is contemplated for inclusion as a pathogen. For example, the pathogen may be a gram negative bacterium, a gram positive bacterium, or a bacterium for which gram staining is not applicable.

In certain embodiments of the present invention, the bacterium is a *Pneumococcus* species, *Streptococcus* species, *Enterococcus* species, *Staphylococcus* species, *Hemophilus* species, *Pseudomonas* species, *Brucella* species, *Bordetella pertussis*, *Neisseria* species, *Moraxella catarrhalis*, *Corynebacterium* species, *Listeria monocytogenes*, *Nocardia asteroides*, *Bacteroides* species, *Leptospira* species, *Klebsiella pneumoniae*, *Escherichia coli*, *Proteus* species, *Serratia* species, *Acinetobacter* species, *Yersinia pestis*, *Francisella tularensis*, *Enterobacter* species, *Helicobacter* species, *Legionella* species, *Shigella* species, *Mycobacterium* species, *Bacillus* species, or *Yersinia* species.

The species of *Streptococcus* may, for example, be *S. pyogenes*, *S. agalactiae*, *S. equi*, *S. canis*, *S. bovis*, *S. equinus*, *S. anginosus*, *S. sanguis*, *S. salivarius*, *S. mitis*, *S. mutans*, viridans streptococci, or peptostreptococci. The species of *Enterococcus* may be *Enterococcus faecalis* or *Enterococcus faecium*. The species of *Staphylococcus* may be, for example, *Staphylococcus epidermidis* or *Staphylococcus aureus*. The species of *Pseudomonas* may be *Pseudomonas aeruginosa*, *Pseudomonas pseudomallei*, or *Pseudomonas mallei*. The species of *Brucella* may be *Brucella melitensis*, *Brucella suis*, or *Brucella abortus*. The species of *Neisseria* may be may be *Corynebacterium diphtheriae*, *Corynebacterium ulcerans*, *Corynebacterium pseudotuberculosis*, *Corynebacterium pseudodiphtheriticum*, *Corynebacterium urealyticum*, *Corynebacterium hemolyticum*, or *Corynebacterium equi*. The species of *Mycobacterium* may be *M. tuberculosis*, *M. bovis*, *M. avium complex*, *M. marinum*, *M. fortuitum*, or *M. kansaii*. The species of *Bacillus* may be *B. cereus*, *B. thuringiensis*, or *B. anthracis*. The species of *Yersinia* may be *Y. pestis*, *Y. enterocolitica*, or *Y. pseudotuberculosis*.

Any type of virus is encompassed within the definition of pathogen. For example, in some embodiments, the virus is an endoplasmic reticulum-tropic virus. Examples of endoplasmic reticulum-tropic viruses include Hepatitis C virus, a flavivirus species, HHV6, rubella, LCMV, HIV, and Hepatitis B virus. In other embodiments, for example, the virus is influenza A, influenza B, influenza C, parainfluenza, paramyxoviruses, Newcastle disease virus, respiratory syncytial virus, measles, mumps, adenoviruses, adenoassociated viruses, parvoviruses, Epstein-Barr virus, rhinoviruses, coxsackieviruses, echoviruses, reoviruses, rhabdoviruses, coronavirus, polioviruses, herpes simplex virus, cytomegaloviruses, papillomaviruses, virus B, varicella-zoster, poxviruses, rabies, picomaviruses, rotavirus, or Kaposi associated herpesvirus. The definition of pathogen also encompasses fungi. Any fungus is contemplated for inclusion in the definition of pathogen, as long as it meets the definition of being a pathogen. For example, in some embodiments, the fungus is a *Absidia* species, *Actinomadura madurae*, *Actinomyces* species, *Allescheria boydii*, *Alternaria* species, *Anthopsis deltoidea*, *Apophysomyces elegans*, *Arnium leoporinum*, *Aspergillus* species, *Aureobasidium pullulans*, *Basidiobolus ranarum*, *Bipolaris* species, *Blastomyces dermatitidis*, *Candida* species, *Cephalosporium* species, *Chaetoconidium* species, *Chaetomium* species, *Cladosporium* species, *Coccidioides immitis*, *Conidiobolus* species, *Corynebacterium tenuis*, *Cryptococcus* species, *Cunninghamella bertholletiae*, *Curvularia* species, *Dactylaria* species, *Epidermophyton* species, *Epidermophyton floccosum*, *Exserophilum* species, *Exophiala* species, *Fonsecaea* species, *Fusarium* species, *Geotrichum* species, *Helminthosporium* species, *Histoplasma* species, *Lecythophora* species, *Madurella* species, *Malassezia furfur*, *Microsporum* species, *Mucor* species, *Mycocentrospora acerina*, *Nocardia* species, *Paracoccidioides brasiliensis*, *Penicillium* species, *Phaeosclera dematioides*, *Phaeoannellomyces* species, *Phialemonium obovatum*, *Phialophora* species, *Phoma* species, *Piedraia hortai*, *Pneumocystis carinii*, *Pythium insidiosum*, *Rhinocladiella aquaspersa*, *Rhizomucor pusillus*, *Rhizopus* species, *Saksenaea vasiformis*, *Sarcinomyces phaeomuriformis*, *Sporothrix schenckii*, *Syncephalastrum racemosum*, *Taeniolella boppii*, *Torulopsosis* species, *Trichophyton* species, *Trichosporon* species, *Ulocladium chartarum*, *Wangiella dermatitidis*, *Xylohypha* species, *Zygomyetes* species, *Thermomucor indicae-seudaticae*, or a *Radiomyces* species.

Pathogens may also include protozoans or helminths, such as *Cryptosporidium*, *Entamoeba*, *Plasmodium*, *Giardia*, *Leishmania*, *Trypanasoma*, *Trichomonas*, *Naegleria*, *Isospora belli*, *Toxoplasma gondii*, *Trichomonas vaginalis*, *Wunchereria*, *Ascaris*, *Schistosoma* species, *Cyclospora* species, or *Chlamydia* species.

The methods of the present invention contemplate any type of subject. For example, the subject may be a mammal. In certain embodiments, the mammal is a human.

Any method of administration of the composition is completed by the present invention. Methods of administration are discussed further in the specification below. In some embodiments, administering involves providing to the subject an expression cassette that includes a promoter, active in the subject, operably linked to a polynucleotide encoding an MDA-7 polypeptide.

In some embodiments, the expression cassette is carried in a viral vector. For example, the viral vector may be an adenoviral vector, a retroviral vector, a vaccinia viral vector, an adeno-associated viral vector, or a poxviral vector. In certain particular embodiments, the viral vector is an adenoviral vector.

In other embodiments, the expression cassette is carried in a nonviral vector. For example, the nonviral vector may include a lipid, such as a liposome.

Any MDA-7 polypeptide or nucleic acid encoding an MDA-7 polypeptide is contemplated for inclusion in the methods of the present invention. MDA-7 polypeptides and polynucleotides encoding an MDA-7 polypeptide is discussed further in the specification below. In certain embodiments, the MDA-7 polypeptide includes amino acids 49 to 206 of SEQ ID NO: 2. In certain other embodiments, the MDA-7 polypeptide includes a sequence of SEQ ID NO: 2.

Any pharmaceutically acceptable preparation suitable for delivery to the subject is contemplated for inclusion in the present invention. One of ordinary skill in the art would be familiar with the many types of preparations that can be formulated. Examples are discussed further in the specification below. For example, in some embodiments, the composition is formulated for oral administration, topical administration, intralesional injection, or intravenous administration.

In other embodiments of the present invention, the method involves the additional administration of at least one additional agent to prevent or suppress the infection in the subject. The administration of any one or more additional agent to prevent or suppress the infection is contemplated by the present invention. Examples of such agents are discussed further in the specification below.

Certain other embodiments of the present invention are generally concerned with methods of suppressing or preventing a viral infection of a cell, that involve obtaining an MDA-7 polypeptide or a nucleic acid encoding the MDA-7 polypeptide; and contacting the cell with the MDA-7 polypeptide or the nucleic acid encoding the MDA-7 polypeptide, wherein the MDA-7 suppresses or prevents infection of the cell.

The viral infection may be caused by any type of virus. For example, the viral infection may be caused by an oncogenic virus or an endoplasmic reticulum-tropic virus. For example, the endoplasmic reticulum-tropic virus may be Hepatitis C virus, a flavivirus species, HHV6, rubella, LCMV, HIV, or Hepatitis B virus.

Other examples of viruses which may cause the viral infection include influenza A, influenza B, influenza C, parainfluenza, paramyxoviruses, Newcastle disease virus, respiratory syncytial virus, measles, mumps, adenoviruses, adenoassociated viruses, parvoviruses, Epstein-Barr virus, rhinoviruses, coxsackieviruses, echoviruses, reoviruses, rhabdoviruses, coronavirus, polioviruses, herpes simplex virus, cytomegaloviruses, papillomaviruses, virus B, varicella-zoster, poxviruses, rabies, picornaviruses, rotavirus, or Kaposi associated herpes virus.

Any cell is contemplated for inclusion in the methods of the present invention. For example, in certain embodiments the cell is a mammalian cell, such as a human cell. In other embodiments, the cell is a cancer cell.

As with the methods discussed above, the MDA-7 polypeptide or nucleic acid encoding the MDA-7 polypeptide may include an expression cassette comprising a promoter, active in the cell, operably linked to a polynucleotide encoding an MDA-7 polypeptide. The parameters pertaining to expression cassettes discussed above also apply to these methods. For example, the expression cassette may be carried in a viral vector. Viral vectors are discussed further in the specification below.

The viral vector may, for example, be an adenoviral vector, a retroviral vector, a vaccinia viral vector, an adeno-associated viral vector, or a poxviral vector. In other embodiments, the expression cassette is carried in a non-viral vector. The nonviral vector may include, for example, a lipid.

MDA-7 polypeptides and polynucleotides encoding MDA-7 polypeptides have been previously discussed, and are discussed further in the specification below. For example, the MDA-7 polypeptide may include a sequence of SEQ ID NO: 2.

In other embodiments, the methods of the present invention may further include administering at least one additional agent to prevent or suppress the viral infection in the cell. One of ordinary skill in the art would be familiar with the numerous agents that are available to prevent or suppress viral infection in a cell.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A, FIG. 1B, FIG. 1C. MDA-7 kills lung tumor cells and is secreted.

FIG. 1A: Schematic of the MDA-7 protein. The large signal sequence (amino-acids 1-48), hydrophobic region (stippled), putative cleavage site (arrow) and potential N-glycosylation sites (*) are indicated. FIG. 1B: Ad-mda7 potently kills lung tumor cells. H1299 cells were treated with increasing doses (vp/cell) of Ad-mda7 or Ad-luc and analyzed at the indicated times for cell killing. Ad-mda7 causes a dose- and time-dependent loss of viability compared to Ad-luc. Results are shown as means±SD of triplicate samples. FIG. 1C: MDA-7 is secreted from H1299 cells. H1299 cells were transduced with 1000 vp/cell of Ad-mda7 or Ad-luc (middle lane, L) and cell lysates (left; days 1-4) and supernatants (right; days 1-4) analyzed by western blot using anti-MDA-7 antibody. The intracellular MDA-7 protein is shown by open arrow and secreted MDA-7 indicated by filled arrow.

FIG. 2A, FIG. 2B, FIG. 2C: Ad-mda7 activates Unfolded Protein Response Pathway (UPR) proteins. H1299 cells were treated with Ad-luc or Ad-mda7 and 48 hr later cell lysates were analyzed by western blot for stress protein expression. FIG. 2A: Cell lysates were analyzed for expression of BiP, GADD34 and PP2A. FIG. 2B: Cell lysates from Ad-luc and Ad-mda7 (1000 vp/cell) treated cells were analyzed for expression of caspase 7, caspase 12, XBP-1 and alpha-tubulin. FIG. 2C: Cell lysates from Ad-luc (lanes 1 and 3) and Ad-mda7 (lanes 2 and 4) treated H1299 cells (500 vp/cell and 1000 vp/cell) were immunoblotted and probed with anti-caspase 7. Pro-caspase 7 is shown with open arrow and cleavage products are shown with filled arrows.

FIG. 3A: Secreted MDA-7 protein is heavily glycosylated. MDA-7 supernatant samples were untreated (−) or treated (+) with glycopeptidase F and then evaluated by western blot using anti-MDA-7 antibody. Glyco F treatment significantly reduces the molecular weight of the MDA-7 protein. FIG. 3B: H1299 cells were transduced with Ad-mda7 in the presence of secretion inhibitors, Tunicamycin A (TUN) or Brefeldin A (BFA) and cell lysates (L) and supernatants (SN) analyzed by western blot using anti-MDA-7 antibody. Both BFA and TUN block secretion of MDA-7 (filled arrow) and result in buildup of intracellular MDA-7 (open arrows). Note the blot was over-exposed to illustrate inhibition of MDA-7 secretion.

FIG. 4A: H1299 cells were treated with Ad-mda7 (M), Ad-luc (L) or Ad-endostain (E) in the presence or absence of Brefeldin A (BFA; upper panel) or tunicamycin (TUN; lower panel) and cell viability assessed. Data are shown as mean+SD of triplicate samples. FIG. 4B: Intracellular MDA-7 kills H1299 cells. Supernatant from 293-mda7 cells (M) was applied to H1299 cells at 10 and 100 ng/ml and cell viability monitored after 3 days. MDA-7 protein prepared from $E.\ coli$ (EM; 20-100 ng/ml) and from baculovirus cultures (BacM; 100 ng/ml) were evaluated for cell toxicity. Ad-mda7 and Ad-luc (2000 vp/cell) were included as controls. Ad-mda7 induced cell killing which was not inhibited by addition of neutralizing anti-MDA-7 antibody. MDA-7 supernatant did not induce cell death. Data are shown as mean+SD of triplicate samples.

FIG. 6A: Subcellular localization of targeted MDA-7 proteins. H1299 cells were transiently transfected with the indicated plasmid or Ad vectors and 48 hr later, cells were fixed and immunostained for MDA-7 expression using anti-MDA-7 antibody. The re-targeted proteins demonstrate appropriate subcellular localization. FIG. 6B: Protein expression and secretion by re-targeted MDA-7 proteins. H1299 cells were transiently transfected with the indicated plasmid or Ad vectors and 48 hr later, cell lysates and supernatants were analyzed for MDA-7 expression by western blot. The upper panel shows results from supernatants (filled arrow) and the lower panel indicates MDA-7 expression from cell lysates (open arrows). MDA-7 is only secreted from full length and Ad-mda7 treated cells. Arrows indicate size of MDA-7 proteins produced by Ad-mda7 treated H1299 cells. Note FL MDA-7 bands are increased by 4 kD due to myc tag. FIG. 6C: H1299 cells were transiently transfected with targeting plasmids and analyzed for cell viability using the Live/Dead assay. Green fluorescence indicates viable cells and red fluorescence indicates dead cells (mag. ×100). Only FL and ER-targeted plasmids induce cell death. Ad-mda7 and Ad-luc (2000 vp/cell) are shown as controls (mag. X40).

FIG. 7A, FIG. 7B, FIG. 7C, FIG. 7D. MDA-7 must be in secretory pathway to induce apoptosis. FIG. 7A: PC-3 cells were transfected with the indicated plasmids mixed with pSV2neo and colony formation assays performed. After 14 days the numbers of colonies were assessed and compared to control pSV2neo transfection. Data indicate mean+SD of triplicate samples. Similar results were seen with H1299, A549, 293 and MCF-7 cells. FIG. 7B: H1299 cells were transiently transfected with the indicated plasmids and 3 days later assessed for cell viability using a trypan blue assay. Data indicate mean+SD of triplicate samples. Only FL and ER targeted MDA-7 elicit cell killing. FIG. 7C: H1299 cells were transiently transfected with the indicated plasmids and 48 hr later assessed for apoptosis by Hoescht staining. Data indicate mean+SD of triplicate samples. FIG. 7D: H1299 cells were transiently transfected with the indicated plasmids or Ad-mda7 or Ad-luc and 48 hr later, lysates immunoblotted and probed with anti-BiP and anti-alpha-tubulin antibodies. BiP is induced by full length and ER-targeted MDA-7.

FIG. 8A: INGN 241 injection elicits high level of MDA-7 expression and apoptosis induction. Samples from injection site (center and periphery of tumors were evaluated for MDA-7 immunostaining (n=10) and apoptosis via TUNEL staining (n=9). Pre-treatment MDA-7 staining was uniformly negative, whereas TUNEL signal averaged 5.6% in pre-treatment samples. Average MDA-7 staining was 52% at the injection site and 14% at the periphery of tumors. Apoptosis signals averaged 45% at the injection site and 15% at the periphery. FIG. 8B: High levels of transgene expression and apoptosis are transient. Pre-treatment and injection site sections were analyzed for MDA-7 immunostaining or apoptosis by TUNEL assay and median values plotted. MDA-7 immunostaining correlated with TUNEL reactivity and peaked at day 4 post-injection. Day 1 (n=5 patients); day 2 (n=3); day 4 (n=2); day 30 (n=7). By day 30, MDA-7 staining and apoptosis were undetectable.

DESCRIPTION OF ILLUSTRATIVE EMBODIMENTS

Figures 3A, 3B:
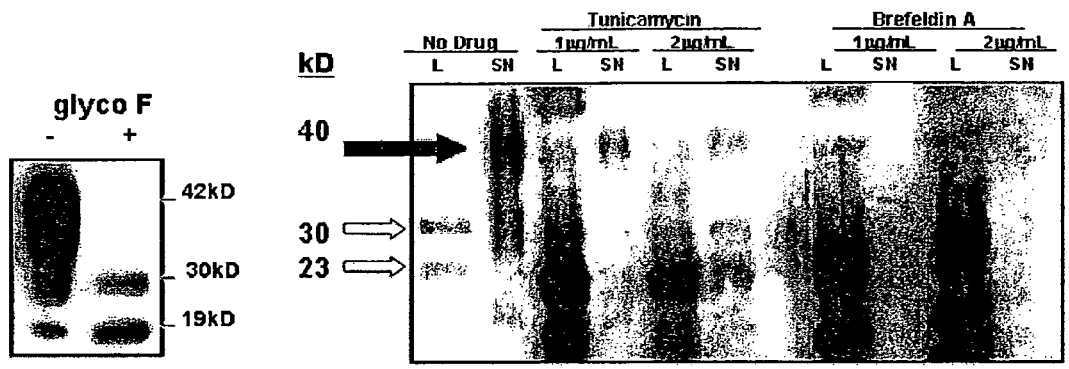
FIG. 3A, FIG. 3B. MDA-7 is secreted.

Melanoma differentiation associated gene-7 (mda-7) is a tumor suppressor gene. Numerous studies have documented the growth suppression effected by elevated expression of MDA-7 protein in various types of cancer cells (reviewed in Fisher et al., 2003). MDA-7 over-expression in normal cells, however, lacks the cytotoxic effects seen in cancer cells (Mhashilkar et al., 2001; Lebedeva et al., 2003).

Although primarily studied in the context of its tumor suppressor activity, MDA-7 has other activities. For instance, it has potent anti-angiogenic activity. In particular, the anti-angiogenic activity of MDA-7 is 50-fold more potent than endostatin. It has also been shown to have substantial pro-apoptotic activity.

MDA-7 has also been shown to exhibit immunostimulatory activity against cancer cells. Its immunosuppressive function includes potent inhibition of proinflammatory cytokine synthesis, including the inhibition of synthesis of IFN-γ, TNF-α, and IL-6 (De Waal Malefyt et al., 1991). MDA-7 has also been found to induce secretion of high levels of IL-6, TNF-α, and IFN-γ from human PBMC as measured by ELISA (Caudell et al., 2002).

Based upon its chromosomal localization in the IL-10 family cluster and its limited amino-acid identity to IL-10, mda-7 has now been designated as IL-24, and recent data indicate that this molecule functions as a pro-Th1 cytokine in human PBMC (Caudell et al., 2002). Further studies have demonstrated expression of mda-7 mRNA and MDA-7 protein in immune cells (Huang et al., 2001; Caudell et al., 2002). Thus mda-7 is an unusual pro-Th1 cytokine with pro-apoptotic activity.

Ad-mda 7 has been shown to induce and activate PKR in cancer cells, which leads to phosphorylation of the eIF-2α and the induction of apoptosis (Pataer et al., 2002). Treatment with 2-aminopurine (2-AP), a serine/threonine kinase inhibitor, inhibits PKR activation, eIF-2α phosphorylation, and apoptosis induction by Ad-mda7. Additionally, PKR null but not wild-type fibroblasts are resistant to Ad-mda7-induced apoptosis. Mouse embryo fibroblasts from PKR knockout mice are resistant to Ad-mda7-induced apoptosis (Pataer et al., 2002)]. In addition, immunofluorescence studies demonstrate that MDA-7 colocalizes with endogenous PKR protein, further indicating that MDA-7 is a substrate for PKR. These results suggest that the activation of PKR and its downstream targets may be a critical pathway for Ad-mda7-mediated apoptosis in cancer cells.

The inventors have discovered that MDA-7 functions in a manner that involves certain pathways in cancer cells that are involved in pathogen infection and replication. However, MDA-7 has never been contemplated for use as a therapeutic agent against infections by viruses and other pathogens. The inventors propose to exploit these properties of MDA-7 by applying MDA-7 to the suppression and prevention of infections by viruses and other pathogens.

The inventors seek to exploit the fact that MDA-7 functions in a manner that involves certain pathways in cancer cells that are involved in pathogen infection and pathogen replication by applying MDA-7 as a therapeutic and preventive agent against pathogen infection. For example, compositions that include MDA-7 can be applied in methods pertaining to the treatment and prevention of viral infection. Furthermore, MDA-7 may be applied as a therapeutic and preventive agent in bioterrorism attacks wherein the public is exposed to pathogens.

A. MDA-7

The methods of the present invention involve administering to a subject or contacting a cell with an MDA-7 polypeptide or a nucleic acid encoding an MDA-7 polypeptide. MDA-7 is a putative tumor suppressor that has been shown to suppress the growth of cancer cells that are p53-wild-type, p53-null and p53-mutant.

mda-7 is a tumor suppressor gene which was identified using a subtractive hybridization approach from human melanoma cells induced to differentiate with IFN-beta and mezerein (Jiang et al., 1995). mda-7 mRNA was expressed in normal melanocytes and early stages of melanoma, but was lost during melanoma progression (Jiang et al., 1995). Transfection of mda-7 expression plasmid into various tumor cell lines resulted in suppression of growth (Jiang et al., 1996). Based on these observations it was suggested that mda-7 is a novel tumor suppressor gene whose expression must be inhibited for tumor progression.

The tumor suppressor activities of mda-7 gene transfer have now been well established. Numerous studies have documented the growth suppression effected by elevated expression of MDA-7 protein in cancer cells from lung, breast, melanoma, prostate, mesothelioma, glioma etc (reviewed in Fisher et al., 2003). MDA-7 overexpression in normal cells however, lacks the cytotoxic effects seen in cancer cells (Mhashilkar et al., 2001; Lebedeva et al., 2003). It has recently demonstrated that Ad-mda7 causes growth suppression, cell cycle block, and apoptosis in non-small cell lung cancer cells in vitro and in vivo using xenograft models (Saeki et al., 2000; Saeki et al., 2002; Pataer et al., 2002).

The mda-7 gene is located on chromosome 1 at 1q32, and is contained within a cytokine cluster that encodes IL-10; IL-19 and IL-20 (Mhashilkar et al., 2001; Blumberg et al., 2001; Huang et al., 2001). Based upon its chromosomal localization in the IL-10 family cluster and its limited amino-acid identity to IL-10, mda-7 has now been designated as IL-24, and recent data indicate that this molecule functions as a pro-Th1 cytokine in human PBMC (Caudell et al., 2002). Further studies have demonstrated expression of mda-7 mRNA and MDA-7 protein in immune cells (Huang et al., 2001; Caudell et al., 2002). Thus mda-7 is an unusual pro-Th1 cytokine with pro-apoptotic activity.

Based upon its chromosomal localization in the IL-10 family cluster and its limited amino-acid identity to IL-10, mda-7 has now been designated as IL-24, and recent data indicate that this molecule functions as a pro-Th1 cytokine in human PBMC (Caudell et al., 2002). Further studies have demonstrated expression of mda-7 mRNA and MDA-7 protein in immune cells (Huang et al., 2001; Caudell et al., 2002). Thus mda-7 is an unusual pro-Th1 cytokine with pro-apoptotic activity.

A number of studies have evaluated molecules involved in mediating the apoptotic response of tumor cells to Ad-mda7. These studies have used cell lines from different tumor types and have shown regulation of a variety of diverse cellular mediators. For example, analysis of molecules involved in the effector phase of the apoptotic pathway has shown that MDA-7 can increase expression of p53, BAK, BAX, activate caspases 3, 8 and 9 and increase mitochondrial cytochrome c release in lung and breast cell lines (Mhashilkar et al., 2001; Saeki et al., 2000; Saeki et al., 2002; Pataer et al., 2002; Pataer et al., 2003). Analyses of signaling pathways have revealed Ad-mda 7 regulation of iNOS and MAPK in melanoma (Ekmekcioglu et al., 2003, Sarkar et al., 2002), and jun kinase, PI3K and PKR in lung and breast tumor cells (Pataer et al., 2002; Kawabe et al., 2002; Mhashilkar et al., 2003). Thus, different signaling pathways may be responsible for induction of apoptosis in different tumor types. This concept was recently validated by demonstrating that MDA-7 mediated killing of breast cancer cells was blocked by inhibitors of MAPK or MEKK pathways, whereas blocking these pathways had minimal effects against lung tumor cells (Mhashilkar et al., 2003).

Recent studies have demonstrated that Ad-mda7 transduction causes high levels of MDA-7 protein to be released from transduced cells (Mhashilkar et al., 2001).

MDA-7 mRNA has been identified in human PBMC (Ekmekcioglu et al., 2001), and no cytokine function of human MDA-7 protein was reported. MDA-7 has been designated as IL-24 based on the gene and protein sequence characteristics (NCBI database accession XM_001405). The murine MDA-7 protein homolog FISP (IL-4-Induced Secreted Protein) was reported as a Th2 specific cytokine (Schaefer et al., 2001). Transcription of FISP is induced by TCR and IL-4 receptor engagement and subsequent PKC and STAT6 activation as demonstrated by knockout studies. Expression of FISP was characterized but no function has been attributed yet to this putative cytokine. The rat MDA-7 homolog C49a (Mob-5) is 78% homologous to the mda-7 gene and has been linked to wound healing (Soo et al., 1999; Zhang et al., 2000). Mob-5 was also shown to be a secreted protein and a putative cell surface receptor was identified on ras transformed cells (Zhang et al., 2000). Therefore, homologues of the mda-7 gene and the secreted MDA-7 protein are expressed and secreted in various species. However, no data has emerged to show MDA-7 has cytokine activity. Such activity has ramifications for the treatment of a wide variety of diseases and infections by enhancing immunogenicity of an antigen.

The mda-7 cDNA (SEQ ID NO: 1) encodes a novel, evolutionarily conserved protein of 206 amino acids (SEQ ID NO: 2) with a predicted size of 23.8 kDa. The deduced amino acid sequence contains a hydrophobic stretch from about amino acid 26 to 45, which has characteristics of a signal sequence. The protein sequence shows no significant homology to known proteins with the exception of a 42 amino acid stretch that is 54% identical to interleukin 10 (IL-10). Structural analysis has determined that MDA-7 (IL-BKW or IL-20) displays the structural characteristics of the cytokine family (WO 98/28425, specifically incorporated herein by reference). The structural characteristics and limited identity across a small stretch of amino acids implies an extracellular function for MDA-7. The expression of MDA-7 is inversely correlated with melanoma progression as demonstrated by increased mRNA levels in normal melanocytes as compared to primary and metastatic melanomas as well as decreased MDA-7 expression in early vertical growth phase melanoma cells selected for enhanced tumor formation in nude mice. Additional information and data regarding MDA-7 can be found in U.S. patent application Ser. Nos. 09/615,154 and 10/017,472, which are herein incorporated by reference in their entirety.

Additional studies have shown that elevated expression of MDA-7 suppressed cancer cell growth in vitro and selectively induced apoptosis in human breast cancer cells as well as inhibiting tumor growth in nude mice (Jiang et al., 1996; Su et al., 1998). Jiang et al. (1996) report findings that mda-7 is a potent growth suppressing gene in cancer cells of diverse origins including breast, central nervous system, cervix, colon, prostate, and connective tissue. A colony inhibition assay was used to demonstrate that elevated expression of MDA-7 enhanced growth inhibition in human cervical carcinoma (HeLa), human breast carcinoma (MCF-7 and T47D), colon carcinoma (LS174T and SW480), nasopharyngeal carcinoma (HONE-1), prostate carcinoma (DU-145), melanoma (HO-1 and C8161), glioblastome multiforme (GBM-18 and T98G), and osteosarcoma (Saos-2). Mda-7 overexpression in normal cells (HMECs, HBL-100, and CREF-Trans6) showed limited growth inhibition indicating that mda-7 transgene effects are not manifest in normal cells. Taken together, the data indicates that growth inhibition by elevated expression of MDA-7 is more effective in vitro in cancer cells than in normal cells.

Su et al. (1998) reported investigations into the mechanism by which MDA-7 suppressed cancer cell growth. The studies reported that ectopic expression of MDA-7 in breast cancer cell lines MCF-7 and T47D induced apoptosis as detected by cell cycle analysis and TUNEL assay without an effect on the normal HBL-100 cells. Western blot analysis of cell lysates from cells infected with adenovirus mda-7 ("Ad-mda-7") showed an upregulation of the apoptosis stimulating protein BAX. Ad-mda7 infection elevated levels of BAX protein only in MCF-7 and T47D cells and not normal HBL-100 or HMEC cells. These data lead the investigators to evaluate the effect of ex vivo Ad-mda7 transduction on xenograft tumor formation of MCF-7 tumor cells. Ex vivo transduction resulted in the inhibition of tumor formation and progression in the tumor xenograft model.

In certain embodiments of the present invention, the mda-7 is provided as a nucleic acid expressing the MDA-7 polypeptide. In specific embodiments, the nucleic acid is a viral vector, wherein the viral vector dose is or is at least $10^3$, $10^4$, $10^5$, $10^6$, $10^7$, $10^8$, $10^9$, $10^{10}$, $10^{11}$, $10^{12}$, $10^{13}$, $10^{14}$, $10^{15}$ or higher pfu or viral particles. In certain embodiments, the viral vector is an adenoviral vector, a retroviral vector, a vaccinia viral vector, an adeno-associated viral vector, a polyoma viral vector, an alphaviral vector, a rhabdoviral vector, or a herpesviral vector. Most preferably, the viral vector is an adenoviral vector. In other specific embodiments, the nucleic acid is a non-viral vector.

In certain embodiments, the nucleic acid expressing the polypeptide is operably linked to a promoter. Non-limiting examples of promoters suitable for the present invention include a CMV IE, dectin-1, dectin-2, human CD11c, F4/80, SM22 or MHC class II promoter, however, any other promoter that is useful to drive expression of the mda-7 gene or the immunogen of the present invention, such as those set forth herein, is believed to be applicable to the practice of the present invention.

1. Nucleic Acids, Vectors and Regulatory Signals

The present invention concerns methods that involve compositions that include polynucleotides or nucleic acid molecules relating to the mda-7 gene and its gene product MDA-7. These polynucleotides or nucleic acid molecules are isolatable and purifiable from mammalian cells. It is contemplated that an isolated and purified MDA-7 nucleic acid molecule, either the secreted or full-length version, that is a nucleic acid molecule related to the mda-7 gene product, may take the form of RNA or DNA. Similarly, the nucleic acid molecule related to the immunogenic molecule may take the form of RNA or DNA. As used herein, the term "RNA transcript" refers to an RNA molecule that is the product of transcription from a DNA nucleic acid molecule. Such a transcript may encode for one or more polypeptides.

As used in this application, the term "polynucleotide" refers to a nucleic acid molecule, RNA or DNA, that has been isolated free of total genomic nucleic acid. Therefore, a "polynucleotide encoding MDA-7" refers to a nucleic acid segment that contains MDA-7 coding sequences, yet is isolated away from, or purified and free of, total genomic DNA and proteins. When the present application refers to the function or activity of a MDA-7-encoding polynucleotide or nucleic acid, it is meant that the polynucleotide encodes a molecule that has the ability to enhance an immune response. Further, a "polynucleotide encoding an immunogen" refers to a nucleic acid segment that contains an immunogenic coding sequences, yet is isolated away from, or purified and free of, total genomic DNA and proteins. When the present application refers to the function or activity of an immunogen encoding an immunogen, it is meant that the polynucleotide encodes an immunogenic molecule that has the ability to induce an immune response in the body of a human.

The term "cDNA" is intended to refer to DNA prepared using RNA as a template. The advantage of using a cDNA, as opposed to genomic DNA or an RNA transcript is stability and the ability to manipulate the sequence using recombinant DNA technology (see Sambrook, 2001; Ausubel, 1996). There may be times when the full or partial genomic sequence is some. Alternatively, cDNAs may be advantageous because it represents coding regions of a polypeptide and eliminates introns and other regulatory regions.

It also is contemplated that a given MDA-7-encoding nucleic acid or mda-7 gene from a given cell may be represented by natural variants or strains that have slightly different nucleic acid sequences but, nonetheless, encode a MDA-7 polypeptide; a human MDA-7 polypeptide is a specific embodiment. Consequently, the present invention also encompasses derivatives of MDA-7 with minimal amino acid changes, but that possess the same activity.

The term "gene" is used for simplicity to refer to a functional protein, polypeptide, or peptide-encoding unit. As will be understood by those in the art, this functional term includes genomic sequences, cDNA sequences, and smaller engineered gene segments that express, or may be adapted to express, proteins, polypeptides, domains, peptides, fusion proteins, and mutants. The nucleic acid molecule encoding MDA-7 or another therapeutic polypeptide such as the immunogen may comprise a contiguous nucleic acid sequence that is 5 or more nucleotides nucleotides, nucleosides, or base pairs in length. For example, in certain embodiments, the nucleic acid molecule is 5, 6, 7, 8, 9, 10, 20, 40, 100, 150, 200, 400, 600, 800, 1200, 3000, 6000, 9000, 12000 or more nucleotides, nucleosides, or base pairs in length. Such sequences may be identical or complementary to SEQ ID NO: 1 (MDA-7 encoding sequence).

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

In particular embodiments, the invention concerns isolated DNA segments and recombinant vectors incorporating DNA sequences that encode a MDA-7 protein, polypeptide or peptide that includes within its amino acid sequence a contiguous amino acid sequence in accordance with, or essentially as set forth in, SEQ ID NO: 2, corresponding to the MDA-7 designated "human MDA-7" or "MDA-7 polypeptide."

The term "a sequence essentially as set forth in SEQ ID NO: 2" means that the sequence substantially corresponds to a portion of SEQ ID NO: 2 and has relatively few amino acids that are not identical to, or a biologically functional equivalent of, the amino acids of SEQ ID NO: 2.

The term "biologically functional equivalent" is well understood in the art and is further defined in detail herein. Accordingly, sequences that have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more preferably about 81% and about 90%; or even more preferably, between about 91% and about 99%; of amino acids that are identical or functionally equivalent to the amino acids of SEQ ID NO: 2 will be sequences that are "essentially as set forth in SEQ ID NO: 2" provided the biological activity of the protein is maintained. In particular embodiments, the biological activity of a MDA-7 protein, polypeptide or peptide, or a biologically functional equivalent, comprises enhancing an immune response. Further, in particular embodiments, the biological activity of an immunogen, an immunogenic molecule that is a protein, polypeptide or peptide, or a biologically functional equivalent, comprises immunogenicity, which refers to the molecule's ability to induce an immune response in the body of a human. In certain other embodiments, the invention concerns isolated DNA segments and recombinant vectors that include within their sequence a nucleic acid sequence essentially as set forth in SEQ ID NO: 1. The term "essentially as set forth in SEQ ID NO: 1" is used in the same sense as described above and means that the nucleic acid sequence substantially corresponds to a portion of SEQ ID NO: 1 and has relatively few codons that are not identical, or functionally equivalent, to the codons of SEQ ID NO: 1. Again, DNA segments that encode proteins, polypeptide or peptides exhibiting MDA-7 activity will be most some.

In particular embodiments, the invention concerns isolated nucleic acid segments and recombinant vectors incorporating DNA sequences that encode MDA-7 polypeptides or peptides that include within its amino acid sequence a contiguous amino acid sequence in accordance with, or essentially corresponding to MDA-7 polypeptides. In other embodiments, the invention relates to an isolated nucleic acid segment and recombinant vectors incorporating DNA sequences that encode an immunogen, protein, polypeptide or peptides that include within its amino acid sequence a contiguous amino acid sequence in accordance with, or essentially corresponding to the immunogen.

Vectors of the present invention are designed, primarily, to transform cells with a therapeutic mda-7 gene under the control of regulated eukaryotic promoters (i.e., inducible, repressible, tissue specific). Also, the vectors may contain a selectable marker if, for no other reason, to facilitate their manipulation in vitro. However, selectable markers may play an important role in producing recombinant cells.

TABLES 1 and 2, below, list a variety of regulatory signals for use according to the present invention.

TABLE 1

Inducible Elements

| Element | Inducer | References |
|---------|---------|------------|
| MT II | Phorbol Ester (TPA) Heavy metals | Palmiter et al., 1982; Haslinger and Karin, 1985; Searle et al., 1985; Stuart et al., 1985; Imagawa et al., 1987; Karin et al., 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Yamamoto et al., 1983; Lee et al., 1984; Ponta et al., 1985; Si.e.,i et al., 1986 |
| β-Interferon | poly(rI)X poly(rc) | Tavernier et al., 1983 |

TABLE 1-continued

Inducible Elements

| Element | Inducer | References |
|---|---|---|
| Adenovirus 5 E2 | E1a | Imperiale and Nevins, 1984 |
| Collagenase | Phorbol Ester (TPA) | Angel et al., 1987a |
| Stromelysin | Phorbol Ester (TPA) | Angel et al., 1987b |
| SV40 | Phorbol Ester (TFA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I | Interferon | Blanar et al., 1989 |
| Gene H-2κb | | |
| HSP70 | E1a, SV40 Large T Antigen | Taylor et al., 1989; Taylor and Kingston, 1990a,b |
| Proliferin | Phorbol Ester-TPA | Mordacq and Linzer, 1989 |
| Tumor Necrosis Factor | | Hensel et al., 1989 |
| Thyroid Stimulating Hormone α Gene | Thyroid Hormone | Chatterjee et al., 1989 |

TABLE 2

Other Promoter/Enhancer Elements

| Promoter/Enhancer | References |
|---|---|
| Immunoglobulin Heavy Chain | Banerji et al., 1983; Gillies et al., 1983; Grosschedl and Baltimore, 1985; Atchinson and Perry, 1986, 1987; Imler et al., 1987; Neuberger et al., 1988; Kiledjian et al., 1988; |
| Immunoglobulin Light Chain | Queen and Baltimore, 1983; Picard and Schaffner, 1985 |
| T-Cell Receptor | Luria et al., 1987, Winoto and Baltimore, 1989; Redondo et al., 1990 |
| HLA DQ α and DQ β | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRα | Sherman et al., 1989 |
| β-Actin | Kawamoto et al., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987; Tronche et al., 1989, 1990 |
| α-Fetoprotein | Godbout et al., 1988; Campere and Tilghman, 1989 |
| γ-Globin | Bodine and Ley, 1987; Perez-Stable and Constantini, 1990 |
| β-Globin | Trudel and Constantini, 1987 |
| c-fos | Cohen et al., 1987 |
| c-HA-ras | Triesman, 1985; Deschamps et al., 1985 |
| Insulin | Edlund et al., 1985 |
| Neural Cell Adhesion Molecule (NCAM) | Hirsch et al., 1990 |
| $a_1$-Antitrypain | Latimer et al., 1990 |
| H2B (TH2B) Histone | Hwang et al., 1990 |
| Mouse or Type I Collagen | Rippe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; Dandolo et al., 1983; Hen et al., 1986; Si.e.,i et al., 1988; Campbell and Villarreal, 1988 |

TABLE 2-continued

Other Promoter/Enhancer Elements

| Promoter/Enhancer | References |
| --- | --- |
| Retroviruses | Kriegler and Botchan, 1983; Kriegler et al., 1984a,b; Bosze et al., 1986; Miksicek et al., 1986; Celander and Haseltine, 1987; Thiesen et al., 1988; Celander et al., 1988; Chol et al., 1996; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987, Stephens and Hentschel, 1987 |
| Hepatitis B Virus | Bulla and Siddiqui, 1988; Jameel and Siddiqui, 1986; Shaul and Ben-Levy, 1987; Spandau and Lee, 1988 |
| Human Immunodeficiency Virus | Muesing et al., 1987; Hauber and Cullan, 1988; Jakobovits et al., 1988; Feng and Holland, 1988; Takebe et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation.

The term "promoter" will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either co-operatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities.

Promoters and enhancers have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

In some embodiments, the promoter for use in the present invention is the cytomegalovirus (CMV) promoter. This promoter is commercially available from Invitrogen in the vector pcDNAIII, which is some for use in the present invention. Also contemplated as useful in the present invention are the dectin-1 and dectin-2 promoters. Below are a list of additional viral promoters, cellular promoters/enhancers and inducible promoters/enhancers that could be used in combination with the present invention. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

Another signal that may prove useful is a polyadenylation signal. Such signals may be obtained from the human growth hormone (hGH) gene, the bovine growth hormone (BGH) gene, or SV40.

The use of internal ribosome binding sites (IRES) elements are used to create multigene, or polycistronic, messages. IRES elements are able to bypass the ribosome scanning model of 5-methylated cap-dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

In any event, it will be understood that promoters are DNA elements which when positioned functionally upstream of a gene leads to the expression of that gene. Most transgene constructs of the present invention are functionally positioned downstream of a promoter element.

2. Proteins, Peptides and Polypeptides
a. Biologically Functional Equivalents

The present invention is directed to enhancing an immune response by providing an effective amount of a MDA-7 polypeptide. In certain embodiments, the MDA-7 polypeptide is directly provided. In specific embodiments, the MDA-7 polypeptide is provided before therapy. In specific embodiments, the MDA-7 polypeptide is administered at the same time as administration of an immunogenic molecule, such as an antigen, for purposes of immune therapy. In other specific embodiments, the MDA-7 polypeptide is provided after therapy, and in some instances, after providing an immunogenic molecule for purposes of treating, diagnosing or prognosing induction of an immune response.

Additional embodiments of the invention encompass the use of a purified protein composition comprising MDA-7 protein, truncated versions of MDA-7, and peptides derived from MDA-7 amino acid sequence administered to cells or subjects for the inhibition of angiogenesis. Truncated molecules of MDA-7 include, for example, molecules beginning approximately at MDA-7 amino acid residues 46-49 and further N-terminal truncations. Specifically contemplated are molecules start at residue 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, and 182, and terminate at residue 206. In additional embodiments, residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, and 46 are included with other contiguous residues of MDA-7, as shown in SEQ ID NO: 2.

As will be understood by those of skill in the art, modification and changes may be made in the structure of a MDA-7 polypeptide or peptide, an immunogenic molecule, or an immunogenic product and still produce a molecule having like or otherwise desirable characteristics. For example, certain amino acids may be substituted for other amino acids in a protein structure without appreciable loss of interactive binding capacity with structures such as, for example, antigen-binding regions of antibodies or binding sites on molecules such as Tat and RNA polymerase II. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. It is thus contemplated by the inventors that various changes may be made in the sequence of HIV polypeptides or peptides (or underlying DNA) without appreciable loss of their biological utility or activity.

In terms of functional equivalents, the skilled artisan also understands it is also well understood by the skilled artisan that inherent in the definition of a biologically-functional equivalent protein or peptide, is the concept of a limit to the number of changes that may be made within a defined portion of a molecule that still result in a molecule with an acceptable level of equivalent biological activity. Biologically-functional equivalent peptides are thus defined herein as those peptides in which certain, not most or all, of the amino acids may be substituted. In particular, where small peptides are concerned, less amino acids may be changed. Of course, a plurality of distinct proteins/peptides with different substitutions may easily be made and used in accordance with the invention.

It is also well understood that where certain residues are shown to be particularly important to the biological or structural properties of a protein or peptide, e.g., residues in the active site of an enzyme, or in the RNA polymerase II binding region, such residues may not generally be exchanged. This is the case in the present invention, where residues shown to be necessary for inducing an immune response should not generally be changed, which is contemplated for both the MDA-7 polypeptide and the immunogen product.

Amino acid substitutions are generally based on the relative similarity of the amino acid side-chain substituents, for example, their hydrophobicity, hydrophilicity, charge, size, and the like. An analysis of the size, shape, and type of the amino acid side-chain substituents reveals that arginine, lysine, and histidine are all positively charged residues; that alanine, glycine, and serine are all a similar size; and that phenylalanine, tryptophan, and tyrosine all have a generally similar shape. Therefore, based upon these considerations, the following subsets are defined herein as biologically functional equivalents: arginine, lysine, and histidine; alanine, glycine, and serine; and phenylalanine, tryptophan, and tyrosine.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, some, those which are within ±1 are particularly preferred, some, and those within ±0.5 are even more particularly preferred. It is also understood in the art that the substitution of like amino acids can be made effectively on the basis of hydrophilicity, particularly where the biological functional equivalent protein or peptide thereby created is intended for use in immunological embodiments, as in the present case. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA, taking into consideration also that the genetic code is degenerate and that two or more codons may encode the same amino acid.

b. Synthetic Peptides

The compositions of the invention may include a peptide modified to render it biologically protected. Biologically protected peptides have certain advantages over unprotected peptides when administered to human subjects and, as disclosed in U.S. Pat. No. 5,028,592, incorporated herein by reference, protected peptides often exhibit increased pharmacological activity.

Compositions for use in the present invention may also comprise peptides which include all L-amino acids, all D-amino acids, or a mixture thereof. The use of D-amino acids may confer additional resistance to proteases naturally found within the human body and are less immunogenic and can therefore be expected to have longer biological half lives.

c. In Vitro Protein Production

Following transduction with a viral vector according to some embodiments of the present invention, primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well known to those of ordinary skill in the art.

One embodiment of the foregoing involves the use of gene transfer to immortalize cells for the production and/or presentation of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Another embodiment of the present invention uses autologous B lymphocyte cell lines, which are transfected with a viral vector that expresses an immunogen product, and more specifically, an protein having immunogenic activity. Other examples of mammalian host cell lines include Vero and HeLa cells, other B- and T-cell lines, such as CEM, 721.221, H9, Jurkat, Raji, etc., as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk−, hgprt− or aprt− cells, respectively. Also, anti-metabolite resistance can be used as the basis of selection: for dhfr, which confers resistance to; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

B. RELATIONSHIP OF MDA-7 AND PKR

The observed upregulation of the apoptosis-related BAX gene in p53 null cells indicates that MDA-7 is capable of using p53-independent mechanisms to induce the destruction of cancer cells. It has been observed that adenoviral-mediated overexpression of MDA-7 led to the rapid induction and activation of PKR with subsequent phosphorylation of eIF-2α, other PKR target substrates and apoptosis induction. Specific inhibition of PKR by 2-aminopurine (2-AP) in lung cancer cells abrogates Ad-mda7 induced PKR activation, PKR substrate target phosphorylation and apoptosis induction. As evidenced by PKR null fibroblasts, Ad-mda7 apoptosis is dependent on a functional PKR pathway. These characteristics indicate that MDA-7 has broad therapeutic, prognostic and diagnostic potential as an inducer of PKR and, consequently, an enhancer of an induced immune response.

PKR exerts antiviral and anticellular functions, and is involved in regulating a number of physiologic processes that include cell growth and differentiation (U.S. Pat. No. 6,326,466; Feng et al., 1992; Petryshyn et al., 1988; Petryshyn et al., 1984; Judware et al., 1991), tumor suppression (Koromilas et al., 1992; Meurs et al., 1993), and modulation of signal transduction pathways (Leonardo et al., 1989; Kumar et al., 1994; Maran et al., 1994).

Upregulation of PKR leads to the induction of apoptosis in various cancer cell lines. Furthermore, in myelodysplasias, critical tumorigenic deletions of the IRF-1 gene on chromosome 5q (Beretta et al., 1996) appear associated with decreased PKR levels and immunohistochemical analyses of lung and colorectal cancers demonstrate an association with PKR expression and prolonged survival (Haines et al., 1992). PKR appears to mediate anti-tumorigenic activity through the activation of multiple transduction pathways culminating in growth inhibition and apoptosis induction. Activation of these pathways occurs after the latent, inactive homodimeric form is induced by activating signals to undergo conformational changes leading to auto-phosphorylation and activation (Vattem et al., 2001). Once activated, PKR is able to phosphorylate various substrate targets, which are important in growth control and apoptosis induction (Saelens et al., 2001; Sudhakar et al., 2000). Stimulation of the immune system has been linked to apoptosis (Albert et al., 1998; Restifo et al., 2001). Further, artificial induction of apoptosis has been demonstrated to enhance the immunogenicity of a vaccine due to the stimulatory effect of dendritic cells that became activated by transfection of the apoptotic cells (Chattergoon et al., 2000).

C. PATHOGENS

The present invention pertains to methods of suppressing or preventing an infection of a subject by a pathogen. The invention also pertains to methods of suppressing or preventing a viral infection of a cell. Subjects who are infected by a pathogen may or may not be symptomatic.

Concerning viruses, any virus is contemplated for inclusion in the methods of treatment of the present invention. One of ordinary skill in the art would be familiar with the many different types of viral pathogens that are known. The following viruses are mentioned by way of example: influenza A, B and C, parainfluenza, paramyxoviruses, Newcastle disease virus, respiratory syncytial virus, measles, mumps, parvoviruses, Epstein-Barr virus, rhinoviruses, coxsackieviruses, echoviruses, reoviruses, rhabdoviruses, lymphocytic choriomeningitis, coronavirus, polioviruses, herpes simplex, human immunodeficiency viruses, cytomegaloviruses, papillomaviruses, virus B, varicella-zoster, poxviruses, rubella, rabies, picornaviruses, rotavirus and Kaposi associated herpes virus.

In certain embodiments of the present invention, the virus is an endoplasmic reticulum-tropic virus. This is a class of viruses that utilize the endoplasmic reticulum (ER) for production of critical viral proteins. Any endoplasmic reticulum tropic virus is contemplated by the present invention. For example, the virus may be Hepatitis C virus, a flavivirus species, HHV6, rubella, LCMV, HIV, or Hepatitis B virus.

In certain embodiments, the pathogen is a bacterium. Any bacterium is contemplated for suppression and prevention by the methods of the present invention. For example, the bacterium may be a gram negative bacterium, a gram positive bacterium, or a bacterium for which gram staining is not applicable. Examples of such bacteria include, but are not limited to, the 83 or more distinct serotypes of pneumococci, streptococci such as *S. pyogenes, S. agalactiae, S. equi, S. canis, S. bovis, S. equinus, S. anginosus, S. sanguis, S. salivarius, S. mitis, S. mutans*, other viridans streptococci, peptostreptococci, other related species of streptococci, enterococci such as *Enterococcus faecalis, Enterococcus faecium*, staphylococci, such as *Staphylococcus epidermidis, Staphylococcus aureus, Hemophilus influenzae, Pseudomonas* species such as *Pseudomonas aeruginosa, Pseudomonas pseudomallei, Pseudomonas mallei*, brucellas such as *Brucella melitensis, Brucella suis, Brucella abortus, Bordetella pertussis, Borellia* species, such as *Borellia burgedorferi, Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi*, etc. *Listeria monocytogenes, Nocordia asteroides, Bacteroides* species, *Actinomycetes* species, *Treponema pallidum, Leptospirosa* species, *Haemophilus* species, *Helicobacter* species, including *Helicobacter pylori, Treponema* species and related organisms. The invention may also be useful against gram-negative bacteria such as *Klebsiella pneumoniae, Escherichia coli, Proteus, Serratia* species, *Acinetobacter, Yersinia pestis, Francisella tularensis, Enterobacter* species, *Bacteriodes* and *Legionella* species, *Shigella* species, *Mycobacterium* species (e.g., *Mycobacterium tuberculosis, Mycobacterium bovis* or other mycobacteria infections), *Mycobacterium avium* complex (MAC), *Mycobacterium marinum, Mycobacterium fortuitum, Mycobacterium kansaii, Yersinia* infections (e.g., *Yersinia pestis, Yersinia enterocolitica* or *Yersinia pseudotuberculosis*) and the like. In addition, the invention in contemplated to be of use in controlling protozoan, helminth or other macroscopic infections by organisms such as *Cryptosporidium, Entamoeba, Plasmodiium, Giardia, Leishmania, Trypanasoma, Trichomonas, Naegleria, Isospora belli, Toxoplasma gondii, Trichomonas vaginalis, Wunchereria, Ascaris, Schistosoma* species, *Cyclospora* species, for example, and for *Chlamydia trachomatis* and other *Chlamydia* infections such as *Chlamydia psittaci*, or *Chlamydia pneumoniae*, for example. Of course it is understood that the invention may be used on any pathogen against which an effective antibody can be made.

Fungal and other mycotic pathogens (some of which are described in Beneke, 1979; Smith, 1989; and Scrip's Antifungal Report, 1992) are also contemplated as a pathogen addressed by the methods of the present invention. Fungal disease contemplated in the context of the invention includes, but is not limited to, Aspergillosis, Black piedra, Candidiasis, Chromomycosis, Cryptococcosis, Onychomycosis, or Otitis extema (otomycosis), Phaeohyphomycosis, Phycomycosis, Pityriasis versicolor, ringworm, *Tinea barbae, Tinea capitis, Tinea corporis, Tinea cruris, Tinea favosa, Tinea imbricata, Tinea manuum, Tinea nigra* (palmaris), *Tinea pedis, Tinea unguium*, Torulopsosis, Trichomycosis axillaris, White piedra, and their synonyms, to severe systemic or opportunistic infections, such as, but not limited to, Actinomycosis, Aspergillosis, Candidiasis, *Chromomycosis*, Coccidioidomycosis, Cryptococcosis, Entomophthoramycosis, Geotrichosis, Histoplasmosis, Mucormycosis, Mycetoma, Nocardiosis, North American Blastomycosis, Paracoccidioidomycosis, Phaeohyphomycosis, Phycomycosis, Pneumocystic pneumonia, Pythiosis, Sporotrichosis, and Torulopsosis, and their synonyms, some of which may be fatal. Known fungal and mycotic pathogens include, but are not limited to, *Absidia* spp., *Actinomadura madurae, Actinomyces* spp., *Allescheria boydii, Alternaria* spp., *Anthopsis deltoidea, Apophysomyces elegans, Arnium leoporinum, Aspergillus* spp., *Aureobasidium pullulans, Basidiobolus ranarum, Bipolaris* spp., *Blastomyces dermatitidis, Candida* spp., *Cephalosporium* spp., *Chaetoconidium* spp., *Chaetomium* spp., *Cladosporium* spp., *Coccidioides immitis, Conidiobolus* spp., *Corynebacterium tenuis, Cryptococcus* spp., *Cunninghamella bertholletiae, Curvularia* spp., *Dactylaria* spp., *Epidermophyton* spp., *Epidermophyton floccosum, Exserophilum* spp., *Exophiala* spp., *Fonsecaea* spp., *Fusarium* spp., *Geotrichum* spp., *Helminthosporium* spp., *Histoplasma* spp., *Lecythophora* spp., *Madurella* spp., *Malassezia furfur, Microsporum* spp., *Mucor* spp., *Mycocentrospora acerina, Nocardia* spp., *Paracoccidioides brasiliensis, Penicillium* spp., *Phaeosclera dematioides, Phaeoannellomyces* spp., *Phialemonium obovatum, Phialophora* spp., *Phoma* spp., *Piedraia hortai, Pneumocystis carinii, Pythium insidiosum, Rhinocladiella aquaspersa, Rhizomucor pusillus, Rhizopus* spp., *Saksenaea vasiformis, Sarcinomyces*

*phaeomuriformis, Sporothrix schenckii, Syncephalastrum racemosum, Taeniolella boppii, Torulopsosis* spp., *Trichophyton* spp., *Trichosporon* spp., *Ulocladium chartarum, Wangiella dermatitidis, Xylohypha* spp., *Zygomyetes* spp. and their synonyms. Other fungi that have pathogenic potential include, but are not limited to, *Thermomucor indicae-seudaticae, Radiomyces* spp., and other species of known pathogenic genera.

In addition, the invention may prove useful in controlling protozoan or macroscopic infections by organisms such as *Cryptosporidium, Isospora belli, Toxoplasma gondii, Trichomonas vaginalis, Cyclospora* species, for example, and for *Chlamydia trachomatis* and other *Chlamydia* infections such as *Chlamydia psittaci*, or *Chlamydia pneumoniae*, for example.

D. EXPRESSION CASSETTES

Certain embodiments of the invention pertain to methods utilizing compositions that include an expression cassette. In particular, in certain embodiments, administering the composition to the subject may involve providing to the subject an expression cassette comprising a promoter, active in the subject, operably linked to a polynucleotide encoding an MDA-7 polypeptide. In certain embodiments that pertain to suppressing or preventing a viral infection of a cell, the MDA-7 polypeptide or nucleic acid encoding the MDA-7 polypeptide may comprise an expression cassette that includes a promoter, active in the cell, operably linked to a polynucleotide encoding an MDA-7 polypeptide.

Throughout this application, the term "expression cassette" is meant to include any type of genetic construct containing a nucleic acid coding for a gene product in which part or all of the nucleic acid encoding sequence is capable of being transcribed. The transcript may be translated into a protein or polypeptide, but it need not be. Thus, in certain embodiments, expression includes both transcription of a gene and translation of a mRNA into a polypeptide.

In order for the expression cassette to effect expression of a polypeptide, the polynucleotide encoding the polynucleotide will be under the transcriptional control of a promoter. A "promoter" is a control sequence that is a region of a nucleic acid sequence at which initiation and rate of transcription are controlled. It may contain genetic elements at which regulatory proteins and molecules may bind such as RNA polymerase and other transcription factors. The phrase "operatively linked" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence. One of skill in the art would understand how to use a promoter or enhancer to promote expression of an MDA-7 polypeptide.

In certain embodiments of the invention, the delivery of an expression cassette in a cell may be identified in vitro or in vivo by including a marker in the expression vector. The marker would result in an identifiable change to the transfected cell permitting easy identification of expression. The selectable marker employed is not believed to be important, so long as it is capable of being expressed along with the polynucleotide of the expression cassette. Examples of selectable markers are well known to one of skill in the art.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). One of skill in the art would be familiar with use of IRES in expression cassettes.

Expression cassettes can include a multiple cloning site (MCS), which is a nucleic acid region that contains multiple restriction enzyme sites, any of which can be used in conjunction with standard recombinant technology to digest the vector. See Carbonelli et al. (1999); Levenson et al. (1998); Cocea (1997). "Restriction enzyme digestion" refers to catalytic cleavage of a nucleic acid molecule with an enzyme that functions only at specific locations in a nucleic acid molecule. Techniques involving restriction enzymes and ligation reactions are well known to those of skill in the art of recombinant technology.

In expression, one will typically include a polyadenylation signal to effect proper polyadenylation of the transcript. The nature of the polyadenylation signal is not believed to be crucial to the successful practice of the invention, and/or any such sequence may be employed. One of skill in the art would understand how to use these signals to effect proper polyadenylation of the transcript.

In certain embodiments of the present invention, the expression cassette comprises a virus or engineered construct derived from a viral genome. The ability of certain viruses to enter cells via receptor-mediated endocytosis and, in some cases, integrate into the host cell chromosomes, have made them attractive candidates for gene transfer in to mammalian cells. However, because it has been demonstrated that direct uptake of naked DNA, as well as receptor-mediated uptake of DNA complexes, expression vectors need not be viral but, instead, may be any plasmid, cosmid or phage construct that is capable of supporting expression of encoded genes in mammalian cells, such as pUC or Bluescript™ plasmid series. One of ordinary skill in the art would be familiar with use of viruses as tools to promote expression of the polypeptide.

In certain embodiments of the invention, a treated cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

E. GENE TRANSFER

Certain embodiments of the present invention pertain to methods wherein the expression cassette that includes a promoter, active in the subject or cell, is operably linked to a polynucleotide encoding an MDA-7 polypeptide, and wherein the expression cassette is carried in a viral vector. In other embodiments, the expression cassette is carried in a nonviral vector.

1. Viral Transformation

One method for delivery of the expression cassette involves the use of an viral expression vector. Any viral expression vector is contemplated for application in the present invention.

a. Adenoviral Infection

In certain embodiments of the present invention, the viral vector is an adenoviral vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a recombinant gene construct that has been cloned therein.

The vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5-tripartite leader (TPL) sequence which makes them some mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the some helper cell line is 293.

Racher et al. (1995) have disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

The adenovirus vector may be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the some starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$-$10^{13}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Animal studies have suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

b. Retroviral Infection

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, packaging cell lines are available that should greatly decrease the likelihood of recombination (Markowitz et al., 1988; Hersdorffer et al., 1990).

c. AAV Infection

Certain embodiments of the present invention involve use of a viral expression vector wherein the vector is an adeno-associated virus (AAV) vector. AAV is an attractive vector system for use in the present invention as it has a high frequency of integration and it can infect nondividing cells, thus making it useful for delivery of genes into mammalian cells in tissue culture (Muzyczka, 1992). AAV has a broad host range for infectivity (Tratschin et al., 1984; Laughlin et al., 1986; Lebkowski et al., 1988; McLaughlin et al., 1988), which means it is applicable for use with the present invention. Details concerning the generation and use of rAAV vectors are described in U.S. Pat. No. 5,139,941 and U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt et al., 1994; Lebkowski et al., 1988; Samulski et al., 1989; Shelling and Smith, 1994; Yoder et al., 1994; Zhou et al., 1994; Hermonat and Muzyczka, 1984; Tratschin et al., 1985; McLaughlin et al., 1988) and genes involved in human diseases (Flotte et al., 1992; Ohi et al., 1990; Walsh et al., 1994; Wei et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild-type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild-type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995). Cell lines carrying the rAAV DNA as an integrated provirus can also be used (Flotte et al., 1995).

d. Other Viral Vectors

Other viral vectors may be employed as constructs in the present invention. Vectors derived from viruses such as vaccinia virus (Ridgeway, 1988; Baichwal and Sugden, 1986;

Coupar et al., 1988) and herpes viruses may be employed. They offer several attractive features for various mammalian cells (Friedmann, 1989; Ridgeway, 1988; Baichwal and Sugden, 1986; Coupar et al., 1988; Horwich et al., 1990).

A molecularly cloned strain of Venezuelan equine encephalitis (VEE) virus has been genetically refined as a replication competent vaccine vector for the expression of heterologous viral proteins (Davis et al., 1996). Studies have demonstrated that VEE infection stimulates potent CTL responses and has been suggested that VEE may be an extremely useful vector for immunizations (Caley et al., 1997). It is contemplated in the present invention, that VEE virus may be useful in targeting dendritic cells.

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. (1991) recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In still further embodiments of the present invention, the nucleic acid encoding a MDA-7 to be delivered is housed within an infective virus that has been engineered to express a specific binding ligand. Alternatively, the nucleic acid encoding the MDA-7 polypeptide to be delivered is housed within an infective virus that has been engineered to express an immunogen. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via asialoglycoprotein receptors.

For example, to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

2. Non-Viral Delivery

In addition to viral delivery of the nucleic acid encoding a MDA-7 protein, the following are additional methods of recombinant gene delivery to a given host cell and are thus considered in the present invention.

a. Lipid Mediated Transformation

In a further embodiment of the invention, the gene construct may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL).

Lipid-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of lipid-mediated delivery and expression of foreign DNA in cultured chick embryo, HeLa and hepatoma cells.

Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in lipid vehicle stability in the presence and absence of serum proteins. The interaction between lipid vehicles and serum proteins has a dramatic impact on the stability characteristics of lipid vehicles (Yang and Huang, 1997). Cationic lipids attract and bind negatively charged serum proteins. Lipid vehicles associated with serum proteins are either dissolved or taken up by macrophages leading to their removal from circulation. Current in vivo lipid delivery methods use subcutaneous, intradermal, intratumoral, or intracranial injection to avoid the toxicity and stability problems associated with cationic lipids in the circulation. The interaction of lipid vehicles and plasma proteins is responsible for the disparity between the efficiency of in vitro (Felgner et al., 1987) and in vivo gene transfer (Zhu et al., 1993; Philip et al., 1993; Solodin et al., 1995; Liu et al., 1995; Thierry et al., 1995; Tsukamoto et al., 1995; Aksentijevich et al., 1996).

Recent advances in lipid formulations have improved the efficiency of gene transfer in vivo (Smyth-Templeton et al., 1997; WO 98/07408). A novel lipid formulation composed of an equimolar ratio of 1,2-bis(oleoyloxy)-3-(trimethyl ammonio)propane (DOTAP) and cholesterol significantly enhances systemic in vivo gene transfer, approximately 150-fold. The DOTAP:cholesterol lipid formulation is said to form a unique structure termed a "sandwich liposome". This formulation is reported to "sandwich" DNA between an invaginated bi-layer or 'vase' structure. Beneficial characteristics of these lipid structures include a positive colloidal stabilization by cholesterol, two dimensional DNA packing and increased serum stability.

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Lipid encapsulation has resulted in a lower toxicity and a longer serum half-life for such compounds (Gabizon et al., 1990). Numerous disease treatments are using lipid based gene transfer strategies to enhance conventional or establish novel therapies, in particular immune therapies.

In certain embodiments of the invention, the lipid vehicle may be complexed with a hemagglutinating virus (HVJ). This has been shown to facilitate fusion with the cell membrane and promote cell entry of lipid-encapsulated DNA (Kaneda et al., 1989). In other embodiments, the lipid vehicle may be complexed or employed in conjunction with nuclear non-histone chromosomal proteins (HMG-1) (Kato et al., 1991).

In yet further embodiments, the lipid vehicle may be complexed or employed in conjunction with both HVJ and HMG-1.

F. PHARMACEUTICAL PREPARATIONS AND ADMINISTRATION

1. Therapeutic Amounts

One of ordinary skill in the art would be familiar with administration of a therapeutic amount of a composition to a subject. Whether a certain amount of a composition is therapeutic depends on the goal of the treating physician. For example, in some embodiments of the present invention, the goal is prevention of pathogen infection. In other embodiments, the goal is suppression of an already infected subject or cell. One of ordinary skill in the art would be familiar with clinical endpoints for measuring response in a subject. An endpoint may be, for example, improvement in clinical symptoms of a previously infected subject, or absence of active symptoms of infection where the goal is prevention.

One of ordinary skill in the art would be familiar with dosing regimens which can be applied in the context of the present invention. For example, the composition may be administered continuously over a defined period of time, such as over 1 hour, at periodic intervals over the course of a day. A course of therapy may last for a period of time as determined by one of ordinary skill in the art.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently be described in terms of plaque forming units (pfu) or viral particles for a viral construct. Unit doses range from $10^3$, $10^4$, $10^5$, $10^6$, $10^7$, $10^8$, $10^9$, $10^{10}$, $10^{11}$, $10^{12}$, $10^{13}$ pfu or viral particles (vp) and higher.

Protein may be administered to a patient in doses of or of at least about 0.01 ng/ml or any amount greater than 0.01 mg/ml.

2. Injectable Compositions and Formulations

Any method of administration of the therapeutic compositions of the present invention is contemplated. One of ordinary skill in the art would be familiar with the wide range of methods of delivery of a therapeutic composition to a subject. For example, the composition may be administered parenterally, intravenously, intradermally, intramuscularly, or even intraperitoneally as described in U.S. Pat. No. 5,543,158; U.S. Pat. No. 5,641,515 and U.S. Pat. No. 5,399,363, which are specifically incorporated herein by reference in their entirety.

Injection of nucleic acid constructs may be delivered by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the some methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

3. Combination Treatments

Certain embodiments of the present invention involve administering to the subject or contacting the cell with at least one additional agent to prevent or suppress the infection of the subject or cell, respectively.

In some embodiments, the MDA-7 therapy is used in conjunction with another antiviral agent. One of ordinary skill in the art would be familiar with the wide range of antiviral agents that are available.

In other embodiments, the MDA-7 therapy is used in conjunction with an agent that prevents or suppresses infection by acting as an immunogenic agent.

The MDA-7 therapy may precede or follow the other agent treatment by intervals ranging from minutes to weeks. In embodiments, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, for example gene therapy is "A" and the immunogenic molecule given as part of an immune therapy regime, such as an antigen, is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the therapeutic expression constructs of the present invention to a patient will follow general protocols for the administration of such compounds, taking into account the toxicity, if any, of the vector. It is expected that the treatment cycles would be repeated as necessary. It also is contemplated that various standard therapies, as well as surgical intervention, may be applied in combination with the described therapy.

In yet another embodiment, the MDA-7 therapy is provided as part of a therapeutic regimen that involves the administration of one or more other forms of gene therapy. Delivery of a vector encoding mda-7 in conjunction with a second vector encoding another agent that can prevent or suppress infection by a pathogen will have a combined inducing effect on target tissues. Alternatively, a single vector encoding both genes may be used.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

The Tumor Suppressor Activity of MDA-7/IL-24 is Mediated by Intracellular Protein Expression in NSCLC Cells Methods 1. Cell Lines and Cell Culture All the tumor cell lines utilized were obtained from American Type Culture Collection (ATCC, Rockville, Md.). The cell lines evaluated were: lung (H1299, A549), prostate (PC3), MCF-7 (breast) and 293 HEK cells. The cells were cultured according to supplier's recommendation. Human umbilical vein endothelial cells (HUVEC) were obtained from Clonetics, (Walkersville, Md.). The cells were free of mycoplasma and were used in the log phase of growth. Cells were harvested with 0.125% Trypsin-1.3 mM EDTA (GIBCO-BRL, Life Technologies, Grand Island, N.Y.). Brefeldin A and Tunicamycin were purchased from Sigma Chemicals (St. Louis, Mo.).

2. Plasmids pSHOOTER expression plasmids (Invitrogen, Carlsbad, Calif.) direct subcloned proteins to the cytoplasm, nucleus, or endoplasmic reticulum (ER). Each vector construct (containing an engineered C-terminal myc tag) was used to subclone mda-7 cDNA. The vector directing proteins to the cytoplasm contains a standard expression vector backbone, while the vectors directing proteins to the nucleus and ER contain signal sequences appropriate to those compartments. The nuclear targeting vector has an N-terminal nuclear targeting signal, while the ER targeting vector has an N-terminal ER signal peptide sequence and a C-terminal ER retention sequence. mda-7 was subcloned into these vectors using PCR to delete both the stop codon and the region encoding the first 48 amino acids, constituting the secretion signal, from full length mda-7 cDNA. PCR was also used to provide restriction sites compatible with the Invitrogen targeting vectors, and in frame with the C-terminal myc tag contained in the vectors.

The primers sequences used for cloning are as follows: forward PCR primer (with SalI site): tttttGTCGACatggc-ccagggccaagaattcc (SEQ ID NO: 3); Reverse PCR primer (with NotI site): tttttGCGGCCGCgagcttgtagaatttctgc (SEQ ID NO: 4). All plasmids were sequenced to confirm orientation and in-frame sequence.

3. Recombinant Adenovirus Production and Gene Transfer

Construction and purification of replication-deficient human type 5 Adenovirus (Ad5) carrying the mda-7 gene was described previously (Mhashilkar et al., 2001). Cell lines were infected with Ad-mda7 or Ad-luc with indicated MOIs. Cells were plated at $10^5$-$10^6$ cells/well in a 6-well plate format for protein expression, trypan-blue exclusion assay or apoptosis assays. For transfection with pShooter vectors, 1 µg of plasmid DNA was used to transfect cells using lipofectamine protocol as described (Mhashilkar et al., 2003).

4. Microarray Analysis

MICROMAX Human cDNA System I—Direct kit (NEN Life Science Products, Inc.) containing 2400 human cDNAs were used. mRNA was isolated from H1299 cells treated with Ad-mda7 or Ad-luc (1000 vp/cell for 24 hr) and analyzed according to manufacturer's instructions.

5. Western Blot Analyses

Cell lysates (105-106 cells) were suspended in 500 µl of Laemmli buffer with 5% 2-mercapto-ethanol (2ME) or supernatants (1:1 mixing with Laemmli buffer+2ME), were analyzed by SDS gel electrophoresis and western blot analysis. Expression of various proteins was determined by using the following primary antibodies: rabbit or mouse anti-human MDA-7 (Introgen Therapeutics, Inc), goat anti-human BiP/GRP-78, rabbit anti-human GADD34, goat anti-human PP2A, goat anti-human PERK, rabbit anti-human XBP-1 (Santa Cruz Biotechnologies, Santa Cruz, Calif.), rabbit anti-human caspase 7 and caspase-9 (Cell Signaling Technology, Beverly, Mass.). Antibodies against beta-actin, and alpha-tubulin were purchased from Sigma. Following incubation with horseradish peroxidase-labeled secondary antibody (Amersham Biosciences, Piscataway, N.J.) the proteins were visualized on enhanced chemiluminescence film (Hyperfilm, Amersham Biosciences, Piscataway, N.J.) by application of Amersham's enhanced chemiluminescence western blotting detection system. All westerns were performed 2-4 times.

6. Production of Recombinant MDA-7 Protein

Secreted MDA-7 protein was purified from the supernatants of MDA-7 baculovirus-infected cells. Briefly, Hi-Five cells (Invitrogen) were infected with MDA-7 baculovirus at an MOI of 5, and supernatants harvested after 72 hours of growth. For purification, polyclonal rabbit anti-MDA-7 antibody was cross-linked to immobilized protein G using the Seize-X Kit (Endogen), and incubated with supernatant at 4° C. for 4 hours. After washing, bound protein was eluted according to manufacturer's instructions, neutralized, and dialyzed against PBS. MDA-7 protein-containing fractions were verified by Western blot and quantified by ELISA. Bacterial MDA-7 was produced by cloning the human mda-7 cDNA (residues 55-206) into the p202 expression vector (kindly provided by Dr. Jim Sacchetini, TAMU). This plasmid expresses a His(6)/Maltose Binding Protein (MBP)/MDA-7 fusion protein after induction with IPTG. Recombinant His(6)-MBP-MDA-7 protein was partially purified with Ni-NTA Agarose resin (Qiagen). The protein was eluted from the column and MDA-7 was released from the His(6)-MBP carrier protein by overnight cleavage with TEV protease. The MDA-7 protein was purified to homogeneity by anion exchange chromatography.

7. Immunofluorescence Assays

Cells were seeded into multi-well chamber slides and transfected with plasmid DNA or transduced with Ad-vectors. Untreated cells served as controls in these experiments. Forty-eight hours after transfection, cells were washed in PBS, fixed with cold ethanol:acetic acid (95:5 vol/vol), and stained for MDA-7 using mouse anti-human MDA-7 antibody and Texas Red-conjugated anti-mouse secondary antibody (Vector Laboratories, Burlingame, Calif.). Slides were mounted using anti-fade mounting reagent (Vector Laboratories) and analyzed using a Nikon Fluorescent microscope. Photographs were taken using a Nikon Digital camera DXM1200 System. All assays were performed at least 3 times.

8. Cell Viability Assays

Cell viability was determined by trypan blue exclusion assay or Live/Dead assay. Cells were trypsinized and a small aliquot was suspended 1:1 volume with 0.1% trypan blue. Total cell numbers and cell viability counts were assessed using a hemocytometer under light microscopy. For Live/Dead assay (Molecular Probes, Eugene Oreg.) cells were plated in chamber slides (Nunc) and then treated with pShooter-plasmid vectors or with Ad- vectors. Two-four days later the cells were treated with the probes, Calcein AM and Ethidium homodimer (both at 5 uM final conc. in PBS), for 30 minutes and then live (green) and dead (red) cells were counted via fluorescence microscopy. All assays were performed at least three times.

9. FACS Analyses and Annexin V Assay

Cells were analyzed for apoptosis using the ApoAlert Annexin V-FITC kit (CLONTECH). Briefly, vector-transduced cells ($10^5$-$10^6$ cells total) were washed extensively in PBS and then incubated with Annexin V-FITC reagent for 30 minutes on ice. Cells were then washed with PBS and processed for FACS analysis and fluorescence microscopy as above. Assays were performed 2-3 times.

10. Statistical Analysis

The statistical significance of the experimental results was calculated using Student's t-test. The level of significance was set at $p<0.05$.

Results

1. Ad-mda7 Induces Apoptosis and Secretion of MDA-7 Protein

The mda-7 coding region possesses an unusually long leader sequence (48 amino-acids). Analysis of the predicted primary amino-acid sequence indicates that the MDA-7 protein contains a prototypic signal sequence, which is likely responsible for directing secretion of the protein (FIG. 1A). The protein also possesses three canonical N-glycosylation sites. Immunohistochemical analyses of H1299 cells treated with Ad-mda7 demonstrate MDA-7 expression in secretory granules (Mhashilkar et al., 2001). MDA-7 expression co-localizes with BiP, a marker for the secretory apparatus. Hydropathicity analysis of the translated protein product demonstrates a strongly hydrophobic region at the N-terminus (Caudell et al., 2002), and analysis of the primary amino-acid sequence predicts cleavage of MDA-7 at amino acid 48, resulting in the secretion of the remaining protein product of amino acids 49-206.

H1299 NSCLC tumor cells were transduced with Ad-mda7 or Ad-luc and analyzed for cytotoxicity. H1299 cells were killed in a temporal- and dose-dependent manner by Ad-mda7 (FIG. 1B). The control Ad-luc vector had no effect on cell viability, whereas even low doses (1000 vp/cell; 40 pfu/cell) of Ad-mda7 caused cell death within 24 hr. Treatment of H1299 cells with Ad-mda7 vector causes high levels of intracellular MDA-7 protein as well as release of MDA-7 protein into the supernatant (FIG. 1C). The soluble MDA-7 is of higher molecular weight than the intracellular form. We have sequenced the MDA-7 protein released from Ad-mda7 transduced cells and have found that the secreted protein starts at amino-acid 49, as predicted. To demonstrate that the MDA-7 protein in the supernatant is derived from an active secretion process rather than resulting from cell lysis, the western blot shown in FIG. 1C was probed with an antibody against beta-actin. Immunoreactive beta-actin was not detected in the supernatant samples, whereas strong signals were obtained from cell lysates. Thus it is very unlikely that the MDA-7 protein is released from cells by a passive mechanism.

High levels of MDA-7 (>100 ng/ml) are secreted from tumor cells (FIG. 1C) after Ad-mda7 treatment. Untreated or Ad-luc treated cells do not show any MDA-7 reactivity. Immunoreactive MDA-7 protein can be detected intracellularly within 12 hours after Ad-mda7 treatment of H1299 cells, whereas secreted MDA-7 is not detected until 24 hr after transduction (FIG. 1C).

2. Ad-mda7 Activates Stress Proteins Associated with UPR (Unfolded Protein Response)

Previous studies have demonstrated that Ad-mda7 transduction of tumor cells results in activation of molecules involved in apoptosis and death signaling pathways (p53, BAX, BAK, TRAIL, c-jun, JNK, caspases, p38, PI3K and beta-catenin) (Mhashilkar et al., 2001; Saeke et al., 2000; Saeki et al., 2002; Pataer et al., 2002; Sarkar et al., 2002; Kawabe et al., 2002; Mhashilkar et al., 2003). Microarray analyses performed on Ad-mda7 treated H1299 cells indicated activation of a number of additional stress-related genes, especially those involved in regulation of protein folding and secretion (TABLE 3).

TABLE 3 demonstrates microarray analysis of Ad-mda7 gene regulation in H1299 cells. Cells were treated with Ad-mda7 or Ad-luc (1000 vp/cell for 24 hr) and mRNA isolated. The samples were used to evaluate mRNA changes in transduced cells by performing microarray analyses using the MICROMAX (NEN) arrays. Analyses of datasets showed regulation of stress and protein folding pathways (n.d.: no data). Ad-mda7 induced protein changes in H1299 cells. Cells were treated with Ad-luc or Ad-mda7 and protein changes in MDA-7 expressing cells relative to control cells were evaluated using western analyses. All assays were performed at least twice.

TABLE 3

MDA-7 Regulates Stress Genes involved in Protein-Folding

| Gene | Function | mRNA change* | Protein change# |
|---|---|---|---|
| Hsp 70-5 | BiP/grp 78 | ↑ 12.8 | ↑ 5 |
| Hsp 90 | ATP-regulated molecular chaperone | ↓ 2.0 | ↑ <1.5 |
| tra 1 | ER heat shock protein (grp 94/gp 96) | ↑ 8.4 | n.d. |
| HSJ1 | Heat shock protein | ↑ 7.7 | n.d. |
| Hsp 60 | Chaperonin | ↑ 1.4 | n.d. |
| Hsp 70-1 | Chaperone | ↑ 1.4 | ↑ <1.5 |
| protein kinase inhibitor p58 | overexpression leads to tumor formation in mice | ↓ 2.7 | n.d. |
| PP2A | Protein phosphatase 2A; ser/thr p'tase | ↑ 2.8 | ↑ 2.5 |

Strong regulation, at a transcriptional level of PP2A, hsp 70-5 (BiP), HSJ1 and tra 1, was noted. Therefore, protein expression of various stress-related molecules (BiP, GADD34, PP2A) was evaluated after Ad-mda7 transduction of H1299 cells (FIG. 2A). Western blot analyses demonstrated consistent increases in steady state levels of proteins for BiP, GADD34 and PP2A after MDA-7 expression. These proteins are implicated in activation of the mammalian stress response known as Unfolded Protein Response (UPR). Additional members of the UPR pathway (caspases 7, 12 and XBP-1) were analyzed. As shown in FIG. 2B, expression of these UPR-associated proteins is up-regulated after Ad-mda 7 transduction, suggesting that UPR activation was the mechanism by which MDA-7 was killing cancer cells. Expression of PERK, another protein characteristic of UPR activation, was evaluated. No detectable levels of PERK in H1299 cells was found. Previous studies have indicated that PERK is expressed in secretory cells, such as beta-islet cells (Zhang et al., 2002), and thus lack of PERK expression in NSCLC H1299 cells is not surprising. It has been previously shown that Ad-mda7 transduction of tumor cells causes activation of mitochondrial caspase 3 and 9 (Saeki et al., 2000). FIG. 2C shows that Ad-mda7 transduction of H1299 cells results in activation (via cleavage) of caspase 7, an important caspase mediating UPR apoptotic responses.

3. MDA-7 is Heavily Glycosylated

The higher molecular weight of the secreted MDA-7 protein, as shown in FIG. 1C, is suggestive of glycosylation, and is consistent with the presence of three predicted N-glycosylation sites in the MDA-7 sequence (FIG. 1A). Glycopeptidase F treatment of the secreted MDA-7 protein results in substantial reduction in protein size (FIG. 3A). The deglycosylated protein runs primarily at 19 kD, consistent with the predicted size of the unmodified protein. Since glycosylated proteins generally acquire sugars during sorting through the endoplasmic reticulum (ER) and Golgi apparatus, the effect of glycosylation and secretion inhibitors on MDA-7 intracellular processing and subsequent secretion was evaluated. Tunicamycin (TUN) inhibits the addition of sugars to proteins within the ER (Yeo et al., 1989), while brefeldin A (BFA) inhibits vesicular transport of proteins from the ER to the Golgi (Magner and Papagiannes, 1998). Both drugs are commonly used to disrupt the secretion of proteins. As shown in FIG. 3B, both TUN and BFA inhibit MDA-7 protein secretion into the medium. Thus, the MDA-7 protein is post-translationally modified and is actively secreted from Ad-mda 7 treated cells. Inhibition of secretion is dose-dependent as 2 μg/ml tunicamycin completely blocks secretion whereas 1 μg/ml tunicamycin reduces secreted MDA-7 by >60%. Secretion of MDA-7 is more sensitive to BFA as even 1 μg/ml is sufficient to completely block MDA-7 secretion. Note that blocking MDA-7 secretion by either drug leads to a substantial accumulation of intracellular MDA-7 (FIG. 3B).

4. Secreted MDA-7 is Not Required for Cell Death in NSCLC Cells

The cytotoxicity induced by Ad-mda7 in the presence of these glycosylation and secretion inhibitors was next evaluated. TUN and BFA levels were titrated until inhibition of secretion of MDA-7 protein was detected. As shown in TABLE 3 and FIG. 3B, treatment of H1299 cells with 2 μg/mL tunicamycin completely blocked secretion of MDA-7 protein, whereas less than 1 μg/ml of BFA was required for this effect. The intracellular MDA-7 protein in TUN treated cells exists as a dominant species at approximately 19 kD, which represents the primary unglycosylated translation product.

Figure 4A:
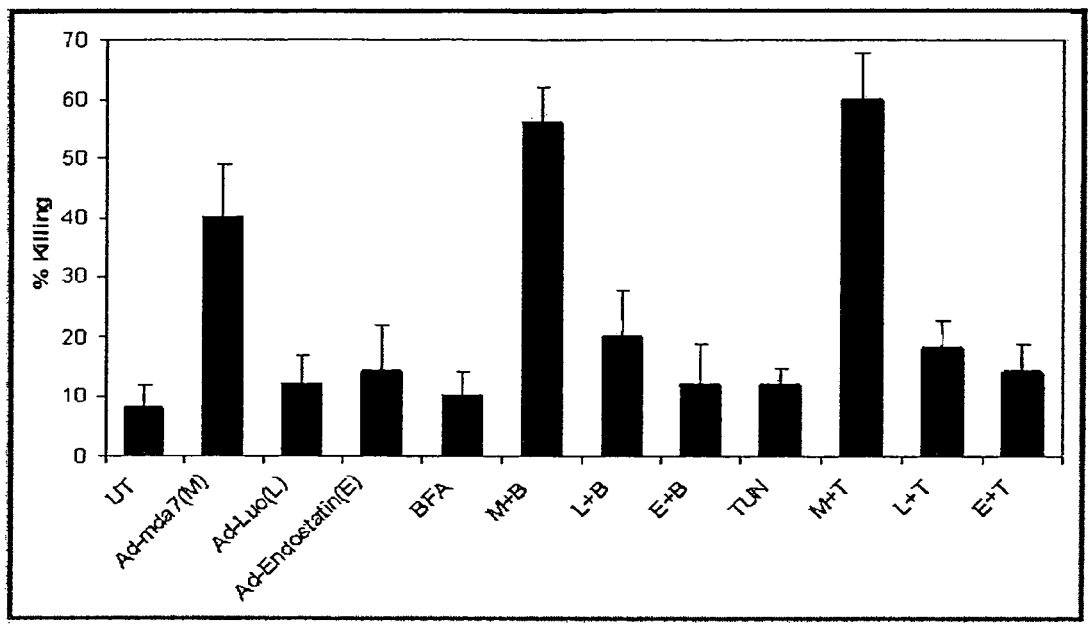
FIG. 4A, FIG. 4B. Inhibition of secretion does not abrogate Ad-mda7 cytotoxicity.

In BFA treated cells, the 19 kD unglycosylated protein is observed, in addition to a higher molecular weight smear indicative of partially mature glycosylated products which are blocked in transport from the ER. Note that no maturation to the 40 kD secreted product is evident. Additional lower molecular weight species are observed; these are likely degradation products. Blocking secretion of MDA-7 using glycosylation inhibitors such as TUN or BFA did not abrogate cell killing by Ad-mda7 (TABLE 3, FIG. 4A). Note that the combination of Ad-mda7 and TUN or BFA slightly enhanced cell killing, even though this dose of tunicamycin or BFA was not cytotoxic. The enhanced killing is likely due to the secretion inhibitor sensitizing cells to death, as has been previously reported (Gething and Sambrook, 1992).

To address whether apoptosis induction is due to intracellular MDA-7 or is simply a non-specific effect due to protein accumulation in the ER, we performed similar experiments using an adenoviral vector encoding endostatin as a control glycosylated secreted protein. Neither BFA nor tunicamycin significantly modulated cell killing due to Ad-luc or Ad-endostatin (FIG. 4A; p>0.05; TABLE 4), although both drugs potently blocked endostatin secretion and caused intracellular accumulation of endostatin protein. Thus, blocking MDA-7 secretion does not abrogate cell killing and apoptosis induction, whereas blocking endostatin secretion has no effect on cell viability.

TABLE 4

Intracellular MDA-7 Mediates Apoptosis in H1299 cells

| Tunicamycin conc. (ug/mL) | MDA-7 Protein Expression | | Tun. Toxicity | Annexin V Apoptosis Ad-mda7 + Tun. |
|---|---|---|---|---|
| | Secreted | Intracellular | | |
| 0 | ++ | ++ | − | 25% |
| 0.1 | ++ | ++ | − | 22% |
| 1.0 | + | +++ | − | 22% |
| 2.0 | − | ++++ | − | 42% |

H1299 cells were treated with 1000 vp/cell Ad-mda7 and the indicated concentrations of tunicamycin. Cells were harvested 24 hr later and analyzed for intracellular and secreted MDA-7 protein by western blot and apoptosis via Annexin V assay. Control cultures of cells treated with only tunicamycin were also assessed for apoptosis (Tun. Toxicity).

Figure 4B:
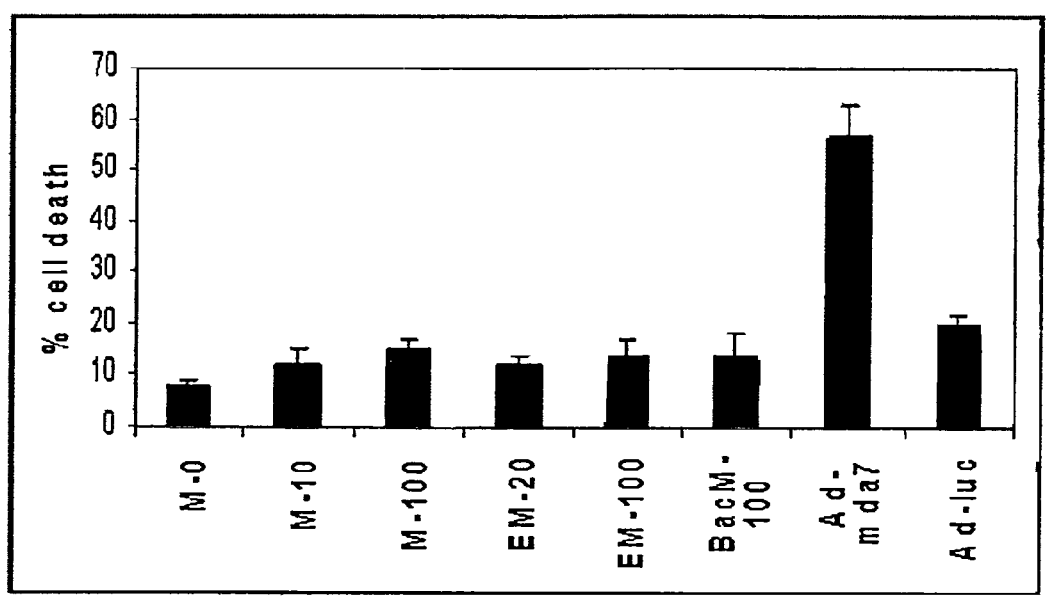

These results suggest that it is the intracellular and not the secreted form of MDA-7 that is primarily responsible for eliciting cell death in H1299 cells. This hypothesis was tested by adding secreted MDA-7 protein to naïve lung tumor cells and monitoring cell death. Initial studies adding supernatant from Ad-mda7 transduced cells did indicate cell death; however careful analysis demonstrated that the cell death was caused by residual Ad-mda7 vector in the culture supernatant. When culture supernatants were treated to minimize Ad-mda 7 contamination, negligible cell death was induced by MDA-7 containing supernatants. To eliminate any confounding aspect of Ad vector toxicity, this study was repeated using MDA-7 containing supernatant from stably expressing 293-mda7 cells applied to tumor cell cultures (FIG. 4B). Insignificant levels of cell death were seen (<10% above background levels) confirming that the secreted MDA-7 was not able to elicit death in H1299 tumor cells (FIG. 4B). In contrast, Ad-mda7 treatment of H1299 cells resulted in >50% cell death. When anti-MDA-7 neutralizing antibody was added to Ad-mda7 infected cultures, no inhibition of cell killing was observed, further demonstrating that the primary killing activity from Ad-mda7 treated cultures was due to intracellular protein. MDA-7 protein made in insect cells using baculovirus vectors (BacM) or bacterially expressed MDA-7 protein (EM) failed to induce significant killing in H1299 cells (FIG. 4B). An additional control included treating H1299 cells with MDA-7 protein and then transducing with Ad-luc to evaluate any interaction between Ad vector signaling and MDA-7. Only background killing was observed, further indicating that the cytotoxicity in Ad-mda7 treated cultures was due to intracellular MDA-7 protein.

5. Subcellular Targeting of MDA-7

Figure 5:
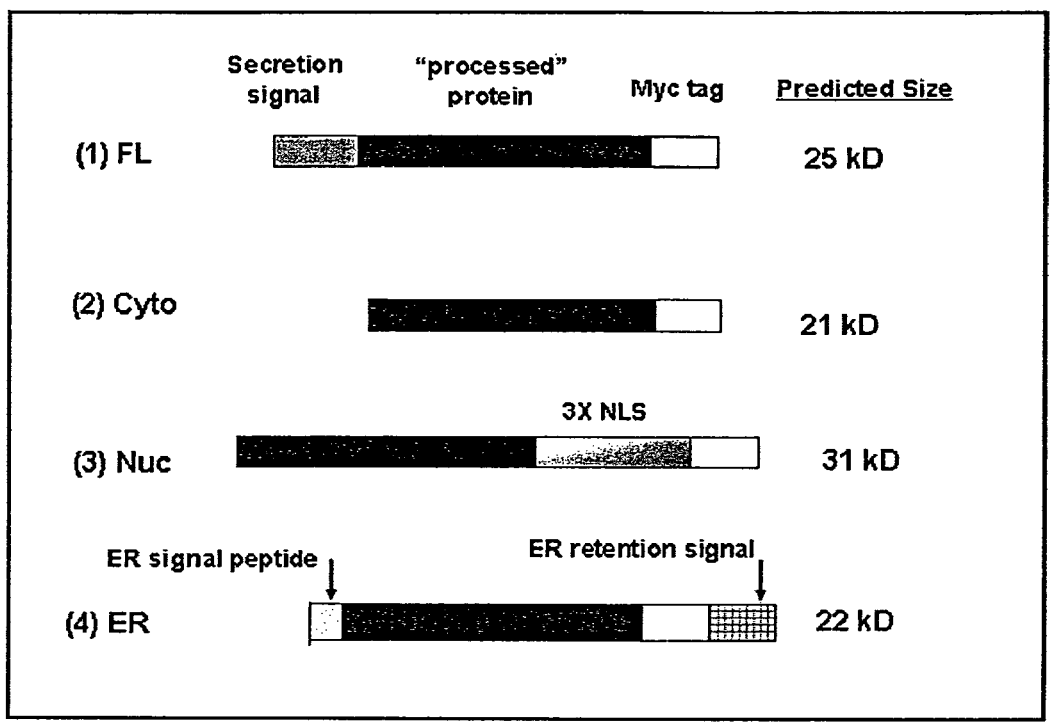
FIG. 5. Subcellular targeting vectors for MDA-7 protein expression. Schematic of plasmid vectors used to re-target MDA-7 protein to subcellular compartments. The MDA-7 signal sequence (aa 1-48); extracellular protein (aa 49-206; "processed protein"); myc tag; nuclear localization signal (NLS); endoplasmic reticulum targeting sequences (ER signal peptide and ER retention signal) are indicated. The predicted sizes of the proteins are indicated. FL: full length; Cyto: cytoplasmic; Nuc: nuclear; ER: endoplasmic reticulum targeted MDA-7.

The question of whether MDA-7 was being released into the cytosol or nucleus during supraphysiologic expression in Ad-mda7 infected cells and whether this was responsible for inducing death was next addressed. To investigate the effects of subcellular localization of MDA-7 protein on cell viability, we constructed expression vectors designed to target MDA-7 expression to different subcellular compartments. In constructing these re-targeting vectors, the secretion signal sequence in the mda-7 cDNA was first deleted and an ATG inserted to generate an initiator codon. As shown in FIG. 5, the nuclear targeting vector contains three nuclear localization signals; the ER targeting vector contains an ER signal sequence and ER retention signal; and the cytoplasmic targeting vector contains no targeting signals, allowing the default expression of proteins in the cytoplasm. The full length (FL) plasmid uses the cytoplasmic targeting vector backbone but contains full length mda-7 cDNA. All proteins expressed by these plasmids also contain a myc tag (2 kD) at the C-terminus.

Figures 6A, 6B:
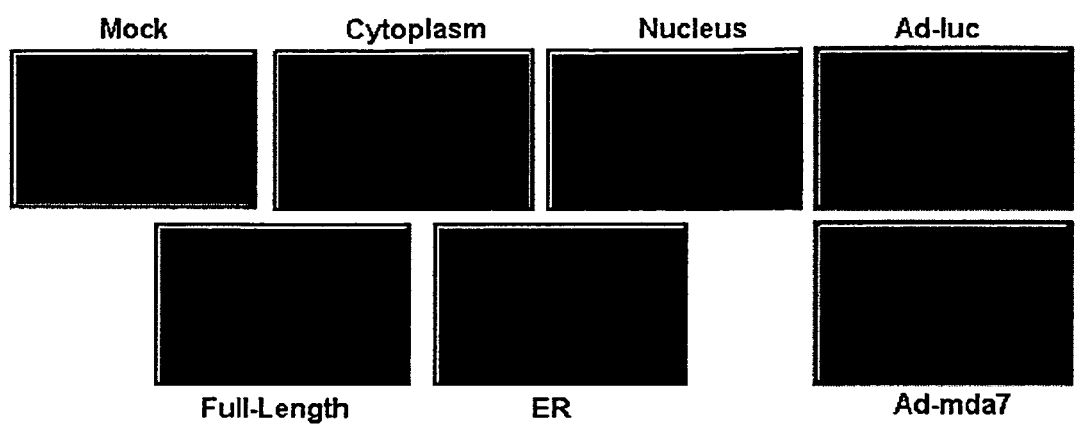
FIG. 6A, FIG. 6B, FIG. 6C. Subcellular expression and activity of MDA-7.

The vectors were transiently transfected into H1299 cells, and subsequent targeted MDA-7 protein expression analyzed by immunocytochemistry. As shown in FIG. 6A, each vector successfully targets MDA-7 protein to the intended subcellular compartment. The MDA-7 protein expressed from the full length plasmid can be seen to be in secretory granules within the cell, similar to the results observed after Ad-mda7 transduction (FIG. 6A). The precise subcellular localization of the targeted proteins was confirmed by comparison with expression patterns of molecules known to reside in these compartments. For example, nuclear targeted MDA-7 co-localized with Hoescht staining of nuclei and ER-targeted MDA-7 co-stained with BiP/grp78. Subcellular localization was also compared to control GFP vectors targeted to the cytoplasm, nucleus and ER. The targeted GFP expression patterns were identical to the targeted MDA-7 staining patterns. FIG. 6A shows that each vector successfully promotes the expression of MDA-7 protein within the correct cellular compartment, while only the full length mda-7 cDNA, which includes the N-terminal secretion signal, permits secretion of MDA-7 protein into the media (FIG. 6B). As predicted, the ER-targeted MDA-7 protein was not secreted as it contained an ER-retention signal.

Addition of the myc tag did not adversely affect MDA-7 protein stability as a control full length mda-7 expression plasmid (without a myc tag) expressed comparable steady-state levels of MDA-7 protein. The myc tag did not appear to interfere with protein processing or secretion as the full length myc-tagged protein showed 2 intracellular MDA-7 bands similar to the full length MDA-7 protein expressed by full length plasmid or Ad-mda7 (FIG. 6B): note that the FL bands are larger due to the myc tag. The myc-tagged MDA-7 appeared to be secreted and glycosylated similarly to native MDA-7 from Ad-mda 7 treated cells (FIG. 6B).

6. Subcellular Localization of MDA-7 Determines Cytotoxicity

Hoechst staining of nuclei was used as a screen to evaluate cytotoxic effects of re-targeted MDA-7 expression. Nuclear or cytoplasmic targeted MDA-7 expression had no effect on nuclear morphology. Cells containing FL and ER-localized MDA-7 protein, however, had disrupted nuclear morphology indicative of apoptosis. To determine the anti-tumor effects of targeted MDA-7 protein expression, cell viability, apoptosis induction and colony formation activity in a panel of tumor cell lines was evaluated.

Figure 6C:
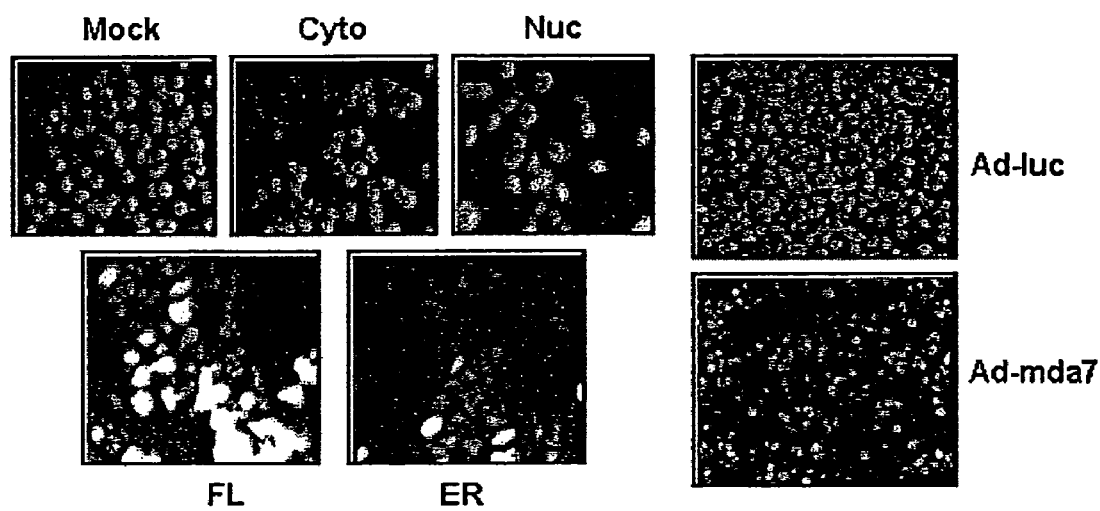

Cell viability was assessed using a fluorescence-based assay, which uses calcein staining to identify viable cells (green). When cells die, they become membrane permeant and take up EtBr dye and stain red. Transient transfection of plasmid constructs into H1299 lung cancer cells demonstrated high level expression of targeted MDA-7 proteins (FIG. 6B). No cytotoxicity was observed in mock, cytoplasmic or nuclear targeted MDA-7 expressing cells. However FL and ER targeted MDA-7 showed significant cytotoxicity (red cells; $p<0.01$ compared to mock, cytoplasmic or nuclear-targeted constructs)—see FIG. 6C.

Figure 7D:
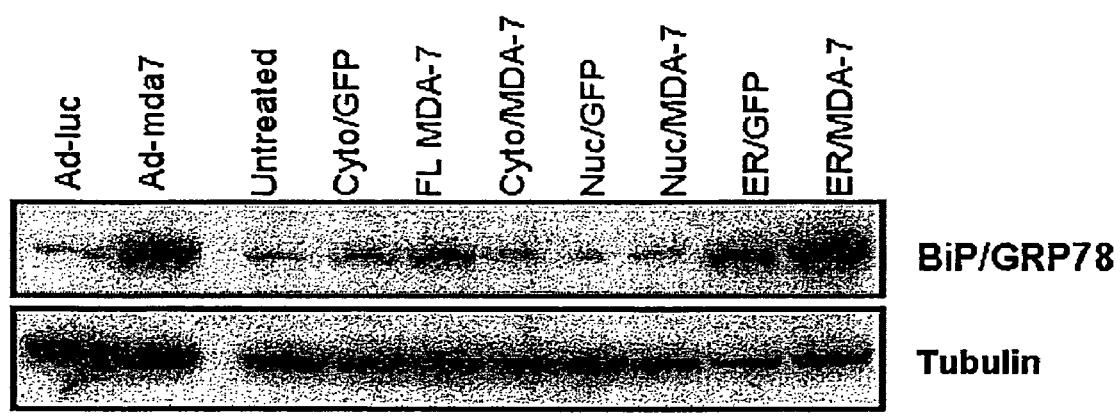

The targeted mda-7 expression constructs incorporate a neomycin resistance marker and were stably transfected into various tumor cell lines and assessed for colony formation (FIG. 7A). Neither nuclear nor cytoplasmic mda-7 expression constructs had a significant effect ($p>0.05$) on the formation of stable transfectant colonies. Full length, secreted MDA-7 and ER-targeted MDA-7 caused a reduction in colony formation, indicating the lethality of MDA-7 in these environments. ER-targeted MDA-7 caused a greater reduction in colony formation than FL MDA-7 ($p<0.01$). Similar results were observed in H1299 and A549 NSCLC, 293 HEK and MCF-7 breast cancer cells. Transiently transfected cells were then evaluated for cell viability and apoptosis induction. H1299 cells were transiently transfected with the MDA-7 targeting plasmids and control GFP targeting plasmids. Only cells expressing FL or ER MDA-7 showed loss of viability and significant cell killing ($p<0.01$; FIG. 7B). The mechanism underlying this cytotoxicity was evaluated by assessing cells for apoptosis. Cells expressing nuclear or cytoplasmic MDA-7 did not exhibit significantly increased apoptosis compared to mock transfected cells ($p>0.05$; FIG. 7C). Both full length and ER-targeted MDA-7 showed significantly higher levels of apoptosis than mock, nuc or cyto vectors ($p<0.01$; FIG. 7C). Thus expression of MDA-7 in the ER or the secretory pathway (FL) results in significant apoptosis induction. The GFP-targeted plasmids did not cause cell killing (FIG. 7B) or apoptosis. BiP expression as a marker of UPR in cells transiently transfected with the MDA-7 or GFP targeting plasmids was then evaluated. Only ER-targeted MDA-7 and full length MDA-7 were able to induce BiP expression in transfected cells. Note that ER-GFP did show some BiP induction, but ER-targeted MDA-7 produced significantly higher BiP induction (FIG. 7D). ER-targeted MDA-7 caused greater BiP induction than FL MDA-7 and was comparable to Ad-mda 7.

Example 2

Immune Activation in Patients with Advanced Cancer Treated with Intratumoral Injection of AD-mda7

Materials and Methods

1. Clinical Protocol.

An open-label, Phase I, dose-escalation study was conducted to evaluate safety and determine the MTD of the adenovirus-mda-7 construct, INGN 241, when administered intratumorally to advanced cancer patients. The pharmacokinetics of INGN 241 DNA, MDA-7 protein, and the humoral immune response to INGN 241 were evaluated in order to better understand their effects on both safety and efficacy.

Eligible patients with defined entry criteria were enrolled into one of 8 treatment cohorts (TABLE 5) and the dominant, symptom-causing tumor was identified and treated as the indicator tumor.

TABLE 5

Patient Cohorts and Treatment Profile

| Cohort no (no. of pts) | No. of Viral Particles | Biopsy time | Diagnosis of Evaluable Pateints[1] (no. tested) |
|---|---|---|---|
| 1 (1) | $2 \times 10^{10}$ | +24 hrs | BrCa (1) |
| 2 (1) | $2 \times 10^{11}$ | +24 hrs | CoCa (1) |
| 3 (3) | $2 \times 10^{12}$ | +24 hrs | SCCHN (1), Mel (1), LCL (1) |
| 4 (3) | $2 \times 10^{12}$ | +48 hrs | BrCa (1), CoCa (1), ChCa (1) |
| 5 (2) | $2 \times 10^{12}$ | +96 hrs | BrCa (1), Mel (1) |
| 6 (1) | $2 \times 10^{12}$, divided dose | +48 hrs | Mel (1) |
| 7 (5) | $2 \times 10^{12}$ | Day 30 | TCC (1), Mel (1), CoCa (1), SCCHN (2) |
| 8 (5) | $2 \times 10^{12}$; twice weekly × 3 | Day 30 | Mel (3), SCCHN (2) |

[1]BrCa, breast carcinoma; CoCa, colon carcinoma; SCCHN, squamous cell carcinoma of the head and neck; Mel, melanoma; LCL, large cell lymphoma; ChCa, cholangiocarcinoma; TCC, transitional cell carcinoma.

The first two cohorts (1 patient each) received $2 \times 10^{10}$ virus particles (vp) or $2 \times 10^{11}$ vp (cohort 2). Excisional biopsies were obtained at 24 hours post treatment. Cohorts 3, 4 and 5 (3 patients per cohort) received $2 \times 10^{12}$ vp, and had excisional biopsies at 24 hours (cohort 3), 48 hours (cohort 4), and 96 hours (cohort 5), respectively. Each resected lesion was serially sectioned and analyzed to determine the radius of diffusion of injection solution, distribution and concentration of the viral agent, transgene protein expression, and the resulting biologic outcome. One patient was enrolled into cohort 6 and receive $2 \times 10^{12}$ vp in divided doses administered to different sections of the indicator tumor and excisional biopsies were obtained at 48 hours.

To assess longer term effects of MDA-7 expression, 5 patients with unresectable disease were entered into cohort 7, who receive $2 \times 10^{12}$ vp and underwent incisional or core biopsies at pretreatment and at 30 days post treatment. Cohort 8 included 5 patients who received single injections of $2 \times 10^{12}$ vp twice a week for 3 weeks (total of 6 injections per cycle). All patients were analyzed throughout the trial for development of toxicity that may be related to either the agent or the injection. The clinical protocol was approved by the US Oncology Institutional Review Board (IRB). All human subjected-related protocols for laboratory analyses that were performed at Baylor University Medical Center were reviewed and approved by the IRB for Human Protection at Baylor University Medical Center.

2. INGN 241

INGN 241 comprises a replication defective Ad5 backbone with E1 and partial E3 deletions. An expression cassette comprising the CMV IE promoter, the wild type mda-7 transgene ORF and the SV40 polyadenylation sequence were cloned into the E1 region of the construct. Vector was double-plaque-purified and correct sequence confirmed as described (Mhashilkar et al., 2001). Clinical material was prepared under cGMPs and complies with guidances for testing for freedom from adventitious agents. INGN 241 was provided as a frozen vial suspension (3.0 m, $1 \times 10^{12}$ vp/ml) in a neutral buffer containing saline and 10% glycerol. The vials were thawed to ambient temperature and mixed with a tracking dye (Isosulfan blue) immediately prior to injection.

3. Immunohistochemical Analysis

A previously described automated immunoperoxidase staining technique (Nemunaitis, 1998) was used to characterize MDA-7 protein expression. Briefly, serial sections of formalin-fixed, paraffin-embedded tissue block were deparaffinized in xylene and graded alcohols, then incubated with 1% $H_2O_2$ with appropriate washings. Antigen retrieval was carried out with 0.01 M citrate buffer in the microwave, followed by incubations in $H_2O_2$ in methanol, 0.05% Triton-X 100 washed in phosphate buffered saline (PBS), and normal goat serum. MDA-7 expression was determined with the avidin-biotin-complexed immunoperoxidase reaction (DAB detection kit, Ventana Medical System) following initial incubation with affinity-purified rabbit anti-human MDA-7 antibody (Introgen Therapeutics), using the Ventana 320ES System (Ventana Medical Systems, Tucson, Ariz.). The reaction was compared with a negative control antibody stained slide and graded in a blinded fashion as negative (−), weak ("+", ≦25% positive cells), moderate ("++", 26-50% positive cells), or strong ("+++", >50% positive cells). Ad-mda 7 transduced cells were used as a positive control.

Determinations of beta-catenin and iNOS expression were carried out in the same manner, following treatment with the relevant primary antibody (mouse anti-human β-catenin antibody C19220, 2.5 ug/ml, BD Biosciences; mouse anti-human iNOS monoclonal antibody N32020, 5 ug/ml; BD Pharmingen).

4. Quantification of Apoptosis by TUNEL

A TUNEL method (DeadEnd Colorimetric Apoptosis Detection Systems, Promega) was used to detect DNA fragmentation in situ. Briefly, tissue sections were deparaffinized in xylene/graded alcohol, and fixed with in 4% paraformaldehyde in PBS before and after proteinase K treatment (20 μg/ml, 15 min, 23 C). An in situ Tdt (terminal deoxynucleotidyl transferase) reaction was carried out with biotinylated nucleotides according to manufacturer's protocols. Apoptotic cells were identified by light microscopy as cells with definitive brown staining in the nucleus that were rounded or shrunken.

5. Serum Cytokine Analysis

ELISA assays (R&D Quantikine kits, Minneapolis, Minn.) were used to quantify patient serum cytokine levels at defined time points before and after treatment as described previously (Nemunaitis '01). Briefly, patient peripheral blood was collected by venipuncture. Serum samples were extracted after clotting and stored at −80° C. Serial serum samples from the same patient were analyzed simultaneously, using cytokine-specific immunoassay reagents according to manufacturer's protocols. The colorimetric reaction was quantified as a function of OD absorbance at 540 nm (SpectraMax 340, Molecular Devices, Sunnyvale, Calif.). Cytokine concentration was calculated according to a reference standard curve and OD values of known, graded concentrations of the recombinant cytokine. The minimal detectable concentration, defined by OD readings at ≧3-fold higher than background, is as follows: IFNγ: <3 pg/ml; TNFα: <4 pg/ml; IL-13β: <1 pg/ml; IL-10: <2 pg/ml; IL-2: <7 pg/ml; IL-6: <0.7 pg./ml; GM-CSF: <3 pg/ml. The % increase in cytokine level at any time point post-treatment was determined through comparison with the baseline level in serum harvested before INGN 241 injection. Based on inter- and intra-sample variations, increases in cytokine level of ≧50% over baseline were considered significant.

6. Flow Cytometric Immunophenotype Analysis

Peripheral blood immunophenotype analysis was carried by a two color immunofluorescence reaction and flow cytometric analysis as described previously (Zhang, 2000). Briefly, patient or normal healthy donor peripheral blood was collected by venipuncture. 100 μl of whole blood was treated with 20 μl of the following reactant mixtures in order to determine the frequency distribution of T, B and NK cell subsets: CD45-FITC/CD14-PE, CD3-FITC/CD19-PE, CD4-FITC/CD8-PE, CD13-FITC, CD20-FITC, CD56-FITC (all from BD Biosciences). The reactants were fixed with 1% paraformaldehyde before flow cytometric analysis (Becton Dickinson FACScan) with the CELLQUEST software (Becton Dickinson).

7. Anti-Adenovirus Antibodies

Serum samples were evaluated for anti-Adenovirus type 5 antibodies using an indirect immunofluorescence assay to detect humoral immune responses against vector as previously reported (Nemunaitis et al., 2000). Post-treatment samples were compared to based one pre-treatment anti-Ad antibody titers (defined as 1).

8. Detection of Viral DNA and RNA

Tumor samples were evaluated for the presence of INGN 241 DNA, mRNA expression from INGN 241, and the expression of a panel of cytokine genes using real-time PCR, TaqMan chemistry, and the ABI Prism's 7700 Sequence Detection System. A real-time PCR method was developed to target the junction of the vector CMV promoter with the 5' end of mda-7 cDNA. Each specimen's DNA was analyzed in duplicate reactions containing 100 ng total DNA. A third reaction was spiked with 100 copies of the target to check for inhibitors of the PCR. INGN 241 derived RNA was measured using a two-step RT-PCR method. First, cDNA was generated from total tumor RNA in a reverse transcription reaction primed with random hexamers. The cDNA was then amplified using the INGN 241 qPCR assay. The number of copies of INGN 241 transcripts per microgram of total RNA was calculated using a standard curve of INGN 241 in vitro runoff transcripts. The expression of tumor mRNAs for human interleukin 6, interleukin 10, and interferon-gamma was determined using Applied Biosystems assay reagents. Expression of each cytokine was analyzed relative to the expression of human GAPDH.

9. INGN 241 qPCR assay primers and probe sequences
Forward Primer: CCCGTAATAAGCTTGGTACCG (herein designated SEQ ID NO: 5).
Reverse Primer: TAAATTGGCGAAAGCAGCTC (herein designated SEQ ID NO: 6).
Probe: -FAM-TGGAATTCGGCTTACAAGACATGACTGTG-TAMRA (herein designated SEQ ID NO: 7).

Results

1. Transgene Expression Following Intratumoral Injection with INGN 241

Patients were stratified into 8 cohorts according to viral dose ($2 \times 10^{10}$ to $2 \times 10^{12}$), time for post-treatment biopsy (24 h to 30 days), and treatment mode (single, divided dose or multiple injections) as described above (see TABLE 5). To better understand the safety and efficacy of INGN 241 treatment, cell and molecular analyses were performed to characterize transgene expression and pharmacokinetics, biologic activity, and immune response.

Figure 8A:
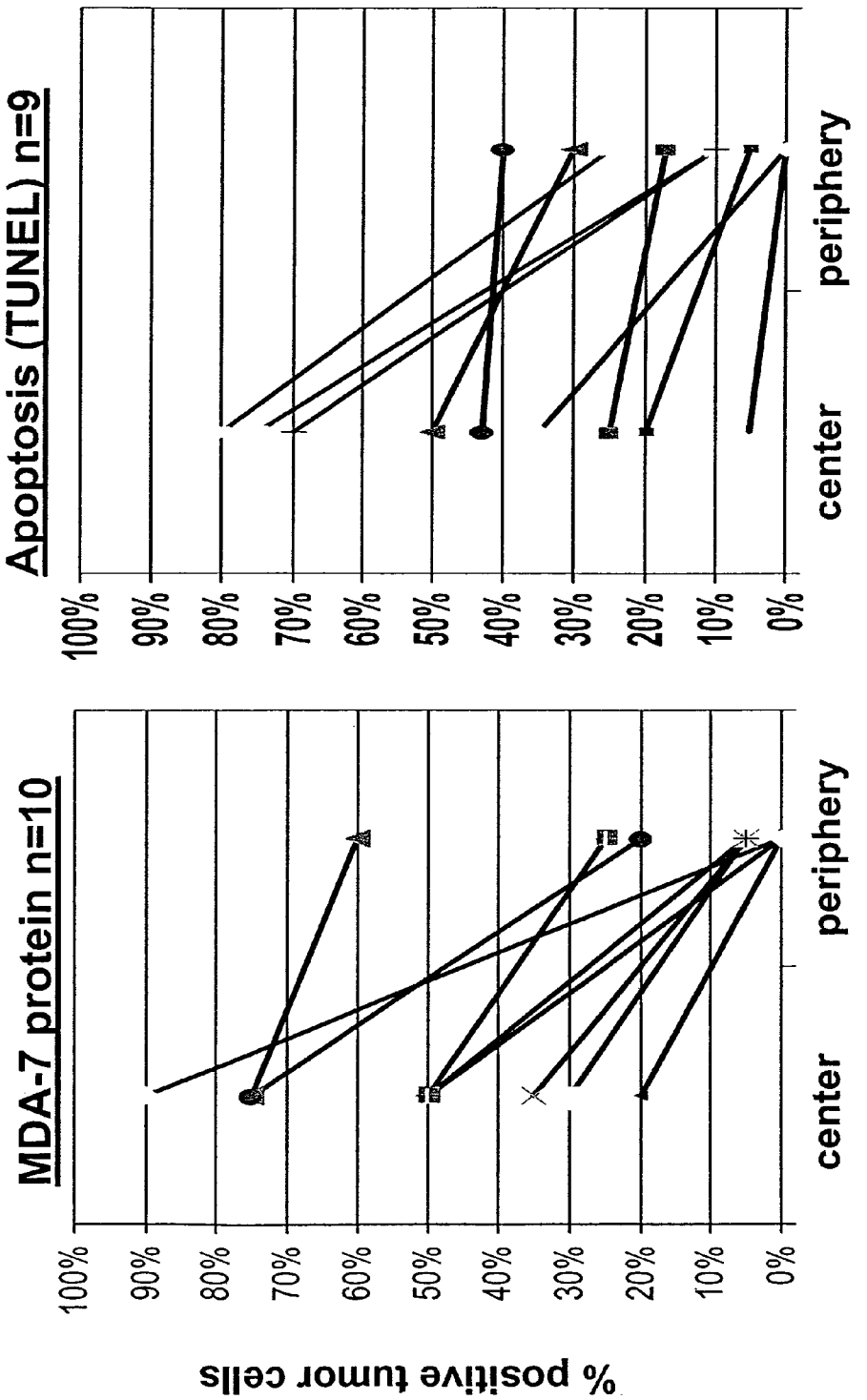
FIG. 8A, FIG. 8B.

For patients entered into cohorts 1-6, the vector treated tumor was resected at 24-96 hours post-injection. Serial sections were evaluated for vector penetration and biologic outcome. All pretreatment biopsies were MDA-7 negative by IHC. All INGN 241 injected lesions showed high levels of MDA-7 immunoreactivity in the center (injection site). Signal intensity was reduced at the periphery, although 6 of 8 lesions still showed MDA-7 immunoreactivity (FIG. 8A). At 24 hours post-injection, the mean proportion of tumor cells expressing MDA-7 protein ranged from 20% in cohort 1 patients who received $2 \times 10^{10}$ vp to a mean of 53% in cohort 3 patients who received $2 \times 10^{12}$ vp.

Figure 8B:
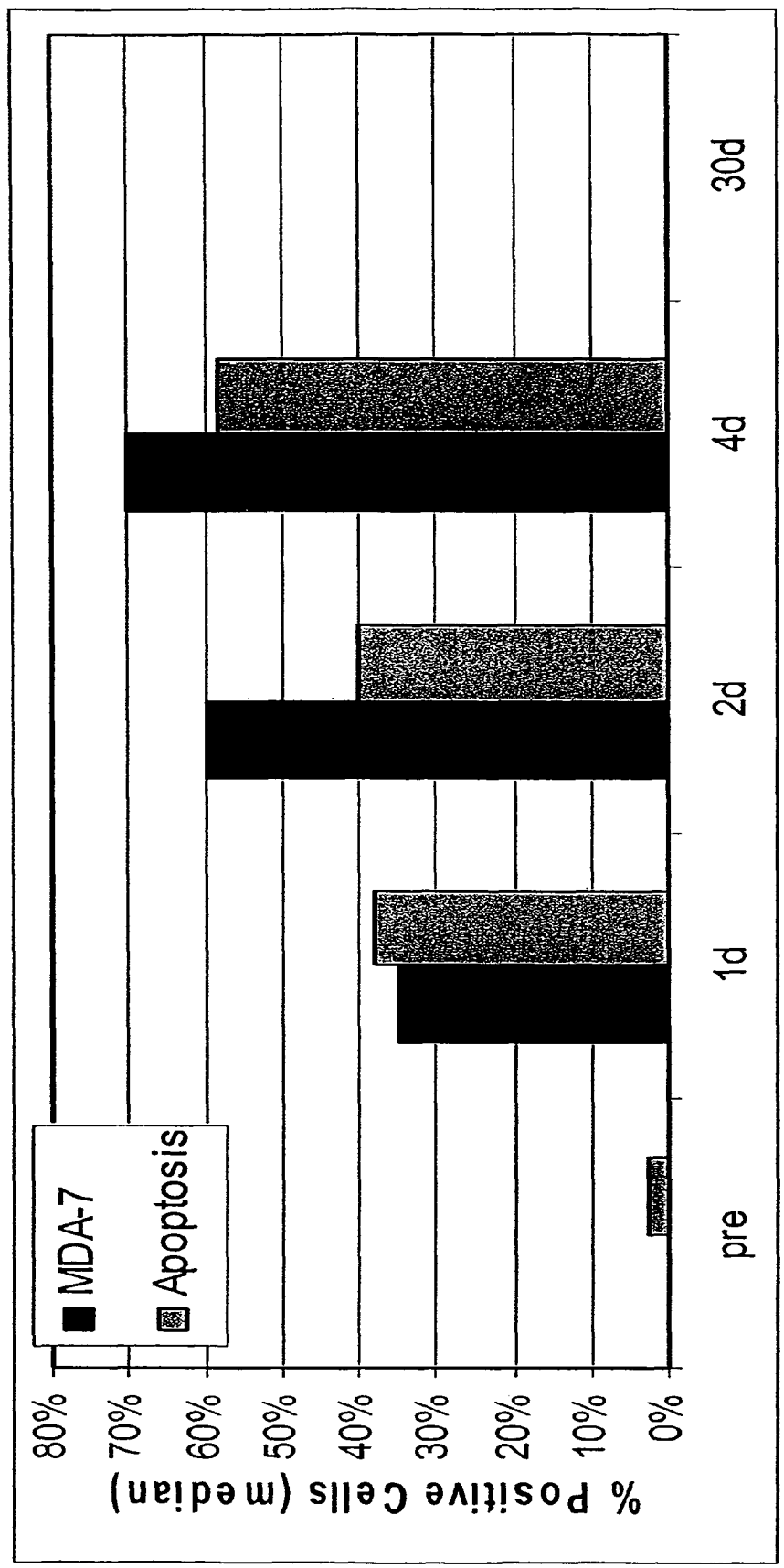

Cohorts 3-5 received the same intratumoral viral dose ($2\times10^{12}$ vp) whereas the injected tumor was biopsied at 24, 48, and 96 hrs respectively. This limited analysis with 2-3 patients per time point nonetheless illustrated the sustained expression of the MDA-7 protein (FIG. 8A), where a median frequency of 70% transgene-positive tumor cells was observed at 96 hours post-injection. MDA-7 staining was not detected in samples obtained at 30 days (FIG. 8B). Quantitative DNA PCR analysis for vector genomes demonstrated a correspondingly high level of viral DNA (740-900 copies per cell) in the injected lesions at days 1 and 2, which markedly decreased at 4 days post-injection (1 copy/cell) (Cunningham et al., 2003). RT-PCR analysis of biopsy slices at the point of injection verified the presence of the INGN 241 viral message at approximately $1\times10^7$ copies/µg at day 1 (cohort 3), $1.2\times10^6$ copies/µg at day 2 (cohort 4), and $8\times10^4$ copies/µg at day 4 (Cunningham et al., 2003).

2. Tumor Apoptotic Activity Correlated with MDA-7 Penetration

Pronounced apoptotic activity was observed in INGN 241-injected tumors in areas of MDA-7 expression, when the injected lesions were resected after 24-96 hours Apoptotic induction was highest in the high dose group ($2\times10^{12}$ vp) and could still be detected at the tumor periphery in 4 of 6 evaluable patients (FIG. 8A). The low dose tumors also exhibited apoptosis at the injection site, but signal at the periphery of these tumors was lower than pre-treat samples. Similar to the MDA-7 distribution, apoptotic activity appeared to accumulate with time in patients who received $2\times10^{12}$ vps, where 36%, 39%, and 58% of total tumor cells revealing a positive TUNEL reaction at 24 hrs (n=3), 48 hrs (n=3), and 96 hrs. post-injection (FIG. 8B).

To correlate apoptotic induction with MDA-7 expression, TUNEL reactions in serial sections from individual injected tumors were contrasted with their pattern of MDA-7 immuno-histochemical reactivity. A graded pattern of MDA-7 expression was consistently observed, with up to 90% of MDA-7-positive tumor cells at the site of injection. Peripheral sections generally displayed proportionately decreased MDA-7 expression (0-25%). The frequency of apoptosis displayed a similarly graded pattern which correlated with MDA-7 expression (FIG. 8A; p<0.01, n=9). These findings indicate that INGN-241 expression contributed significantly to post-treatment tumor apoptosis.

3. INGN 241 Pharmacokinetics

Further evaluations of intratumoral INGN-241 pharmacokinetics were carried out by quantifying vector DNA recovered from serial sections of injected tumors, and the presence of viral DNA in plasma of patients over time. The total number of vector DNA copies in the tumor was compared with total vector injected to yield the % vector recovered from tumor as a function of time. 11.7% of total viral DNA remained in the injected tumor lesion after 24 hours, which was reduced to 1.7% and 0.03% of input load at days 2 and 4. Circulating INGN 241 vector was evaluated in patient serum using quantitative DNA PCR. INGN 241 vector DNA was transiently detected in plasma in both a dose and time dependent manner. INGN 241 was detectable in plasma within 30 minutes after intratumoral injection in all patients analyzed. In cohort 1 and 2 patients, plasma vector was undetectable by 24 hr whereas higher doses of vector were not cleared until 24-72 hr post-injection. In all patients evaluated, circulating vector was no longer detectable after 72 hours. The maximal amount of injected vector detected in the circulation constituted approximately 3% of the intratumorally injected dose. The level of circulating viral DNA in patient plasma represented 0.0025% ($5.1\times10^7$ vp/ml in an estimated total plasma volume of 3 liters) of input load, based on DNA decay analysis.

4. Molecular Outcome of Intratumoral INGN-241 Treatment

Immunohistochemical evaluations were carried out to quantify β-catenin and iNOS expression in INGN 241-treated lesions. Four patients in cohorts 1-5 were diagnosed with metastatic breast cancer at the time of treatment. Their untreated tumors displayed a uniform, diffuse nuclear/cytoplasmic pattern of β-catenin expression. Three cases underwent a distinct redistribution of this protein to the plasma membrane post-treatment. While β-catenin redistribution was not evident in other non-breast tumors examined, the majority of these cases (6 of 8 tested) exhibited a significantly decreased level of beta-catenin expression following intratumoral INGN 241 (TABLE 6).

TABLE 6

β-Catenin Expression in INGN-241-Treated Patient Specimens

| | | Effect of Treatment on on β-Catenin Expression | |
|---|---|---|---|
| Cohort | Patient/Dx | Redistribution to membrane | Decreased expression |
| 1 | 1/BrCa | Yes | No |
| 2 | 2/CoCa | ? | Yes |
| 3[1] | 3/SqCa | ? | Yes |
| 4 | 6/BrCa | Yes | No |
| | 7/AdrCor Ca | n/a | Yes |
| | 8/Chol Ca | Yes | n/a |
| 5 | 9/BrCa | n/a | n/a |
| | 10/JRG; Mel | No | Yes |
| | 12/BVR; Mel | Yes | Yes |
| 6 | 13/MHH; BrCa | Yes | Yes |
| No. positive/no. evaluable | | 5/8 | 6/8 |

[1]Patient 4 was not examined due to lack of specimen. Patient 5 was diagnosed with large cell lymphoma which did not express β-catenin.

By comparison, it is unclear whether INGN-241 treatment altered iNOS expression substantially in an array of tumor types. However, 2 of 2 melanoma cases from cohorts 1-6 exhibited decreased iNOS expression post-treatment. iNOS has been reported as a putative prognostic marker in melanoma and recent studies have shown that Ad-mda7 and secreted MDA-7 protein can down-regulate iNOS expression in melanoma tumor cells via regulation of IRF-1/IRF-2 signaling. Altogether, 4 of 9 cases of various solid tumor types showed a decrease of iNOS following INGN-241 treatment.

5. Immune Activation by INGN-241

Figure 9:
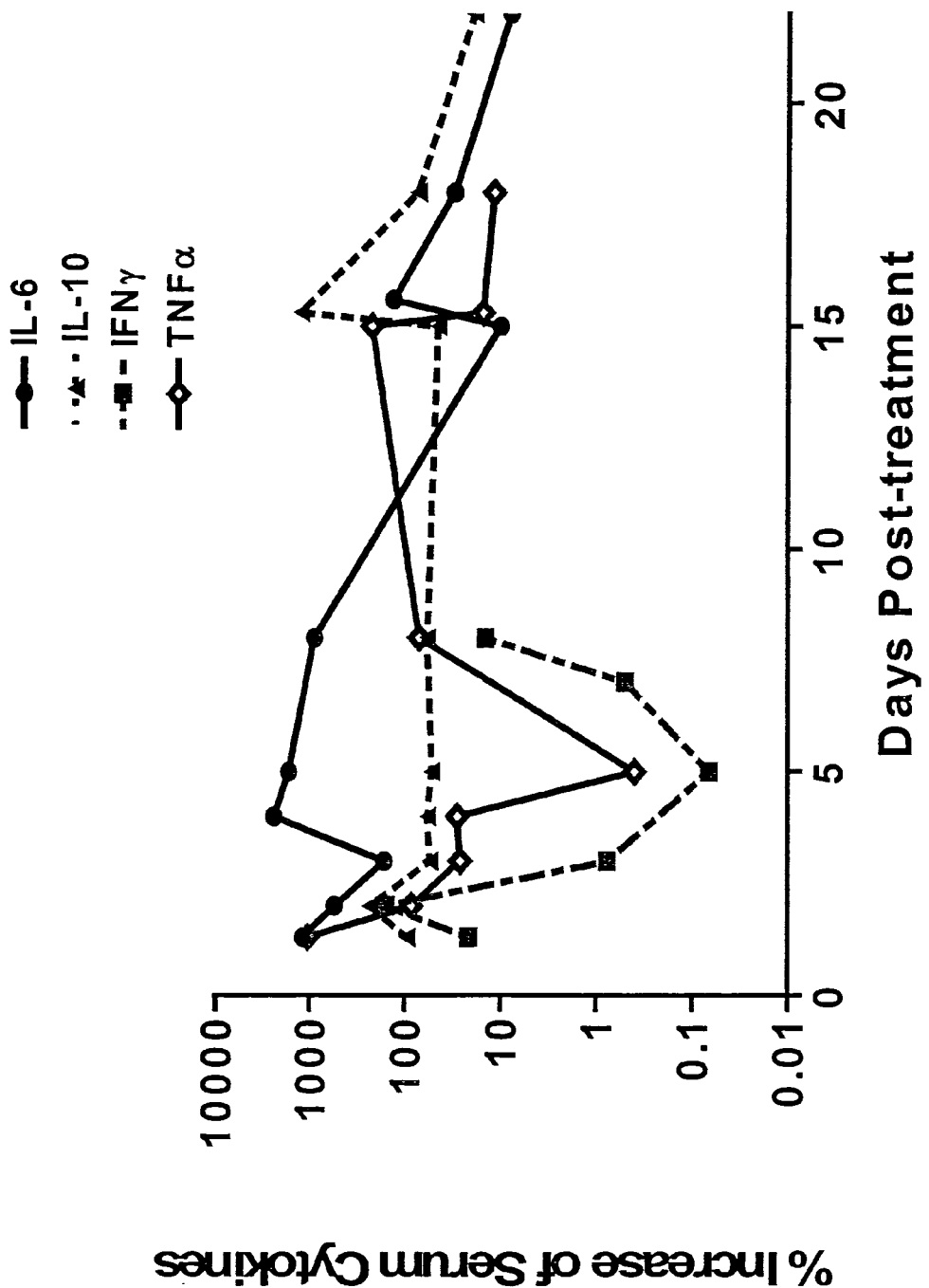
FIG. 9. Pharmacokinetics of serum cytokine response. INGN 241 injection induces cytokine activation. Serum cytokine level of individual patients was determined by an ELISA assay and compared with baseline value to establish the percent increase at the indicated time point post-injection. Value represents mean % increase (±SEM) for the 21 patients who completed the trial. Data for days 15-18 were derived only from cohort 8, who received a second INGN-241 injection on day 14.

To identify systemic immune activation events following intratumoral INGN 241, serum cytokines were quantified at various times after INGN 241 injection. The majority of patients had significantly elevated levels of serum IL-6 (18 of 21 patients), IL-10 (19/21) and TNFα (12/21) following INGN 241 injection. Some of the patients demonstrated increased levels of IFNγ (8/21), GM-CSF (4/21) and IL-2 (2/21) that were ≧50% higher than baseline level within 8 days post-injection. Post-treatment levels of IL-6, IL-10 and IFNγ constituted up to 20-fold higher than pretreatment level. The initial peak responses of IL-6 and TNFα responses occurred at 6 hours post-treatment for most patients, whereas maximal INFγ and IL-10 responses occurred at day 2 post-injection (FIG. 9). For cohort 8 patients who received biweekly repeat injections, cytokine responses did not appear to be significantly heightened as compared with time of initial exposure.

Further analysis was carried out to characterize cytokine response of the 4 patients who responded clinically to INGN-241 (pts 83, 84, 87, 88). Responding patients exhibited significantly higher increases in TNFα (0-22,617%, n=4, vs. 0-161% in non-responders, n=17; p=0.015, df=19) and IL-6 (0-16,636%, n=4; vs. 0-25,85%, n=17; p=0.028, df=19) at 6 hours post-injection, while no significant difference was evident with respect to IL-10 (p=0.3) or IFNgamma (p=0.2) expression in the patient subsets.

Figure 10:
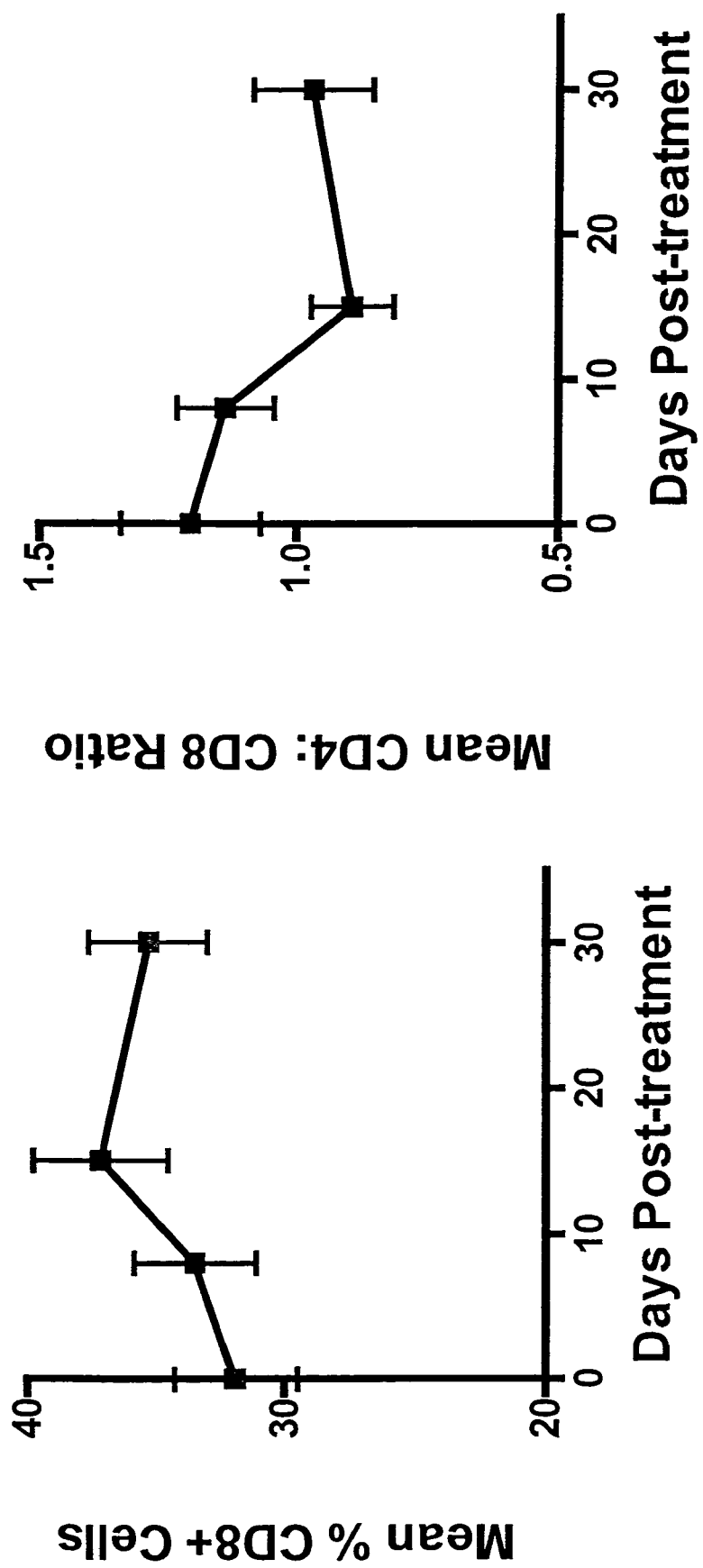
FIG. 10. Effect of Ad-mda7 intratumoral injection on the frequency of peripheral blood CD8+ cells. The frequency distribution of peripheral blood CD3+CD8+ mononuclear cells was determined by two color immunofluorescence flow cytometric analysis. Value represents mean frequency (±SEM) for all patients tested at the indicated time points. The patients' relative frequency of CD3+CD4+ and CD3+CD8+ T cells was represented as a CD4:CD8 ratio. Mean ratio (±SEM) for all patients tested at each time point shown.

For patients who received $2\times10^{11}$ or $2\times10^{12}$ vps, 10 of 21 exhibited an increase in the post-treatment frequency of CD3+CD8+ peripheral blood T cells. Despite the interpatient variation of the frequency distribution of CD8+ T cells before treatment, there was a significant elevation in % CD8-positive T cells (P<0.03, df=40) at day 15 post-injection (from mean pretreatment level of 31±2.4% to 38±2.6% at day 15) (FIG. 10). This increase in CD3+ CD8+ T cells frequency was confirmed by the corresponding increase in absolute CD8+ cell numbers (p=0.02, df=40 at day 15) and was similarly distributed among cohorts receiving single or multiple INGN-241 injections. The ratio of CD4:CD8 cells at each analytic time point was calculated. As a whole, pretreatment CD4:CD8 ratios for the patient cohorts were markedly below the normal value of 2, reflecting the lower than normal frequency of CD4+ T cells that we previously observed in advanced cancer patients (Tong, 2000). In this study, the increase in CD8+ T cells paralleled significantly the reduced CD4:CD8 ratio post-treatment (from 1.2±0.1% at day 0 to 0.9±0.07% at day 15; p<0.03) (FIG. 10).

14 patients in cohorts 1-7 were tested for the presence of anti-adenoviral antibodies. All had elevated antibody titers post-treatment that increased exponentially with time, with a median titer that was 64-fold higher than pre-treatment level at day 15 post-injection.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,554,101
U.S. Pat. No. 4,797,368
U.S. Pat. No. 5,028,592
U.S. Pat. No. 5,139,941
U.S. Pat. No. 5,399,363
U.S. Pat. No. 5,466,468
U.S. Pat. No. 5,543,158
U.S. Pat. No. 5,641,515
U.S. Pat. No. 5,846,225
U.S. Pat. No. 5,846,233
U.S. Pat. No. 6,326,466
U.S. application Ser. No. 09/615,154
U.S. application Ser. No. 10/017,472
Aksentijevich et al., *Hum. Gene Ther.*, 7(9):1111-1122, 1996.
Albert et al., *Nat Immunol.*, 2(11):1010-1017, 2001.
Angel et al., *Mol. Cell. Biol.*, 7:2256, 1987.
Angel et al., *Cell*, 49:729, 1987b.
Angel et al., *Mol. Cell. Biol.*, 7:2256, 1987a.
Atchison and Perry, *Cell*, 46:253, 1986.
Atchison and Perry, *Cell*, 48:121, 1987.
Ausubel et al., In: *Current Protocols in Molecular Biology*, John, Wiley & Sons, Inc, New York, 1996.
Baichwal and Sugden, In: *Gene Transfer*, Kucherlapati (Ed.), NY, Plenum Press, 117-148, 1986.
Banerji et al., *Cell*, 27(2 Pt 1):299-308, 1981.
Banerji et al., *Cell*, 33(3):729-740, 1983.
Beneke, In: *Human Mycoses*, Upjohn Co., Kalamazoo, Mich., 1979.
Beretta et al., *EMBO J.*, 15:658-664, 1996.
Beretta et al., *J. Virol.*, 70:8993-8996, 1996.
Berkhout et al., *Cell*, 59:273-282, 1989.
Blanar et al., *EMBO J.*, 8:1139, 1989.
Blumberg et al., *Cell*, 104(1):9-19, 2001.
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Bulla and Siddiqui, *J. Virol.*, 62:1437, 1986.
Caley et al., *J. Virology*, 71(4):3031-3038, 1997.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Carbonelli et al., *FEMS Microbiol. Lett.*, 177(1):75-82, 1999.
Caudell et al., *J. Immunol.*, 168(12):6041-6046, 2002.
Celander and Haseltine, *J. Virology*, 61:269, 1987.
Celander et al., *J. Virology*, 62:1314, 1988.
Chandler et al., *Cell*, 33:489, 1983.
Chang et al., *Hepatology*, 14:134A, 1991.
Chang et al., *Mol. Cell. Biol.*, 9:2153, 1989.
Chattergoon et al., *Nat. Biotechnol.*, 18(9):974-979, 2000.
Chatterjee et al., *Proc. Natl. Acad. Sci. USA*, 86:9114, 1989.
Choi et al., *Cell*, 53:519, 1988.
Clark et al., *Hum. Gene Ther.*, 6(10):1329-1341, 1995.
Cocea, *Biotechniques*, 23(5):814-816, 1997.
Coffin, In: *Virology*, Fields et al. (Eds.), Raven Press, NY, 1437-1500, 1990.
Cohen et al., *J. Cell. Physiol.*, 5:75, 1987.
Costa et al., *Mol. Cell. Biol.*, 8:81, 1988.
Couch et al., *Am. Rev. Resp. Dis.*, 88:394-403, 1963.
Coupar et al., *Gene*, 68:1-10, 1988.
Cripe et al., *EMBO J.*, 6:3745, 1987.
Culotta and Hamer, *Mol. Cell. Biol.*, 9:1376, 1989.
Dandolo et al., *J. Virology*, 47:55-64, 1983.
Davis et al, *Curr. Biol.*, 6:146-148, 1996.
DeVilliers et al., *Nature*, 312(5991):242-246, 1984.
De Waal Malefyt et al., *J. Exp. Med.*, 174(4):1209-1220, 1991.
Deschamps et al., *Science*, 230:1174-1177, 1985.
Edbrooke et al., *Mol. Cell. Biol.*, 9:1908, 1989.
Edlund et al., *Science*, 230:912-916, 1985.
Ekmekcioglu et al., *Int. J. Cancer*, 94(1):54-59, 2001.
Ekmekcioglu et al., *Mol. Cancer Ther.*, 2(1):9-17, 2003.
Felgner et al., *Proc. Natl. Acad. Sci. USA*, 84(21):7413-7417, 1987.
Feng and Holland, *Nature*, 334:6178, 1988.
Feng et al., *Proc. Natl. Acad. Sci. USA*, 89:5447-5451, 1992.
Firak and Subramanian, *Mol. Cell. Biol.*, 6:3667, 1986.
Fisher et al., *Cancer Biol. Therapy*, 2(4):24-38, 2003.

Fisher et al., *Cancer Biol. Therapy*, 2(4):24-38, 2003.
Flotte et al., *Am. J. Respir. Cell Mol. Biol.*, 7(3):349-356, 1992.
Flotte et al., *Gene Ther.*, 2(1):29-37, 1995.
Flotte et al., *Proc. Natl. Acad. Sci. USA*, 90(22):10613-10617, 1993.
Foecking and Hofstetter, *Gene*, 45(1):101-105, 1986.
Fraley et al., *Proc. Natl. Acad. Sci. USA*, 76:3348-3352, 1979.
Friedmann, *Science*, 244:1275-1281, 1989.
Fujita et al., *Cell*, 49:357, 1987.
Gabizon et al., *Cancer Res.*, 50(19):6371-6378, 1990.
Gale et al., *Microbiol. Mol. Biol. Rev.*, 64:239-280, 2000.
Gale et al., *J. Virol.*, 73:6506-6516, 1999.
Gale et al., *Mol. Cell. Biol.*, 18:5208-5218, 1998.
Gale et al., *Mol. Cell. Biol.*, 18:859-871, 1998.
Gething and Sambrook, *Nature*, 355(6355):33-45, 1992.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Ghosh-Choudhury et al., *EMBO J.*, 6:1733-1739, 1987.
Gilles et al., *Cell*, 33:717, 1983.
Gloss et al., *EMBO J.*, 6:3735, 1987.
Godbout et al., *Mol. Cell. Biol.*, 8:1169, 1988.
Gomez-Foix et al., *J. Biol. Chem.*, 267:25129-25134, 1992.
Goodbourn and Maniatis, *Proc. Natl. Acad. Sci. USA*, 85:1447, 1988.
Goodbourn et al., *Cell*, 45:601, 1986.
Graham and Prevec, *Biotechnology*, 20:363-390, 1992.
Graham and Prevec, In: *Methods in Molecular Biology: Gene Transfer and Expression Protocol*, Murray (Ed.), Humana Press, Clifton, N.J., 7:109-128, 1991.
Graham et al, *J General Virology*, 36:59-74, 1977.
Greene et al., *Immunology Today*, 10:272, 1989
Grosschedl and Baltimore, *Cell*, 41:885, 1985.
Grunhaus et al., *Seminar in Virology*, 200(2):535-546, 1992.
Haines et al., *Virchows Arch. B Cell Pathol. Incl. Mol. Pathol.*, 62(3):151-158, 1992.
Haslinger and Karin, *Proc. Natl. Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Hermonat and Muzycska, *Proc. Natl. Acad. Sci. USA*, 81:6466-6470, 1984.
Herr and Clarke, *Cell*, 45:461, 1986.
Hersdorffer et al., *DNA Cell Biol.*, 9:713-723, 1990.
Herz and Gerard, *Proc. Natl. Acad. Sci. USA*, 90:2812-2816, 1993.
Hirochika et al., *J. Virol.*, 61:2599, 1987.
Hirsch et al., *Mol. Cell. Biol.*, 10:1959, 1990.
Holbrook et al., *Virology*, 157:211, 1987.
Horlick and Benfield, *Mol. Cell. Biol.*, 9:2396, 1989.
Horwich et al. *J. Virol.*, 64:642-650, 1990.
Huang et al., *Cell*, 27:245, 1981.
Huang et al., *Oncogene*, 20(48):7051-7063, 2001.
Hug et al., *Mol. Cell. Biol.*, 8:3065, 1988.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Jiang et al., *Oncogene*, 11(12):2477-2486, 1995.
Jiang et al., *Proc. Natl. Acad. Sci. USA*, 93(17):9160-9165, 1996.
Johnson et al., *Mol. Cell. Biol.*, 9:3393, 1989.
Jones and Shenk, *Cell*, 13:181-188, 1978.
Judware et al., *Mol. Cell Biol.*, 11(6):3259-3267, 1991.
Kadesch and Berg, *Mol. Cell. Biol.*, 6:2593, 1986.
Kaneda et al., *Science*, 243:375-378, 1989.
Kaplitt et al., *Nat Genet.*, 8(2):148-54, 1994.
Karin et al., *Mol. Cell. Biol.*, 7:606, 1987.
Karin et al., *Mol. Cell. Biol.*, 7:606, 1987.
Karlsson et al., *EMBO J.*, 5:2377-2385, 1986.
Katinka et al., *Cell*, 20:393, 1980.
Kato et al, *J. Biol. Chem.*, 266:3361-3364, 1991.
Kaufman, *J. Clin. Invest.*, 110(10):1389-1398, 2002.
Kawabe et al., *Molecular Therapy*, 6(5):637-644, 2002.
Kawamoto et al., *Mol. Cell. Biol.*, 8:267, 1988.
Kiledjian et al., *Mol. Cell. Biol.*, 8:145, 1988.
Klamut et al., *Mol. Cell. Biol.*, 10:193, 1990.
Koch et al., *Mol. Cell. Biol.*, 9:303, 1989.
Koromilas et al., *Science*, 257(5077):1685-1689, 1992.
Kotin et al., *Proc. Natl. Acad. Sci. USA*, 87(6):2211-2215, 1990.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kumar et al., *EMBO J.*, 16:406-416, 1997.
Kumar et al., *Proc. Natl. Acad. Sci. USA*, 91:6288-6292, 1994.
Kunz et al., *Nucl. Acids Res.*, 17:1121, 1989.
Kyte and Doolittle, *J. Mol. Biol.*, 57(1):105-32, 1982.
LaFace et al., *Virology*, 162(2):483-486, 1988.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Laughlin et al., *J. Virol.*, 60(2):515-524, 1986.
Le Gal La Salle et al., *Science*, 259:988-990, 1993.
Lebedeva et al., *Semin. Cancer Biol.*, 13(2):169-178, 2003.
Lebkowski et al., *Mol. Cell. Biol.*, 8(10):3988-3996, 1988.
Lebkowski et al., *Mol. Cell. Biol.*, 8(10):3988-3996, 1988.
Lee et al., *Nature*, 294:228, 1981.
Lee et al., *Nucleic Acids Res.*, 12:4191-206, 1984.
Lenardo et al., *Cell*, 57:287-294, 1989.
Levenson et al., *Hum. Gene Ther.*, 9(8):1233-1236, 1998.
Levinson et al., *Nature*, 295:79, 1982.
Levrero et al., *Gene*, 101:195-202, 1991.
Lin et al., *Mol. Cell. Biol.*, 10:850, 1990.
Liu et al., *J. Biol. Chem.*, 270:24864-24870, 1995.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90-94, 1991.
Magner and Papagiannes, *Endocrinology*, 122(3):912-920, 1988.
Majors and Varmus, *Proc. Natl. Acad. Sci. USA*, 80:5866, 1983.
Mann et al., *Cell*, 33:153-159, 1983.
Maran et al., *Science*, 265:789-792, 1994.
Markowitz et al., *J. Virol.*, 62:1120-1124, 1988.
McCarty et al., *J. Virol.*, 65(6):2936-2945, 1991.
McLaughlin et al., *J. Virol.*, 62(6):1963-1973, 1988.
McLaughlin et al., *J. Virol.*, 62(6):1963-1973, 1988.
McNeall et al., *Gene*, 76:81, 1989.

Merrick and Hershey, In: *Translational control*, Hershey et al. (Eds.), Cold Spring Harbor Laboratory Press, NY, 31-70, 1996.
Meurs et al., *Cell*, 62:379-390, 1990.
Meurs et al., *Proc. Natl. Acad. Sci. USA*, 90:232-236, 1993.
Mhashilkar et al., *Mol Med.*, 7:271-282, 2001.
Mhashilkar et al., *Mol. Med.*, 7:271-282, 2001.
Mhashilkar et al., *Molecular Therapy*, 8(2):207-219, 2003.
Miksicek et al., *Cell*, 46:203, 1986.
Mordacq and Linzer, *Genes and Dev.*, 3:760, 1989.
Moreau et al., *Nucl. Acids Res.*, 9:6047, 1981.
Muesing et al., *Cell*, 48:691, 1987.
Muzyczka, *Curr. Topics Microbiol. Immunol.*, 158:97-129, 1992.
Nemunaitis, *Clin. Infect. Dis.*, 26(6):1279-1281, 1998.
Nemanaitis et al., *Cancer Res.*, 60:6359-6366, 2000.
Ng et al., *Nuc. Acids Res.*, 17:601, 1989.
Nicolas and Rubinstein, In: *Vectors: A survey of molecular cloning vectors and their uses*, Rodriguez and Denhardt (Eds.), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Oh et al., *Biochem. Biophys. Res. Commun.*, 301:225-230, 2003.
Ohi et al., *Gene*, 89(2):279-282, 1990.
Ondek et al., *EMBO J.*, 6:1017, 1987.
Ornitz et al., *Mol. Cell. Biol.*, 7:3466, 1987.
Palmiter et al., *Nature*, 300:611, 1982.
Paskind et al., *Virology*, 67:242-248, 1975.
Pataer et al., *Cancer Res.*, 62(8):2239-2243, 2002.
Pataer et al., *J Thoracic Cardiov. Surgery*, 126(6):1328-1325, 2003.
Pavio et al., *J. Virol.*, 77(6):3578-3585, 2003.
PCT Appln. WO 98/07408
PCT Appln. WO 98/28425
Pech et al., *Mol. Cell. Biol.*, 9:396, 1989.
Pelletier and Sonenberg, *Nature*, 334(6180):320-325, 1988.
Perez-Stable and Constantini, *Mol. Cell. Biol.*, 10:1116, 1990.
Petryshyn et al., *J. Biol. Chem.*, 259(23):14736-14742, 1984.
Petryshyn et al., *Proc. Natl. Acad. Sci. USA*, 85(5):1427-1431, 1988.
Philip et al., *J. Biol. Chem.*, 268(22):16087-16090, 1993.
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Queen and Baltimore, *Cell*, 35:741, 1983.
Quinn et al., *Mol. Cell. Biol.*, 9:4713, 1989.
Racher et al., *Biotechnology Techniques*, 9:169-174, 1995.
Ragot et al., *Nature*, 361:647-650, 1993.
Redondo et al., *Science*, 247:1225, 1990.
Reisman and Rotter, *Mol. Cell. Biol.*, 9:3571, 1989.
Remington's Pharmaceutical Sciences, 15$^{th}$ ed., pages 1035-1038 and 1570-1580, Mack Publishing Company, Easton, Pa., 1980.
Renan, *Radiother. Oncol.*, 19:197-218, 1990.
Resendez Jr. et al., *Mol. Cell. Biol.*, 8:4579, 1988.
Restifo, *Curr. Opin. Immunol.*, 12(5):597-603, 2000.
Rich et al., *Hum. Gene Ther.*, 4:461-476, 1993.
Ridgeway, In: *Vectors: A survey of molecular cloning vectors and their uses*, Rodriguez and Denhardt (Eds.), Stoneham: Butterworth, 467-492, 1988.
Ripe et al., *Mol. Cell. Biol.*, 9:2224, 1989.
Rittling et al., *Nuc. Acids Res.*, 17:1619, 1989.
Ron, *J. Clin. Invest.*, 110(10):1383-1388, 2002.
Rosen et al., *Cell*, 41:813, 1988.
Rosenfeld et al., *Cell*, 68:143-155, 1992.
Rosenfeld et al., *Science*, 252:431-434, 1991.
Roux et al., *Proc. Natl. Acad. Sci. USA*, 86:9079-9083, 1989.
Saeki et al., *Gene Ther.*, 7:2501-2057, 2000.
Saelens et al., *J. Biol. Chem.*, 276(45):41620-41628, 2001.
Saiki et al., *Oncogene*, 21(29):4558-4566, 2002.
Sakai et al., *Genes and Dev.*, 2:1144, 1988.
Sambrook et al., In: *Molecular cloning*, Cold Spring Harbor Laboratory Press, Cold Spring Harbor, N.Y., 2001.
Samulski et al., *EMBO J*, 10:3941-3950, 1991.
Samulski et al., *J. Virol*, 63:3822-3828, 1989.
Sarkar et al., *Proc. Natl. Acad. Sci. USA*, 99(15):10054-10059, 2002.
Satake et al., *J. Virology*, 62:970, 1988.
Schaefer et al., *J. Immunol.*, 166(10):5859-5863, 2001.
Schaffner et al., *J. Mol. Biol.*, 201:81, 1988.
Scrip's Antifungal Report, by PJB Publications Ltd, 1992.
Searle et al., *Mol. Cell. Biol.*, 5:1480, 1985.
Sharp and Marciniak, *Cell*, 59:229, 1989.
Shaul and Ben-Levy, *EMBO J.*, 6:1913, 1987.
Shelling and Smith, *Gene Therapy*, 1: 165-169, 1994.
Sherman et al., *Mol. Cell. Biol.*, 9:50, 1989.
Shtrichman et al., *Infect. Immun.* 70:5579-5588, 2002.
Sleigh and Lockett, *J. EMBO*, 4:3831, 1985.
Smith, In: *Opportunistic Mycoses of Man and Other Animals*, CAB International, Wallingford, UK, 1989.
Smyth-Templeton et al., *DNA Cell Biol.*, 21(12):857-867, 2002.
Solodin et al., *Biochemistry*, 34(41):13537-13544, 1995.
Soo et al., *J. Cell. Biochem.*, 74(1):1-10, 1999.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Stratford-Perricaudet and Perricaudet, In: *Human Gene Transfer*, Eds. Cohen-Haguenauer and Boiron, John Libbey Eurotext, France, 51-61, 1991.
Stratford-Perricaudet et al., *Hum. Gene. Ther.*, 1:241-256, 1990.
Stuart et al., *Nature*, 317:828, 1985.
Su et al., *Proc. Natl. Acad. Sci. USA*, 95:14400, 1998.
Sudhakar et al., *Biochemistry*, 39(42):12929-12938, 2000.
Sullivan and Peterlin, *Mol. Cell. Biol.*, 7:3315, 1987.
Swartzendruber and Lehman, *J. Cell. Physiology*, 85:179, 1975.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati (Ed.), NY, Plenum Press, 149-188, 1986.
Thierry et al., *Proc. Natl. Acad. Sci. USA*, 92(21):9742-9746, 1995.
Thiesen et al., *J. Virology*, 62:614, 1988.
Top et al., *J. Infect. Dis.*, 124:155-160, 1971.
Tratschin et al., *Mol. Cell. Biol.*, 4:2072-2081, 1984.
Tratschin et al., *Mol. Cell. Biol.*, 5:3258-3260, 1985.
Treisman, *Cell*, 42:889, 1985.
Tronche et al., *Mol. Biol. Med.*, 7:173, 1990.
Trudel and Constantini, *Genes and Dev.* 6:954, 1987.
Tsukamoto et al., *Nat. Genet.*, 9(3):243-248, 1995.
Tyndell et al., *Nuc. Acids. Res.*, 9:6231, 1981.
Vannice and Levinson, *J. Virology*, 62:1305, 1988.
Vasseur et al., *Proc Natl. Acad. Sci. U.S.A.*, 77:1068, 1980.
Vattem et al., *Eur. J. Biochem.*, 268(4):1143-1153, 2001.

Walsh et al., *J. Clin. Invest,* 94:1440-1448, 1994.
Walsh et al., *J. Clin. Invest,* 94:1440-1448, 1994.
Wang and Calame, *Cell,* 47:241, 1986.
Weber et al., *Cell,* 36:983, 1984.
Wei et al., *Gene Therapy,* 1:261-268, 1994.
Weinberger et al. *Mol. Cell. Biol.,* 8:988, 1984.
Winoto and Baltimore, *Cell* 59:649, 1989.
Wong et al., *Gene,* 10: 87-94, 1980.
Yang and Huang, *Gene Therapy,* 4 (9):950-960, 1997.
Yang et al., *J. Virol.,* 68:4847-4856, 1994.
Yeo et al., *Biochem. Biophys. Res. Commun.,* 160(3):1421-1428, 1989.
Yoder et al., *Blood,* 82 (Supp.): 1:347A, 1994.
Yutzey et al. *Mol. Cell. Biol.,* 9:1397, 1989.
Zhang et al., *Hum. Gene Ther.,* 13:2051-2064, 2002.
Zhang et al., *J. Biol. Chem.,* 275:24436, 2000.
Zhou et al., *Exp. Hematol,* 21:928-933, 1993.
Zhou et al., *J. Exp. Med.,* 179:1867-1875, 1994.
Zhu et al., *Science,* 261(5118):209-211, 1993.

What is claimed is:

1. A method of suppressing or preventing an infection of a subject by a pathogen, comprising administering to the subject a composition comprising: (a) a therapeutically effective amount of an MDA-7 polypeptide or a nucleic acid encoding the MDA-7 polypeptide; and (b) a pharmaceutically acceptable preparation suitable for delivery to said subject, and wherein the MDA-7 suppresses or prevents the infection, wherein the pathogen is a virus.

2. The method of claim 1, wherein the virus is an endoplasmic reticulum-tropic virus.

3. The method of claim 2, wherein the virus is Hepatitis C virus, a flavivirus species, HHV6, rubella, LCMV, HIV, or Hepatitis B virus.

4. The method of claim 1, wherein the virus is influenza A, influenza B, influenza C, parainfluenza, paramyxoviruses, Newcastle disease virus, respiratory syncytial virus, measles, mumps, adenoviruses, adenoassociated viruses, parvoviruses, Epstein-Barr virus, rhinoviruses, coxsackieviruses, echoviruses, reoviruses, rhabdoviruses, coronavirus, polioviruses, herpes simplex, cytomegaloviruses, papillomaviruses, virus B, varicella-zoster, poxviruses, rabies, picornaviruses, rotavirus, or Kaposi associated herpes virus.

5. The method of claim 1, wherein the subject is a mammal.

6. The method of claim 5, wherein the mammal is a human.

7. The method of claim 1, wherein administering comprises providing to said subject an expression cassette comprising a promoter, active in the subject, operably linked to a polynucleotide encoding an MDA-7 polypeptide.

8. The method of claim 7, wherein the expression cassette is carried in a viral vector.

9. The method of claim 8, wherein the viral vector is an adenoviral vector, a retroviral vector, a vaccinia viral vector, an adeno-associated viral vector, or a poxviral vector.

10. The method of claim 9, wherein the viral vector is an adenoviral vector.

11. The method of claim 7, wherein the expression cassette is carried in a nonviral vector.

12. The method of claim 11, wherein the nonviral vector comprises a lipid.

13. The method of claim 1, wherein the MDA-7 polypeptide comprises amino acids 49 to 206 of SEQ ID NO: 2.

14. The method of claim 1, wherein the MDA-7 polypeptide comprises a sequence of SEQ ID NO: 2.

15. The method of claim 1, wherein the composition is formulated for oral administration, topical administration, intralesional injection, or intravenous administration.

16. The method of claim 1, further comprising administering at least one additional agent to prevent or suppress the infection in the subject.

17. A method of suppressing or preventing a viral infection of a cell, comprising: (a) obtaining an MDA-7 polypeptide or a nucleic acid encoding the MDA-7 polypeptide; and (b) contacting the cell with the MDA-7 polypeptide or the nucleic acid encoding the MDA-7 polypeptide; wherein the MDA-7 suppresses or prevents infection of the cell.

18. The method of claim 17, wherein the viral infection is caused by an oncogenic virus.

19. The method of claim 17, wherein the viral infection is caused by an endoplasmic reticulum-tropic virus.

20. The method of claim 17, wherein the viral infection is caused by is Hepatitis C virus, a flavivirus species, HHV6, rubella, LCMV, HIV, or Hepatitis B virus.

21. The method of claim 17, wherein the viral infection is caused by influenza A, influenza B, influenza C, parainfluenza, paramyxoviruses, Newcastle disease virus, respiratory syncytial virus, measles, mumps, adenoviruses, adenoassociated viruses, parvoviruses, Epstein-Barr virus, rhinoviruses, coxsackieviruses, echoviruses, reoviruses, rhabdoviruses, coronavirus, polioviruses, herpes simplex, cytomegaloviruses, papillomaviruses, virus B, varicella-zoster, poxviruses, rabies, picornaviruses, rotavirus, or Kaposi associated herpes virus.

22. The method of claim 17, wherein the cell is a mammalian cell.

23. The method of claim 22, wherein the mammalian cell is a cancer cell.

24. The method of claim 17, wherein the MDA-7 polypeptide or nucleic acid encoding the MDA-7 polypeptide comprises an expression cassette comprising a promoter, active in the cell, operably linked to a polynucleotide encoding an MDA-7 polypeptide.

25. The method of claim 24, wherein the expression cassette is carried in a viral vector.

26. The method of claim 25, wherein the viral vector is an adenoviral vector, a retroviral vector, a vaccinia viral vector, an adeno-associated viral vector, or a poxviral vector.

27. The method of claim 26, wherein the viral vector is an adenoviral vector.

28. The method of claim 24, wherein the expression cassette is carried in a nonviral vector.

29. The method of claim 28, wherein the nonviral vector comprises a lipid.

30. The method of claim 17, wherein the MDA-7 polypeptide comprises amino acids 49 to 206 of SEQ ID NO: 2.

31. The method of claim 17, wherein the MDA-7 polypeptide comprises the sequence of SEQ ID NO: 2.

32. The method of claim 17, further comprising administering at least one additional agent to prevent or suppress the viral infection in the cell.

* * * * *

UNITED STATES PATENT AND TRADEMARK OFFICE
CERTIFICATE OF CORRECTION

PATENT NO.         : 8,034,790 B2
APPLICATION NO.    : 11/001702
DATED              : October 11, 2011
INVENTOR(S)        : Sunil Chada It is certified that error appears in the above-identified patent and that said Letters Patent is hereby corrected as shown below:

In title page, item (63) Related U.S. Application Data, delete "Continuation of" and insert --Provisional-- therefor.

In claim 14, column 59, line 54, delete "a sequence" and insert --the sequence-- therefor.

Signed and Sealed this
Thirteenth Day of March, 2012

David J. Kappos
*Director of the United States Patent and Trademark Office*